(12) United States Patent
Goodman

(10) Patent No.: US 6,616,613 B1
(45) Date of Patent: Sep. 9, 2003

(54) PHYSIOLOGICAL SIGNAL MONITORING SYSTEM

(75) Inventor: Jesse B. Goodman, Mississauga (CA)

(73) Assignee: Vitalsines International, Inc., Mississauga (CA)

( * ) Notice: Subject to any disclaimer, the term of this patent is extended or adjusted under 35 U.S.C. 154(b) by 0 days.

(21) Appl. No.: 09/559,424

(22) Filed: Apr. 27, 2000

(51) Int. Cl.[7] .................................................. A61B 5/02
(52) U.S. Cl. ........................ 600/504; 600/500; 600/300
(58) Field of Search ................................ 600/300–301, 600/323, 500, 504, 507; 128/905, 920–925; 713/186

(56) References Cited

U.S. PATENT DOCUMENTS

| | | | |
|---|---|---|---|
| 3,132,643 A | 5/1964 | Baum et al. | |
| 3,998,550 A | 12/1976 | Konishi et al. | |
| 4,355,642 A | 10/1982 | Alferness | |
| 4,418,700 A | 12/1983 | Warner | |
| 4,432,374 A | 2/1984 | Osanai | |
| 4,510,941 A | 4/1985 | Semrow et al. | |
| 4,807,638 A | 2/1989 | Sramek | |
| 4,869,261 A | 9/1989 | Penáz | |
| 4,896,262 A | 1/1990 | Wayama et al. | |
| 4,927,264 A | 5/1990 | Shiga et al. | |

(List continued on next page.)

FOREIGN PATENT DOCUMENTS

| GB | WO 99/32030 | 7/1999 |
|---|---|---|
| GB | 2 356 250 A | 5/2001 |
| GB | 2 356 251 A | 5/2001 |
| GB | 2 356 252 A | 5/2001 |

OTHER PUBLICATIONS

"A Family History of NIDDM Is Associated with Decreased Aortic Distensibility in Normal Healthy Young Adult Subjects" Kathleen D. Hopkins et al. *Diabetes Care* vol. 19, No. 5: 501–503 May 1996.

"A micropocessor based photoplethysmograph for use in clinical practice" I.P. Wright et al. *Anaesthesia* vol. 50: 875–878, 1995.

"AC Coupling Instrumentation and Difference Amplifiers" R. Mark Stitt Aug., *Application Bulletin* 1991.

(List continued on next page.)

*Primary Examiner*—Robert L. Nasser
*Assistant Examiner*—Patricia Mallari
(74) *Attorney, Agent, or Firm*—Bereskin & Parr

(57) ABSTRACT

A health monitoring and biofeedback system comprising a photoplethysmography (PPG) sensor, a processing device, and a Web site server for determining, displaying and analyzing various cardiovascular parameters. The PPG sensor is installed within a manually operated user input device such as a mouse or keyboard, measures a user's blood volume contour and transmits it to a processing device such as a personal computer or a personal digital assistant (PDA). The system determines a plurality of cardiovascular indices including mean blood pressure, heart rate, body temperature, respiratory rate, and arterial compliance on the basis of signal characteristics of the systolic wave pulse and the systolic reflected wave pulse present within the digital volume pulse derived from the PPG pulse contour. Signal characteristics of the systolic reflected wave pulse can be determined through various pulse analysis techniques including derivative analysis of the digital volume pulse signal, bandpass filtering or respiratory matrix frequency extraction techniques. By subtracting the systolic reflected wave pulse contour from the digital volume pulse contour, characteristics of the systolic wave pulse can also be identified. The system also provides for the accurate determination of systolic and diastolic blood pressure by using a non-invasive blood pressure monitor to calibrate the relationships between arterial or digital blood pressure and characteristics of the user's digital volume pulse contour. In this way, a wide variety of cardiovascular and respiratory data can be obtained. The system also facilitates the transmittal of such data to the system web site for further analysis, storage, and retrieval purposes.

39 Claims, 25 Drawing Sheets

U.S. PATENT DOCUMENTS

| | | | |
|---|---|---|---|
| 5,002,061 A | 3/1991 | Close et al. | |
| 5,111,817 A | 5/1992 | Clark et al. | |
| 5,140,990 A | 8/1992 | Jones et al. | |
| 5,146,926 A | 9/1992 | Cohen | |
| 5,152,296 A | 10/1992 | Simons | |
| 5,237,997 A | 8/1993 | Greubel et al. | |
| 5,265,011 A | 11/1993 | O'Rourke | |
| 5,269,310 A | 12/1993 | Jones et al. | |
| 5,273,036 A | 12/1993 | Kronberg et al. | |
| 5,293,874 A | 3/1994 | Takahashi et al. | |
| 5,309,916 A | 5/1994 | Hatschek | |
| 5,351,695 A | 10/1994 | Mills et al. | |
| 5,396,893 A | 3/1995 | Oberg et al. | |
| 5,423,322 A | 6/1995 | Clark et al. | |
| 5,485,848 A | 1/1996 | Jackson et al. | |
| 5,497,778 A | 3/1996 | Hon | |
| 5,511,546 A | 4/1996 | Hon | |
| 5,546,943 A * | 8/1996 | Gould | 600/425 |
| 5,560,366 A | 10/1996 | Harada et al. | |
| 5,626,140 A | 5/1997 | Feldman et al. | |
| 5,649,543 A | 7/1997 | Hosaka et al. | |
| 5,704,363 A | 1/1998 | Amano | |
| 5,713,350 A * | 2/1998 | Yokota et al. | 600/300 |
| 5,715,826 A | 2/1998 | Horrocks et al. | |
| 5,741,217 A * | 4/1998 | Gero | 600/547 |
| 5,766,132 A | 6/1998 | Yasukawa et al. | |
| 5,784,151 A * | 7/1998 | Miller et al. | 356/41 |
| 5,800,349 A * | 9/1998 | Isaacson et al. | 600/323 |
| 5,827,179 A | 10/1998 | Lichter et al. | |
| 5,853,364 A | 12/1998 | Baker, Jr. et al. | |
| 5,862,805 A * | 1/1999 | Nitzan | 128/898 |
| 5,865,755 A | 2/1999 | Golub | |
| 5,876,348 A | 3/1999 | Sugo et al. | |
| 5,882,311 A | 3/1999 | O'Rourke | |
| 5,941,837 A | 8/1999 | Amano et al. | |
| 5,964,701 A | 10/1999 | Asada et al. | |
| 5,987,519 A | 11/1999 | Peifer et al. | |
| 5,990,866 A | 11/1999 | Yollin | |
| 6,017,313 A | 1/2000 | Bratteli et al. | |
| 6,038,666 A * | 3/2000 | Hsu et al. | 713/186 |
| 6,047,203 A | 4/2000 | Sackner et al. | |
| 6,093,146 A * | 7/2000 | Filangeri | 600/300 |
| 6,095,985 A * | 8/2000 | Raymond et al. | 600/513 |
| 6,163,715 A | 12/2000 | Larsen et al. | |
| 6,168,563 B1 * | 1/2001 | Brown | 600/301 |
| 6,190,314 B1 | 2/2001 | Ark et al. | |
| 6,222,189 B1 | 4/2001 | Misner et al. | |
| 6,264,614 B1 * | 7/2001 | Albert et al. | 600/528 |
| 6,266,546 B1 | 7/2001 | Steuer et al. | |
| 6,290,650 B1 | 9/2001 | Butterfield et al. | |
| 6,302,844 B1 * | 10/2001 | Walker et al. | 600/300 |
| 6,317,834 B1 * | 11/2001 | Gennaro et al. | 713/186 |
| 6,336,900 B1 * | 1/2002 | Alleckson et al. | 600/485 |
| 6,371,921 B1 | 4/2002 | Caro et al. | |
| 6,416,471 B1 * | 7/2002 | Kumar et al. | 600/300 |
| 6,496,711 B1 | 12/2002 | Athan et al. | |

OTHER PUBLICATIONS

"AC Instrumentation Amplifier for Bioimpedance Measurements" Ramón Pallás–Areny et al. *Communications* vol. 40, No. 8: 830–833 Aug. 1993.

"Age–Related Abnormalities in Arterial Compliance Identified by Pressure Pulse Contour Analysis" Gary E. McVeigh et al. *Hypertension* vol. 33: 1392–1398, 1999.

"An Integrated Blood Volume Pulse Biofeedback System for Migraine Treatment" Kenneth L. Lichstein et al. *Biofeedback and Self–Regulation,* vol. 8, No. 1: 127–134 1983.

"An Ultra–High Common–Mode Rejection Ratio (CMRR) AC Instrumentation Amplifier for Laplacian Electrocardiographic Measurement" Chih–Cheng Lu et al. *Instrumentation Research* Jan./Feb.: 76–83, 1999.

"Aortic Compliance in Human Hypertension" Zhaorong Liu et al. *Hypertension* vol. 14; 129–136, 1989.

"Aortic Distensibility in Patients with Cerebrovascular Disease" E.D. Lehmann et al. *Clinical Science* vol. 89: 247–253, 1995.

"Aortic Pulse Wave Velocity as a Marker of Cardiovascular Risk in Hypertensive Patients" Jacques Blacher, et al. *Hypertension* vol. 33: 1111–1117, 1999.

"Arterial compliance increases after moderate–intensity cycling" Bronwyn A. Kingwell et al. *American Journal of Physiology* vol. 273: 2186–2191, 1997.

"Artifact reduction in photoplethysmography" Matthew J. Hayes et al. *Applied Optics* vol. 37, No. 31: 7437–7446, Nov. 1998.

"Assessment of Vasoactive Agents and Vascular Aging by the Second Derivative of Photoplethysmogram Waveform" Kenji Takazawa et al. *Hypertension* vol. 32: 365–370, 1998.

"Autonomic control of skin microvessels: assessment by power spectrum of photoplethysmographic waves" Luciano Bernardi et al. *Clinical Science* vol. 90: 345–355, 1996.

"Blood Pressure Control: A Comparison of Feedback and Instructions Using Pulse Wave Velocity Measurements" Andrew Steptoe *Psychophysiology* vol. 13, No. 6: 528–535, Nov. 1976.

"Body height as a determinant of carotid pulse contour in humans" Gérard M. London et al, *Hypertension* vol. 10: 593–595, 1992.

"Calculation of Pulse–Wave Velocity Using Cross Correlation–Effects of Reflexes in the Arterial Tree" Morten Benthin et al. *Ultrasound in Medicine & Biology* vol. 17, No. 5: 461–469, 1991.

"Comparison of Biofeedback Pulse Wave Velocity and Progressive Relaxation in Essential Hypertensives" Peter Walsh et al. *Perceptual and Motor Skills* vol. 44, 839–843, 1977.

"Computation of Aortic Pulse Wave Velocity and Aortic Extensibility from Pressure Gradient Measurements" Alain C. Lapointe et al. *Canadian Journal of Physiology Pharmacology* vol. 53: 940–946, 1975.

"Continuous assessment of hemodynamic control by complex demodulation of cardiovascular variability" Junichiro Hayano et al. *American Journal of Physiology* vol. 33: 1229–1238, 1993.

"Differential effects of wave reflections a peripheral resistance on aortic blood pressure: a model–based study" David S. Berger et al. *American Journal of Physiology* vol. 266: 1626–1642, 1994.

"Early autonomic dysfunction in patients with diabetes mellitus assessed by spectral analysis of heart rate and blood pressure variability" K. Laederach–Hofmann et al, *Clinical Physiology* vol. 19, No. 2: 97–106, 1999.

"Elastic Properties and Windkessel Function of the Human Aorta" Gustav G. Belz *Cardiovasc Drugs Ther* vol. 9: 73–83, 1995.

"Estimation of Central Aortic Pressure Waveform by Mathematical Transformation of Radial Tonometry Pressure" Chen–Huan Chen et al. *Circulation* vol. 95: 1827–1837, 1997.

"Exponentially Tapered T–tube Model in the Characterization of Arterial Non–uniformity" Kuo–Chu Chang et al. *J. Theor. Biology* vol. 183: 35–46, 1996.

"Functional origin of reflected pressure waves in a multibranched model of the human arterial system" Mustafa Karamanoglu et al. *American Journal of Physiology* vol. 267: 1681–1688, 1994.

"Fundamentals of clinical cardiology" Jerrold S. Liebermann. M.D. *American Heart Journal* vol. 99, No. 4: 517–527, 1980.

"Haemodynamic basis for the development of left ventricular failure in systolic hypertension and for its logical therapy" Nico Westerhof et al. *Hypertension* vol. 13: 943–952, 1995.

"Influence of aortic Compliance on Coronary Blood Flow" Francis L. Abel *Circulatory Shock* vol. 12: 265–276, 1984.

"LIFESHIRT.COM, Vital Signs Online" <<http://www.lifeshirt.com/pubdocs/overview.html>>Mar. 22, 2000.

"Manipulation of Ascending Aortic Pressure and Flow Wave Reflections with the Valsalva Maneuver: Relationship to Input Impedance" Joseph P. Murgo et al. *Circulation* vol. 63, No. 1: 122–132, 1981.

"Measurement of Heart Rate Variability: A Clinical Tool or a Research Toy?" Heikki V. Huikuri et al. *Journal of the American College of Cardiology* vol. 34, No. 7: 1878–1883, 1999.

"Measurement of Pulse–Wave Velocity Using a Beat–Sampling Technique" J.D. Pruett et al. *Annals of Biomedical Engineering* vol. 16: 341–347, 1988.

"Monitoring of heart and respiratory rates by photoplethysmography using a digital filtering technique" K. Nakajima et al. *Med. Eng. Phys.* vol. 18: 365–372, Jul. 1996.

"Monitoring of respiratory and heart rates using a fibre–optic sensor" L.G. Lindberg et al. *Medical & Biological Engineering & Computing* vol. 30: 533–537, 1992.

"Nonhuman primate model for regional wave travel and reflections along aortas" R.D. Latham et al. *American Journal of Physiology* vol. 253: 299–306, 1987.

"Noninvasive Determination of Age–Related Changes in the Human Arterial Pulse" R. Kelly, MB et al. *Circulation* vol. 80: 1652–1659, 1989.

"Non–invasive measurements of arterial structure and function: repeatability interrelationshis and trial sample size" Yu–Lu Liang et al. *Clinical Science* vol. 95: 669–679, 1998.

"Noninvasive Pulse Oximetry Utilizing Skin Reflectance Photoplethysmography" Yitzhak Mendelson et al. *IEEE Transactions of Biomedical Engineering* vol. 35, No. 10: 798–805, Oct. 1988.

"On–line Synthesis of the Human Ascending Aortic Pressure Pulse from the Finger Pulse" Mustafa Karamanoglu et al. *Hypertension* vol. 30, No. 6: 1416–1424, 1997.

"Photo–Electric Plethysmography as a Monitoring Device in Anaesthesia" J.C. Dorlas et al *British Journal of Anaesthesiology* vol. 57: 524–530, 1985.

"Photoplethysmographic Assessment of Pulse Wave Reflection" Philip J. Chowienczyk et al. *Journal of the American College of Cardiology* vol. 34, No. 7: 2007–2014, 1999.

"Pressure wave propagation in a multibranched model of the human upper limb" Mustafa Karamanoglu et al. *American Journal of Physiology* vol. 269: 1363–1369, 1995.

"Pulsatile Flow and Pressure in Human Systemic Arteries" Michael F. O'Rourke et al. *Circulation Research* vol. 46: 363–372, 1980.

"Pulse wave analysis" Michael F. O'Rourke et al. *Hypertension* vol. 14: 147–157, 1996.

"Pulse Wave Analysis and Arterial Stiffness" Ian B. Wilkinson et al. *Journal of Cardiovascular Pharmacology* vol. 32: 33–37, 1998.

"Reflection in the systemic arterial system: effects of aortic and carotid occlusion" G.C. Van Den Bos et al. *Cardiovascular Research* vol. 10: 565–573, 1976.

"Regional wave travel and reflections along the human aorta: a study with six simultaneous micromanometric pressures" Ricky D. Latham et al. *Circulation* vol. 72, No. 6: 1257–1269, 1985.

"Relaxation pretraining, pulse wave velocity and thermal biofeedback in the treatment of essential hypertension" Carolyn Buby et al. *International Journal of Psychophysiology* vol. 9: 225–230, 1990.

"Role of pulse wave velocity for assessing autonomic nervous system activities in reference to heart rate variability" M. Okada et al. *Medical Information* vol. 21, No. 1: 81–90, 1996.

"The Control of Blood Pressure Using Pulse–Wave Velocity Feedback" Andrew Steptoe et al. *Journal of Psychosomatic Research* vol. 20: 417–424, 1976.

"The Genesis of the Pulse Contours of the Distal Leg Arteries in Man " R. Busse et al. *Pflüger Arch* vol. 360: 63–79, 1975.

"Time–Frequency Distribution Technique in Biological Signal Processing" Xiang Wang, PhD et al. *Biomedical Instrumentation & Technology* vol. 29: 203–212, May/Jun. 1995.

"Towards Optimization of Wave Reflection: Therapeutic Goal for Tomorrow" Michael Francis O'Rourke vol. 23: 511–515, 1996.

"Two Arterial Effective Reflecting Sites May Appear as One to the Heart" Roberto Burattini, et al. *Circulation Research* vol. 68: 85–99, 1991.

"Use of Pulse Transit Time as a Measure of Inspiratory Effort in Patients with Obstructive Sleep Apnoea" D.J. Pitson et al. vol. 8: 1669–1674, 1995.

"Use of Two Oximeters to Investigate a Method of Movement Artefact Rejection Using Photoplethysmographic Signals" A.R. Visram *British Journal of Anaesthesia* vol. 72: 388–392, 1994.

"Value to Beat–to–Beat Blood Pressure Changes, Detected By Pulse Transit Time, in the Management of the Obstructive Sleep Apnoea/Hypopnoea Syndrome" D.J.Pitson et al. vol. 12: 685–692, 1998.

"Vascular Compliance as a Measure of Biological Age" Christopher J. Bulpitt et al. *Journal of American Geriatric Society* vol. 47: 657–663, 1999.

"Wave Reflection in the Systemic Circulation and its Implications in Ventricular Function" Michael F. O'Rourke et al. *Hypertension* vol. 11: 327–337, 1993.

"Wave Reflections and the Arterial Pulse" Michael F. O'Rourke et al. *Arch Intern Med* vol. 144: 366–371, Feb. 1984.

C J Harland et al., "Electric potential probes—new directions in the remote sensing of the human body", Measurement Science and Technology, vol. 13, 2002, pp. 163–169.

Sandrine C. Millasseau et al., "Noninvasive Assessment of the Digital Volume Pulse Comparison With the Peripheral Pressure Pulse", Hypertension, vol. 36, Dec. 2000, pp. 952–956.

Boo–Ho Yang et al., "Sensor Fusion For Noninvasive Continuous Monitoring Of Pulsating Blood Pressure Based On An Arterial Hemodynamic Model", www.thoughttechnology.com/gsr.htm www.rjlsystems.com/research/ipg1.html www.medis–de.com/products.html http://hrf.jsc.nasa.gov/cbpd.htm.

Philip J. Chowienczyk et al., Photoplethysmographic Assessment of Pulse Wave Reflection, Journal of American College of Cardiology, vol. 34, No. 7, 1999, Elsevier Science Inc., London, United Kingdom and Lund, Sweden.

* cited by examiner

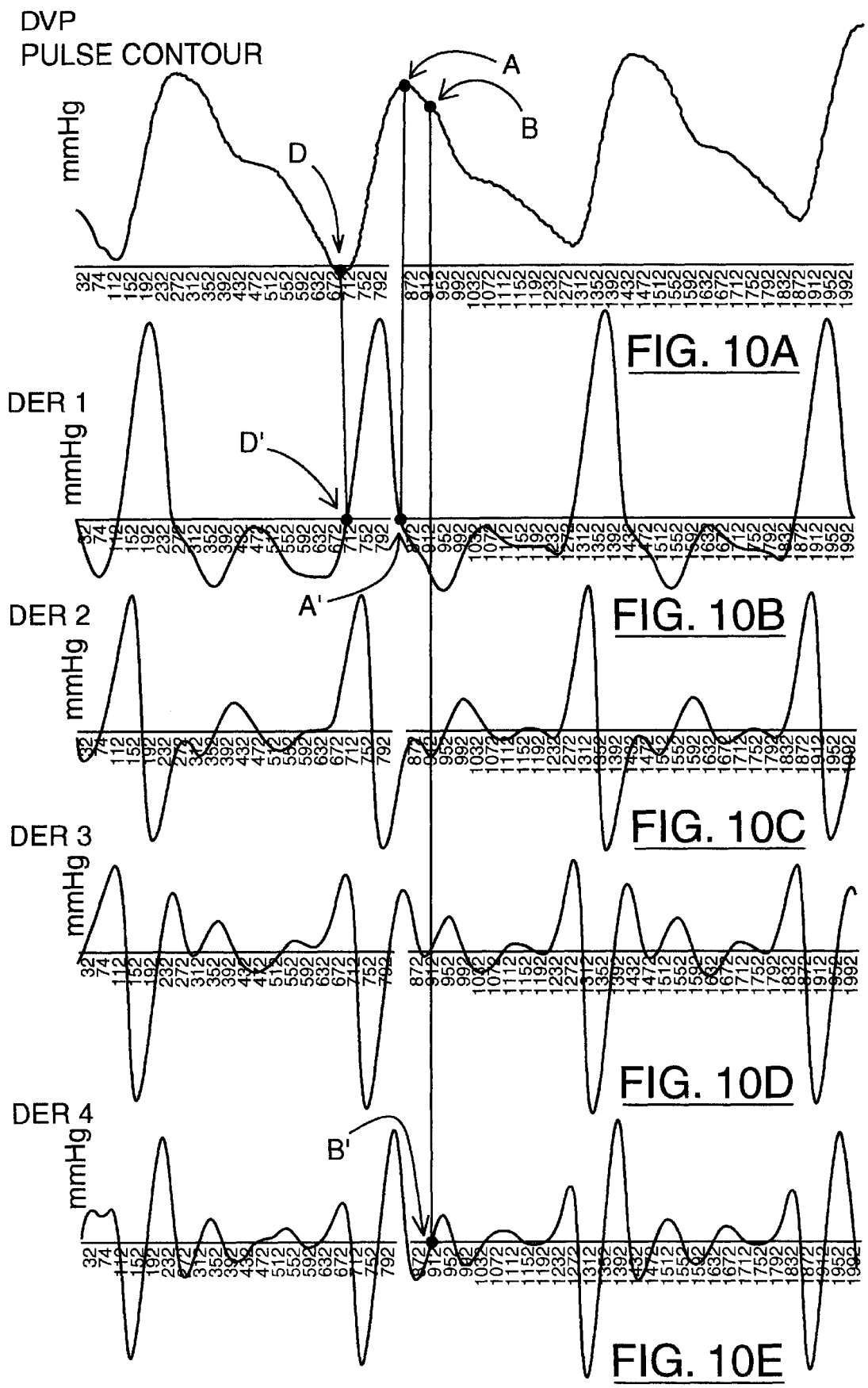

Spreadsheet A
|         | $T_1$ | $T_2$ | ··· | $T_N$ |
|---------|-------|-------|-----|-------|
| $BEAT_1$ | 0 | $A_{12}$ | ··· | $A_{1N}$ |
| $BEAT_2$ | 0 | $A_{22}$ |     | $A_{2N}$ |
| ⋮ | ⋮ | ⋮ | | ⋮ |
| $BEAT_M$ | 0 | $A_{M2}$ | | $A_{MN}$ |
| | ↑$SYNC_1$ | ↑$SYNC_1$ | | ↑$SYNC_1$ |
FIG. 12F
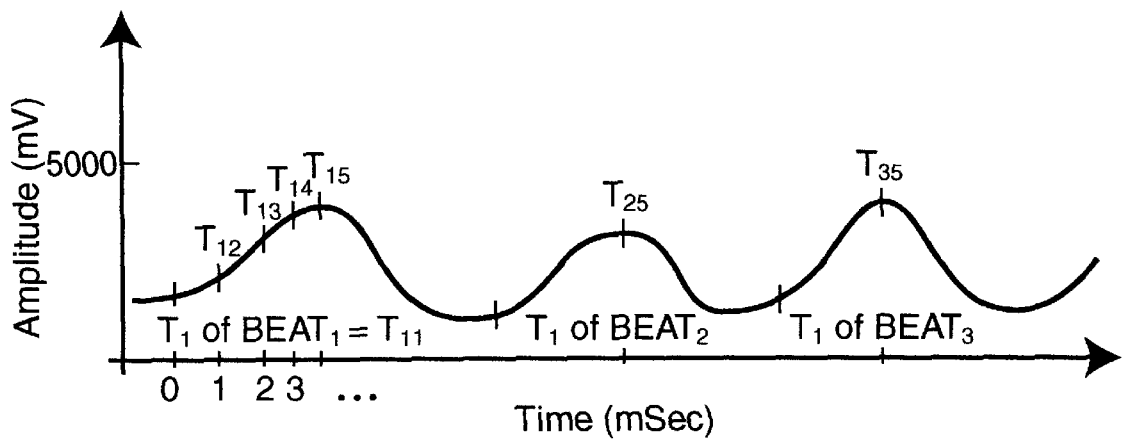
FIG. 12G
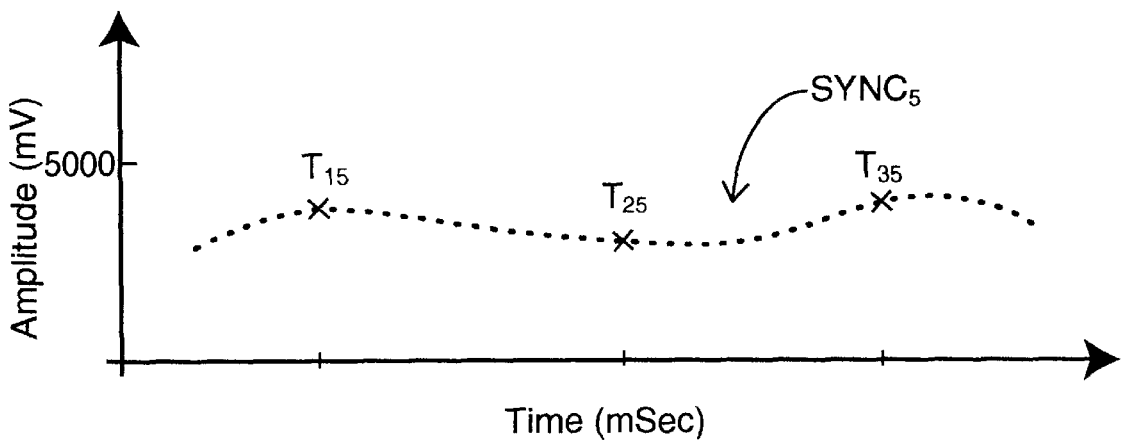
FIG. 12H

PHYSIOLOGICAL SIGNAL MONITORING SYSTEM

FIELD OF THE INVENTION

This invention relates to a physiological signal monitoring system and more particularly to a system which allows a user to determine various types of physiological information and which allows a user to electronically access this information over a communication network.

BACKGROUND OF THE INVENTION

Various types of instrumentation for monitoring physiological signals are currently available to consumers and health professionals. Specifically, consumers have access to thermometers, weight scales, blood pressure cuffs, blood glucose monitors, urine testing strips and other similar diagnostic technology. In the field of cardiovascular physiological testing, there is currently a wide variety of blood pressure testing equipment which has been developed to determine arterial blood pressure related parameters, namely systolic pressure (maximum blood pressure) and diastolic pressure (minimum blood pressure). It has also been recognized that other parameters such as mean (average) blood pressure during a heart cycle, pulse pressure (the difference between systolic and diastolic pressure) as well as pulse rate and pulse rhythm are also important in assessing patient health.

In an attempt to provide consumers and health professionals with non-invasive blood pressure measuring equipment for patient safety and convenience, photoplethysmograph (PPG) sensors have been utilized within blood pressure testing equipment. PPG sensors are well-known instruments which use light for determining and registering variations in a patient's blood volume. They can instantaneously track arterial blood volume changes during the cardiac cycle and are used within physiological signs monitoring devices.

One such device is disclosed in U.S. Pat. No. 6,047,203 to Sackner et al. which uses PPG sensors to monitor the physiological signs of the user to identify when adverse health conditions are present within the user and to provide the user with appropriate directions or signals. However, many devices such as this one are only used to determine whether physiological signals indicate the presence of an adverse condition for the user and are not directed to identifying and/or determining accurate estimates of blood pressure and other cardiovascular values for diagnostic purposes.

Since PPG sensors operate non-invasively, efforts have been made to utilize them to determine estimates of mean, systolic and diastolic blood pressure. These devices either estimate mean blood pressure from the mean value of the blood volume pulse, a measure of pulse wave velocity or changes in the volume pulse contour using formulae and calibrated constants. However, these devices have not achieved widespread use due to a lack of accuracy and difficulty of use.

Specifically, the difficulties with estimation of mean, systolic and diastolic blood pressure from the volume pulse contour can be attributed to variability in the amplitude of the volume pulse contour due to volume changes unrelated to blood pressure effects and the nonlinear relationship between volume changes in an arterial vessel and associated pressure changes.

Also, there are measurement and instrumentation difficulties associated with PPG sensors such as the presence of mechanical alterations in the sensor/skin interface (i.e. vibrations and differing pressure), ambient light effects, and changes in the blood volume due to alteration in body position. Without carefully correcting for changes in the blood volume pulse signal that are due to factors other than blood pressure and without using conversion techniques which recognize the nonlinear relationship between arterial vessel volume and pressure, these methods cannot accurately predict blood pressure characteristics using PPG readings alone.

It has long been recognized that blood volume pulse contours change with aging and blood pressure. These changes are largely related to a shift in the occurrence of the aortic reflected wave within the pulse contour. The reflected wave is a complex pulse signal generated by reflections of the pulse wave originating at the heart. The pulse wave travels from the heart along the aorta with branches to the head and the arms, continues along the aorta to the trunk and from there to the legs. At about the level of the kidneys, a significant reflection of the pulse wave originates. The reflected waves from the arms and the legs are rapidly damped, travelling with relatively low amplitude back to the trunk. It is well known that as detected in the upper extremity the reflective wave originating in the abdominal aorta has an onset later than the reflected wave from the upper limbs, has significantly greater amplitude, travels almost without attenuation to the ends of the upper extremity, and has a significant presence in the volume pulse contour obtained from a fingertip, ear or other points on the surface of the body above the aortic origin of the reflecting wave.

By accurately characterizing the timing, amplitude and shape of the abdominal aortic reflected wave, a significant amount of information about aortic compliance, aortic pulse wave velocity and the health of the internal organs can be obtained. As discussed in "Wave Reflection in the Systemic Circulation and its Implications in Ventricular Function", Michael O'Rourke et al., Journal of Hypertension 1993, 11 pgs. 327–337, human aortic pulse wave velocity more than doubles between 17 and 70 years of age. This phenomenon is a manifestation of arterial stiffening and is attributable to the fatiguing effects of cyclic stress causing fracture of load-bearing elastic lamellae in the wall, and degeneration of arterial wall. When mean blood pressure is decreased (i.e. using vasoactive drugs), the reflected wave has been observed to occur later in the pulse wave, whereas when blood pressure is increased, the reflected wave occurs earlier and moves into the systolic part of the wave. Readily observed ascending aortic pressure wave contours associated with ageing and hypertension can be explained on the basis of early wave reflection. Also, several authorities have observed a strong association between poor aortic compliance (i.e. arterial stiffness) and coronary artery disease and hypertension. For example, it has been observed that decreased aortic compliance results in an increase in systolic and a decrease in diastolic aortic pressure, both of which are deleterious to the heart ("Aortic Compliance in Human Hypertension", Zharorong Liu, et al., Hypertension Vol. 14, No. 2, August 1989 pgs. 129–136). Accordingly, the aortic reflected wave is a powerful source of information relating to a user's cardiovascular health and relative risk.

While there are several techniques for utilizing the timing of the aortic reflected wave to derive physiologically useful parameters, the analysis used by most of these techniques does not accurately identify the onset of the reflected wave in the volume pulse contour. The subtle changes in the volume pulse signal associated with aortic reflection effects that follow the systolic peak are difficult to visualize. It is often extremely difficult to identify these effects, even with the help of computing means, without time consuming pattern recognition techniques.

For example, U.S. Pat. No. 5,265,011 to O'Rourke discloses a method for determining the systolic and diastolic pressures based on the specific contours of pressure pulses measured in an upper body peripheral artery. The method identifies pressure pulse peaks relating to systolic and diastolic components of the pulse contour and takes first and third derivatives of the pressure pulses to determine relevant minimum and maximum points. Specifically, the onset of the systolic pressure wave is determined by locating a zero crossing from negative-to-positive on a first derivative curve and the shoulder of the reflected wave is identified by finding the second negative-to-positive zero crossing on the third derivative. However, it is difficult in practise to identify the reflected wave peak in this fashion as the slope changes of the third derivative do not consistently indicate the reflected wave peak. In addition, this method identifies only slope changes in the blood volume pulse contour. These slope changes are an indirect and imprecise way of characterizing the timing of the reflected wave component. The high degree of overlap between the systolic, reflected and dicrotic wave components obscures the characteristics of the reflected wave.

Also, many established methods that use PPG techniques and volume pulse contour analysis and/or pulse wave velocity to derive blood pressure do not adequately take into account other complicating effects. For example, the volume pulse contour varies with changes in blood volume that are unrelated to blood pressure. Changes in temperature, respiration and body position can all lead to changes in local blood volume. Movement of a finger relative to the sensor will also result in unreliable PPG readings. Unless these factors are controlled, erroneous blood pressure readings will result.

Various established methodologies such as the one disclosed in U.S. Pat. No. 5,876,348 to Sugo et al., derive blood pressure measures on the assumption that pulse wave velocity and blood pressure are linearly related. Specifically, in U.S. Pat. No. 5,876,248 mean blood pressure is derived using the formula $P = \alpha\, PWV + \beta$, where P is mean pressure, PWV is pulse wave velocity and $\alpha$ and $\beta$ are constants specific to a user. The formula $P = \alpha\, PWV + \beta$ assumes that the relationship between blood pressure and PWV is linear, which is incorrect. Although the increase in pulse wide velocity is linear for low pressures, authorities confirm that the increase is nonlinear with pressure above typical diastolic pressure ("Measurement of Pulse-Wave Velocity Using a Beat-Sampling Technique", J. D. Pruett, Annals of Biomedical Engineering, Vol. 16, pgs. 341–347). Further, the relationship between the excursion of the digital blood volume contour and the arterial pulse pressure is also nonlinear. Current volume pulse contour analysis techniques do not take these considerations into account and result in unreliable determinations.

Accordingly, there is a need for an improved physiological characteristic testing device which provides for improved estimation of various cardiovascular and respiratory indices through the correct identification of the aortic reflected wave and arterial blood pressure which facilitates improved communication of information and biofeedback functionality, uses a minimum of processing and memory capacity, comprises relatively few parts, and which is inexpensive to manufacture and operate.

BRIEF SUMMARY OF THE INVENTION

It is therefore an object of the present invention, to provide a physiological signal monitoring system comprising:

(a) a sensor adapted to come into skin contact with a user body part, for sensing a physiological characteristic of the user and for generating electrical signals which correspond to said physiological characteristic;

(b) first processing means operatively coupled to said sensor for receiving and converting said electrical signals into data, for computing a set of physiological parameters on the basis of said data, said processing means also being operatively coupled to a communication network for transmission of said physiological parameters over said communication network;

(c) display means coupled to said first processing means for displaying said physiological parameters; and (d) a server coupled to said communications network for receiving said physiological parameters from said processing means, for conducting analysis of said first physiological parameters, and for transmitting information related to said physiological parameters to said first processing means for display on said display means.

In another aspect the invention provides a method of monitoring the physiological signals of a user comprising the steps of:

(a) positioning a sensor in close proximity to a body part of the user for sensing a physiological characteristic of the user and for generating electrical signals which correspond to said physiological characteristic;

(b) receiving and converting said electrical signals into data and computing a set of physiological parameters on the basis of said data;

(c) displaying said physiological parameters to the user;

(d) transmitting said physiological parameters to a server over a communications network; and (e) analyzing said physiological parameters on said server and transmitting information associated with said physiological parameters to the user.

In another aspect the invention provides physiological signal monitoring system for determining a number of physiological parameters for a user, said monitoring system comprising:

(a) a PPG sensor adapted to come into skin contact with the user for obtaining the blood volume contour of the user;

(b) filtering means for filtering nonpulsatile and slowly pulsatile signals from the blood volume contour to obtain a filtered blood volume pulse signal; and (c) processing means for extracting a representation of the aortic reflected wave contour from the user's filtered blood volume pulse signal and for determining a plurality of physiological parameters based on characteristics of said aortic reflected wave.

In another aspect the invention provides a method of determining a number of physiological parameters for a user, said method comprising the steps of:

(a) obtaining the blood volume contour of the user using a first PPG sensor coupled to the user's body, said blood volume pulse contour containing a plurality of individual blood volume pulse contour pulses;

(b) filtering nonpulsatile and slowly pulsatile signals from the blood volume pulse contour to obtain a filtered blood volume pulse signal;

(c) extracting an estimate of the aortic reflected wave contour from the filtered blood volume pulse signal; and (d) determining a plurality of physiological parameters based on characteristics of said aortic reflected wave.

The invention also provides a method of determining the systolic and diastolic blood pressure of a user, in addition to the steps of determining a number of physiological parameters for a user described above, comprising the additional steps of:

(e) performing a series of calibration photolethsympographic measurements using said first PPG sensor coupled to the skin of the user over a predetermined calibration period of time;

(f) performing a series of calibration blood pressure measurements of the user using a blood pressure monitor coupled to the user over said predetermined calibration period of time;

(g) determining at least one transfer function which relates said calibration blood volume measurements and said calibration blood pressure measurements;

(h) calculating a synthesized blood pressure pulse contour, $RADIAL_{synth}$, mean arterial blood pressure, $MEAN_{ABP}$, and synthesized pulse pressure, $PP_{synth}$, by applying said at least one transfer function to various indices of said user's blood volume pulse contour obtained from step (a);

(i) determining the pulse pressure of the synthesized blood pressure pulse contour, $PP\ RADIAL_{synth}$ from said synthesized blood pressure pulse contour, $RADIAL_{synth}$;

(j) calculating the mean amplitude of the synthesized blood pressure pulse contour, $RADIAL_{synth}$, namely, $MEAN\ AMP\ RADIAL_{synth}$;

(k) calculating the mean fractional amplitude, $MEAN\ AMP_{Frac}$, of said synthesized blood pressure contour, $RADIAL_{synth}$, according to the relation: $MEAN\ AMP_{Frac} = MEAN\ AMP\ RADIAL_{synth}/PP\ RADIAL_{synth}$; and (l) calculating systolic blood pressure, $BP_{sys}$, according to the relation: $BP_{sys} = MEAN_{ABP} + PP_{synth}(1 - MEAN\ AMP_{Frac})$.

In another aspect, the invention provides a method of determining the pulse wave velocity of a user, in addition to the steps of determining a number of physiological parameters for a user described above, comprising the additional steps of:

(e) performing steps (a) and (b) using said first PPG sensor coupled to said user's body at a first location a and a second PPG sensor coupled to said user's body at a second location b, to obtain a first filtered blood volume pulse signal at location a and a second filtered blood volume pulse signal at location b;

(f) high pass filtering said first and second filtered blood volume pulse signals;

(g) performing cross correlation to obtain the time delay between said first and second filtered blood volume pulse signals according to the relation:

$$CC(\tau) = \int_{-\infty}^{+\infty} V_a(t) V_b(t - \tau) dt$$

where $CC(\tau)$ is the cross correlation which depends on the time delay between two parameters $V_a$ and $V_b$; $V_a(\tau)$ and $V_b(\tau)$ are the corresponding values of the first and second filtered blood volume pulse signals at the two different sites on the user's body, a and b, at a time t, and $\tau$ is the time delay;

(h) estimating the travel path for the user; and (i) estimating the user's pulse wave velocity on the basis of said time delay and said travel path.

In another aspect the invention provides a method for the extraction of a respiration contour from said blood volume pulse, in addition to the steps of determining a number of physiological parameters for a user described above, comprising the additional steps of:

(e) calculating an indicia based on said blood volume pulse contour that correlates with the mean blood pressure of the user;

(f) plotting the amplitude values of said indicia over time;

(g) interpolating said amplitude values over time to obtain an interpolated respiratory contour; and (h) low pass filtering the interpolated respiratory contour to obtain the respiration contour.

In another aspect the invention provides a method for temperature correcting a user's blood volume pulse contour, in addition to the steps of determining a number of physiological parameters for a user described above, comprising the additional steps of:

(e) artificially lowering the temperature of the user's finger prior to step (a) and conducting step (a) as said finger increases in temperature;

(f) determining the amplitude of the blood volume pulse contour and the amplitude of the filtered blood volume pulse signal at a plurality of sample times, N;

(g) calculating the changes in amplitude of the blood volume pulse contour, $\Delta PPG$, and changes in amplitude of the filtered blood volume pulse signal, $\Delta DVP$, over said plurality of sample times, N;

(h) calculating a plurality of constants, $K_i$ for i=N−1 sample times where $K_i = \Delta PPG/\Delta DVP$;

(i) averaging the values of said plurality of constants $K_i$ to obtain temperature constant K; and (j) using said temperature constant K to calibrate readings of said filtered blood volume pulse signal by using the relation: $\Delta PPG = K \Delta DVP$.

In another aspect the invention provides a method of determining a correlate for said plurality of physiological parameters, in addition to the steps of determining a number of physiological parameters for a user described above, comprising the additional steps of:

(e) twice differentiating said filtered blood volume pulse signal to produce a second derivative;

(f) providing a horizontal axis for indicating time with said second derivative extending above and below said horizontal axis and located on the horizontal axis at the start of said second derivative for each pulse; and (g) determining the ratio of the height of the second peak above a first trough of said second derivative relative to the height of the horizontal axis above the first trough of said second derivative of said filtered blood volume pulse signal.

In another aspect the invention provides a manually operated user input device for simultaneously sensing a physiological characteristic of a user and for providing input of data unrelated to the physiological characteristic, said device comprising:

(a) a housing having a surface in at least intermittent contact with a portion of the user's finger;

(b) at least one PPG sensor disposed on said surface for sensing the physiological characteristic of the user; and (c) manually operated: means for inputting data to the user input device, said data unrelated to the physiological characteristic.

In another aspect the invention provides a device for removable attachment to an extremity of the body of a user, said device comprising:

(a) a housing having a surface in at least intermittent contact with a portion of the user's extremity;

(b) at least one PPG sensor disposed on said surface for sensing the physiological characteristic of the user; and (c) biasing means coupled to said housing for holding said portion of said extremity against said PPG sensor with constant and predictable pressure and for shielding said PPG sensors from ambient light.

Further objects and advantages of the invention will appear from the following description, taken together with the accompanying drawings.

BRIEF DESCRIPTION OF THE DRAWINGS

In the accompanying drawings:

FIG. 10A is a graph showing the DVP signal outputted by the user input device of FIG. 2;

FIG. 10B is a graph showing the first derivative of the DVP signal of FIG. 10A;

FIG. 10C is a graph showing the second derivative of the DVP signal of FIG. 10A;

FIG. 10D is a graph showing the third derivative of the DVP signal of FIG. 10A;

FIG. 10E is a graph showing the fourth derivative of the DVP signal of FIG. 10A;

FIG. 12F is a spreadsheet table A containing columns of amplitude data of the DVP beats at different sample times;

FIG. 12G is a spreadsheet table B containing columns of interpolated amplitude data of the DVP beats at different sample times;

FIG. 12H is a graph showing the result of interpolation using a polynomial curve fitting algorithm between sample data within each DVP beat of FIG. 12F;

DETAILED DESCRIPTION OF PREFERRED EMBODIMENTS

Figure 1:
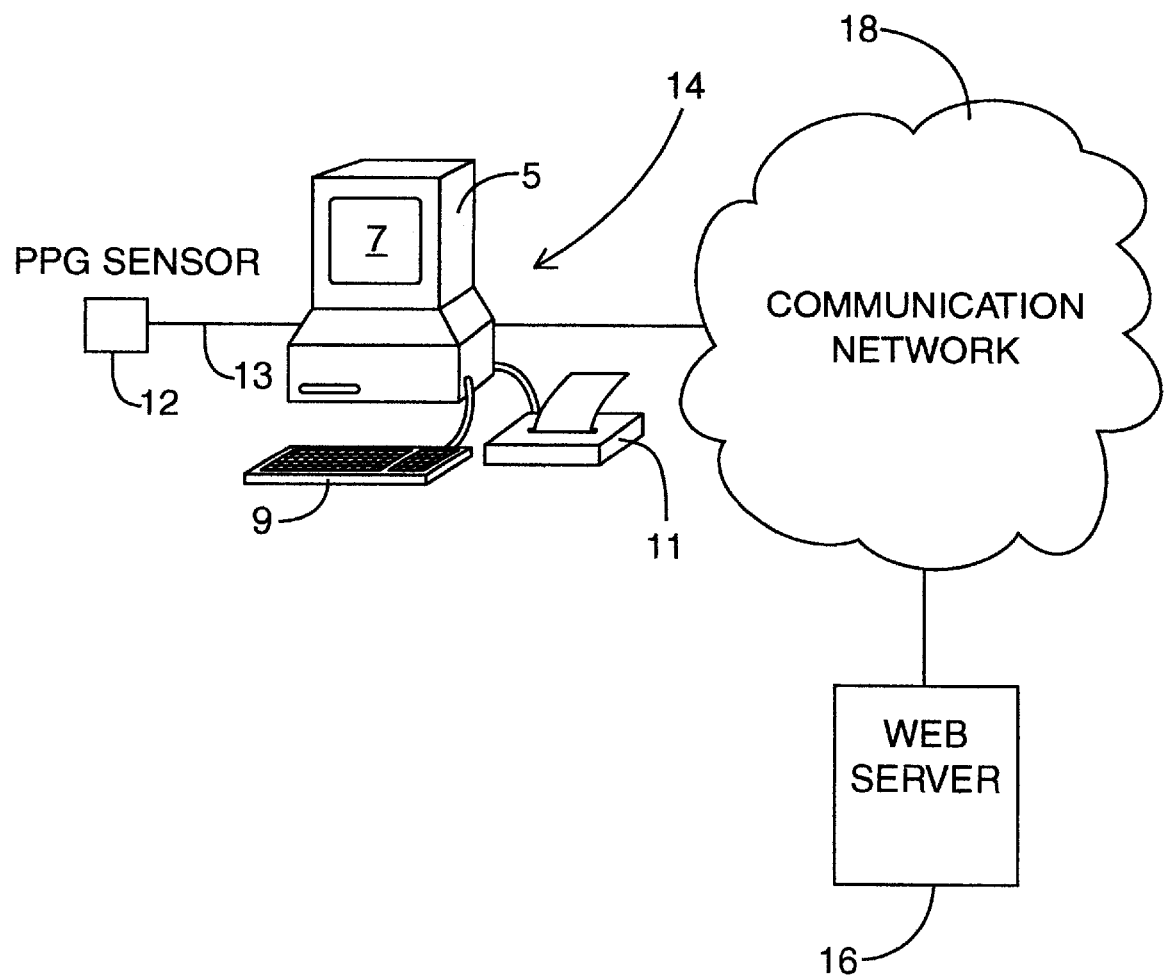
FIG. 1 is an illustration of the overall configuration of a physiological health monitoring system according to the present invention.

Reference is first made to FIG. 1, which shows the overall configuration of the preferred embodiment of a physiological monitoring system 10, according to the present invention. System 10 comprises a conventional plethysmography (PPG) sensor 12 coupled to a processing device 14 which is in data communication with a Web site server 16 through a communication network 18 (i.e. the Internet).

PPGs are well-known instruments which use light for determining and registering variations in a patient's blood volume. They can instantaneously track arterial blood volume changes during the cardiac cycle. PPG sensor 12 is installed within a computer mouse or some other computer peripheral (e.g. keyboard, touchpad, joystick) commonly associated with a computer processing device 14. It should be understood that it would be also possible to implement the invention by incorporating PPG sensor 12 within the casing of a personal digital assistant (PDA) or within some other type of stand alone data processing and transmitting device (e.g. a watch) or simply as a stand alone sensor device.

Processing device 14 is preferably a conventional personal computer having a central processing unit (CPU) 5, display 7, keyboard 9 and printer 11. Processing device 14 also preferably has a standard Universal Serial Bus (USB), sufficient memory and processing power to run the application programs associated with system 10, and a data transmission controller for sending and receiving data over data transmission cable 13, all built integrally with processing device 14. An executable program is installed within the permanent memory of processing device 14 to instruct the user through interactive menus to utilize the PPG sensor 12 such that proper PPG signals can be obtained from the user and to provide the user with his/her own generated physiological information through graphical means. It should be understood that such an executable program could also be available for downloading online from Web site server 16. The executable program has the functionality to allow a user to observe his/her own physiological signals in real time such that biofeedback is facilitated. Also, it is contemplated that processing device 14 could be used to store a user's physiological signals for later retrieval, comparative and display purposes. Commercially available signal measurement and analysis display software such as LabVIEW™ (available from National Instruments of Austin, Tex.) is utilized to perform the necessary data analysis as well as display the results of the calculations in easy to understand format. It should be understood that processing device 14 could just as easily be a PDA, as discussed above.

Web site server 16 is a conventional server having sufficient memory and processing speed to handle the input, storage and manipulation of large volumes of data being simultaneously transmitted from a plurality of processing devices 14. Web site server 16 also must also be capable of transmitting additional relevant data back to user's computer 14 over communication network 18 for display on a user's processing device 14. Web site server 16 also provides encrypted and password protected secure storage of a user's physiological signals along with any other health documentation that the user may desire to store at the Web site. Web site server 16 could also allow for the storage and restricted access to a plurality of user's physiological signals (submitted on an anonymous basis) and associated health documentation for anonymous medical research purposes.

Figure 2:
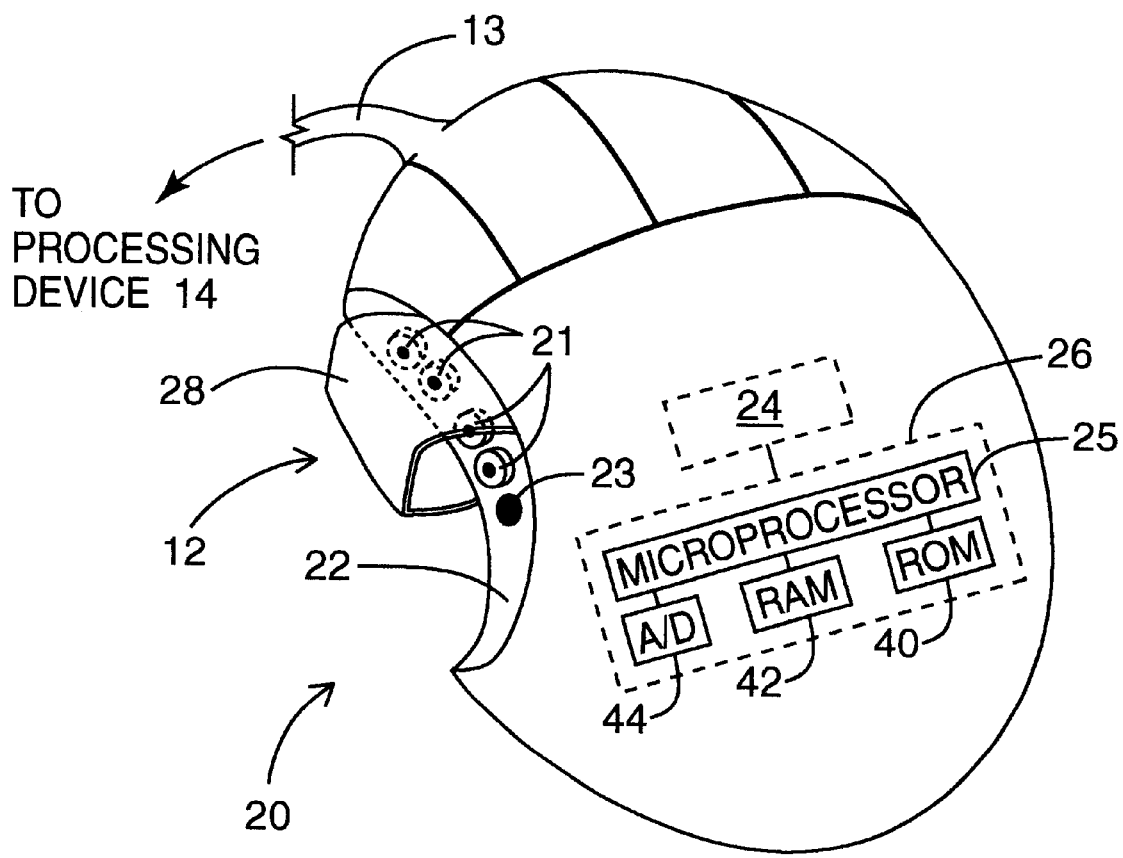
FIG. 2 is a more detailed illustration of the PPG sensor of FIG. 1 implemented within a user input device.
Figure 3:
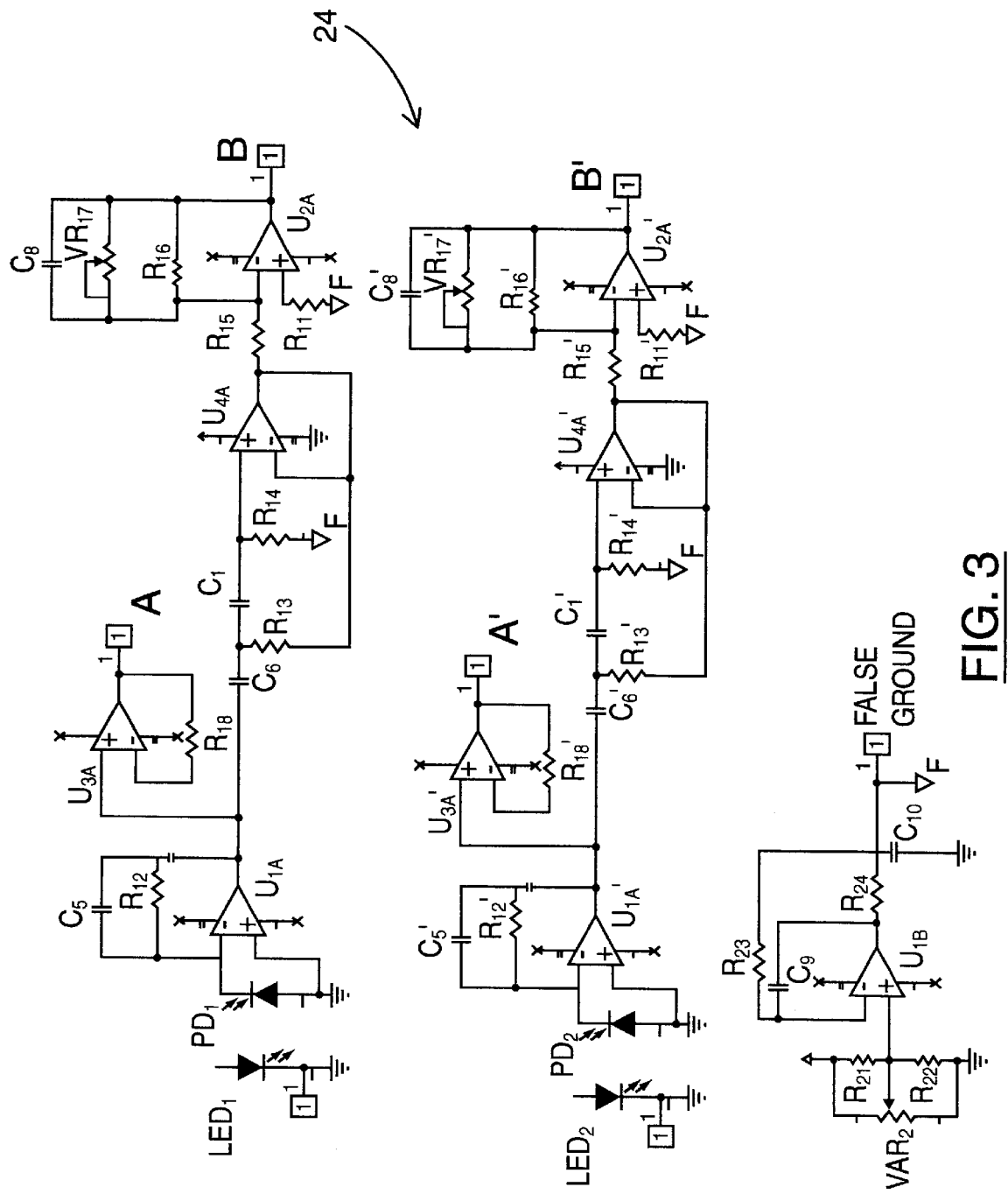
FIG. 3 is a circuit diagram of the PPG sensor and the signal conditioning module of FIG. 2.

Referring now to FIGS. 2 and 3, PPG sensor 12 is shown installed within a user input device 20 which is coupled to processing device 14 through data transmission cable 13. In addition to PPG sensor 12, user input device 20 comprises a thermistor 23 positioned in close proximity to PPG sensor 12, a signal conditioner module 24 to condition the raw PPG signal, and a microcontroller 26 to control the operation of user input device 20.

PPG sensor 12 has a relatively small footprint (e.g. few square centimeters) and is implemented using a red $LED_1$ and an infrared $LED_2$, each associated with a photodiode $PD_1$ and $PD_2$ (FIG. 3) in a known configuration for reflective mode operation (i.e. light is transmitted into a body part and the amount of light reflected back is detected). The emitted monochromatic light emitted from $LED_1$ and $LED_2$ travels through a user's finger along a light path which passes through blood in a plurality of arteries as well as background tissue. As the monochromatic light travels along its light path it is partially absorbed by the background tissue and the blood. A portion of the monochromatic light is not absorbed and is reflected back to the appropriate photodiode PDor $PD_2$. As is conventionally known, reflective mode PPG uses the reflected light from a site to estimate absorption of light and to generate a raw blood volume pulse contour signal. The detector is positioned on the same side as the radiating LED in order to detect the reflected light.

Also, as shown in FIG. 2, PPG sensor 12 utilizes cylindrical baffles 21 to house $LED_1$ and $LED_2$ and photodiodes $PD_1$ and $PD_2$ to prevent direct coupling of light from the LED's to the photodiodes. When a user's finger is placed over the top openings of baffles 21, light will be only provided to the finger and spillover light will be appreciably reduced. Well known techniques to accomplish motion artifact reduction such as that discussed in PCT Pat. Application No. 99/32030 to BTG International Limited could be utilized to further reduce the amount of motion artifact related distortion of the PPG signal.

It should be understood that PPG sensor 12 could also be adapted to operate in transmission mode (i.e. where light is transmitted through a body part and the amount of light transmitted through is detected) by making the appropriate changes to the way PPG sensor 12 is attached a user's finger.

The particular user input device 20 shown is formed out of a rigid plastic material and operates as a conventional computer mouse as well as a diagnostic input tool for detecting a blood volume contour from a user's finger. Thus, user input device 20 independently receives and sends to processing device 14, data input from the user which is unrelated to the blood volume contour. User input device 20 has a depression 22 formed within its housing that is shaped to receive a user's thumb (a right handed model is shown) and an elastic restraint 28 is secured on either side of depression 22.

PPG sensor 12 is installed within the housing in depression 22 such that PPG.sensor 12 is positioned underneath the part of depression 22 that corresponds to a user's distal thumb and so that a user's thumb when positioned within depression 22 would be completely covered by; an elastic restraint 28. It has been determined that this is an optimal configuration, since the transmitted light can penetrate adequately into the skin at a user's fingertip and due to the fact that elastic restraint 28 shields PPG sensor 12 from ambient light. For convenient operation within user input device 20, the LED and photodiode pairs are installed within depression 22 approximately one centimeter apart from each other.

It is known that the movement of the finger relative to the sensor element will corrupt data from the sensor. It is necessary to restrict finger motion in a way that decreases motion while at the same time does not impeded arterial flow or prevent venous flow. Elastic restraint 28 decreases movement of the thumb relative to the sensor and applies a constant and predictable biasing force that presses the thumb against PPG sensor 12. The use of elastic restraint 28 which is adapted to gently but securely bias the finger against the PPG sensor 12 helps to recreate the same pressure of a user's finger against PPG sensor 12 and to ensure that the change in the PPG signal pulse obtained from the finger due to blood pressure changes will be consistent from one use of system 10 to another. The time multiplexed output current from the photodiodes $PD_1$ and $PD_2$ and the thermistor 22 (FIG. 3) is then applied to signal conditioner module 24.

FIG. 3 shows the circuity of signal conditioner module 24. Signal conditioner module 24 uses two identical conditioning circuits to condition the current output of photodiodes $PD_1$ and $PD_2$ independently. The operation of the circuit which conditions the current signal of photodiode $PD_1$ will be discussed, but it should be understood that the circuit which conditions photodiode $PD_2$ operates identically. The components of the circuit which conditions the current signal output of photodiode. $PD_2$ are identified with the same reference numbers as for the circuit for photodiode $PD_1$, but with the part numbers primed.

Each circuit includes operational quad amplifiers U1A and U2A fabricated on a single IC (e.g. Texas Instruments brand TLC274 Precision Quad Operational Amplifier) as well as capacitors $C_1$, $C_5$, $C_6$, and $C_8$, resistors $R_{11}$, $R_{12}$, $R_{13}$, $R_{14}$, $R_{15}$, $R_{16}$, and $R_{18}$ and variable resistor $VR_{17}$. The operational amplifier $U_{1A}$, $PD_1$, $C_5$ and $R_{12}$ form a transimpedance photodetector circuit. The raw PPG photo current signal generated by $PD_1$ is converted to a voltage signal through resistor $R_{12}$. The combination of capacitor $C_5$ and resistor $R_{12}$ provides low pass filtering for the raw PPG voltage signal generated at the output of operational amplifier $U_{1A}$ (at node A in FIG. 3). This configuration eliminates high frequency noise and high frequency spurious signals which may be present at the input to U1A.

The output of operational amplifier $U_{1A}$ follows two signal paths. The first path connects the raw PPG voltage signal to a unity gain buffer circuit comprised of operational amplifier $U_{3A}$ and resistor $R_{18}$. The raw PPG voltage signal can be simultaneously monitored or utilized by system 10 (at point A in FIG. 3) as will be discussed, while the raw PPG voltage signal is further processed by the second path in the circuit to produce a conditioned PPG voltage signal (at point B in FIG. 3).

The second path in the circuit (FIG. 3) connects the raw PPG voltage signal to a series of signal conditioning stages. The first conditioning stage is a 'Sallen and Key' high pass filter. This filter is comprised of capacitors $C_6$ and $C_1$, resistors $R_{13}$ and $R_{14}$ and operational amplifier $U_{4A}$. The values of capacitors $C_6$ and $C_1$ and resistors $R_{13}$ and $R_{14}$ are chosen to provide the high pass filter with a corner frequency of approximately 0.1 Hertz. The purpose of this filtering stage is to suppress low frequency noise within the PPG voltage signal.

Following this filtering process, the PPG voltage signal is applied to a combined amplifier and low pass filter stage comprised of resistors $R_{15}$, $R_{11}$, and $R_{16}$, variable resistor $VAR_{17}$, capacitor $C_8$ and operational amplifier $U_{2A}$. The gain of the amplifier is set by adjusting variable resistor $VAR_{17}$. The values of resistors $R_{16}$, $R_{17}$ and capacitor $C_8$ determine the corner frequency which is typically 30 Hertz. The conditioned PPG voltage signal generated by this stage (at point B) is provided to the processing device 14. In this way signal conditioner module 24 improves the signal to noise ratio of the PPG signal prior to digitization.

In order to power both the high pass filter and combined amplifier and low pass filter stage discussed above from the Universal Serial Bus of processing device 14, it is necessary to provide these circuits with a false ground as is conventionally known. The false ground circuit is comprised of variable resistor $VAR_2$, resistors $R_{22}$, $R_{21}$, $R_{23}$, capacitors $C_9$, $C_{10}$ and operational amplifier $U_{1B}$. The false ground circuit is a low impedance circuit which can respond quickly to changes in input current. By adjusting the variable resistor $VAR_2$, the ground reference can be shifted between zero and 5 volts DC. By shifting the ground reference level, the conditioned PPG voltage signal can be DC shifted accordingly.

Accordingly, the PPG voltage signal from photodiodes $PD_1$ and $PD_2$ is converted into conditioned PPG voltage signals at outputs at nodes B and B', respectively. These conditioned PPG voltage signals are provided to microcontroller 26 for digitizing and analysis.

Microcontroller 26 (FIG. 2) may be any commercially available programmable device such as a Mitsubishi USB microcontroller (available from Mitsubishi Semiconductors, Inc. of Japan), although it should be understood that any type of logic circuit with similar operating functions (particularly one which has a USB interface and which includes an on-board analog-to-digital converter) can be utilized. Storage of program instructions and other static data is provided by a read only memory (ROM) 40, while storage of dynamic data is provided by a random access memory (RAM) 42. Both memory units 40 and 42 are controlled and accessed by microprocessor 25. On board analog-to-digital converter A/D 44 (10 bit, 5 channel input) is used to convert the conditioned PPG signals at B and B' into time sampled digital signals which are then provided to processing device 14. Also, all of the circuitry of signal conditioner module 24 is provided with a 5 volt source from the USB line of microcontroller 26.

Microcontroller 26 is also programmed to control the operation of $LED_1$ and $LED_2$ of PPG sensor 12 for optimal sensor operation. Microcontroller 26 is programmed to generate digital switching pulses to drive $LED_1$ and $LED_2$ of PPG sensor 12 alternately at a repetition rate of 1 KHz (i.e. each LED accomplishes sampling at a rate of 1 KHz). It has been determined that the sampling frequency should be 10 times the highest frequency of interest. The conditioned PPG signal has frequency components as high as 30 Hertz. However, 60 Hertz noise from electrical sources in the environment necessitates sampling of the signal at a high enough rate to ensure the effectiveness of the associated noise filtering software of CPU 5.

By driving $LED_1$ and $LED_2$ alternately, it is ensured that only one LED is turned on at any one time so that the light signals are isolated from each other's photodiode. Also, both $LED_1$ and $LED_2$ are periodically turned off to acquire a signal used to correct for ambient light effects. Specifically, ambient light effects are eliminated through subtraction of the signal generated when the applicable $LED_1$ or $LED_2$ is off. Finally, the presence or absence of a finger on PPG sensor 12 can be determined by turning on an LED for a brief period at a regular time interval and determining whether the associated photodiode detects any reflected light. This polling activity allows PPG sensor 12 to be active only when necessary.

Thermistor 23 allows system 10 to specify the absolute temperature at the skin surface. This additional information allows for greater accuracy in correction of blood volume pulse contour amplitude variations which are connected with temperature changes, as will be discussed. An indirect measure of temperature is obtained from the relationship between the amplitude of both the raw PPG output and the blood volume pulse contour. The thermistor allows more exact correlation. Such corrections will allow for more accurate determinations of systolic and diastolic blood pressures from the derived pressure pulse contour. As an additional feature, system 10 allows the user to have a display of the room ambient temperature on display 7 of processing device 14 at times when the user's finger is not in contact with thermistor 23.

User input device 20 generally requires a small number of inexpensive and commonly available components. Also, since microcontroller 26 includes a USB interface, it is possible to power user input device 20 completely from the computer processing device 14 for additional space savings and product cost economy.

Figure 4:
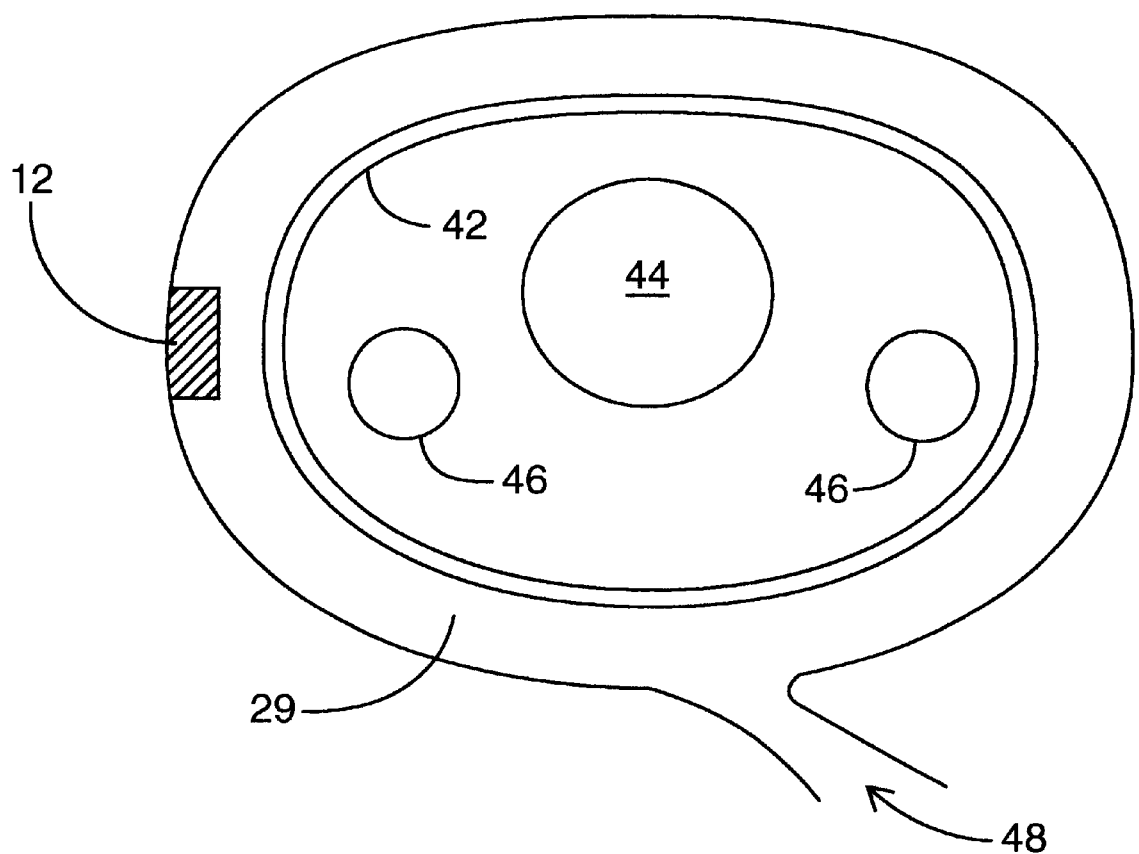
FIG. 4 is an illustration of an alternative embodiment of the PPG sensor of FIG. 1.

FIG. 4 shows an improved alternative to elastic restraint 28 which can be used to force a finger into contact with PPG sensor 12. A conventional gas filled finger cuff bladder 29 within which PPG sensor 12 is implanted, is shown surrounding the finger in a circumferential manner. The epidermis 42, bone 44, and arteries 46 of a finger are shown enveloped within cuff bladder 29 that is pressurized by a gas supply 48. The pressure of the gas within the bladder can be monitored and used by microcontroller 24 in association with pulse contour analysis data to more accurately predict absolute values for blood pressure.

Specifically, the conventionally known 'unloading' technique described by J. Penáz in U.S. Pat. No. 4,869,261 to Penaz et al. and used commercially in the Finapres system manufactured by Ohmeda involves the measurement of the size of the artery 46 when the blood pressure within it is the same as the external pressure imposed by the inflatable cuff bladder 29 that has been placed around the finger. Processing device 14 will then compute blood pressure measures based upon the PPG signal and upon the pressure in the cuff bladder 29 while the artery is maintained in an unloaded condition. In this way, the systolic, mean and diastolic pressure can all be determined.

Figure 5:
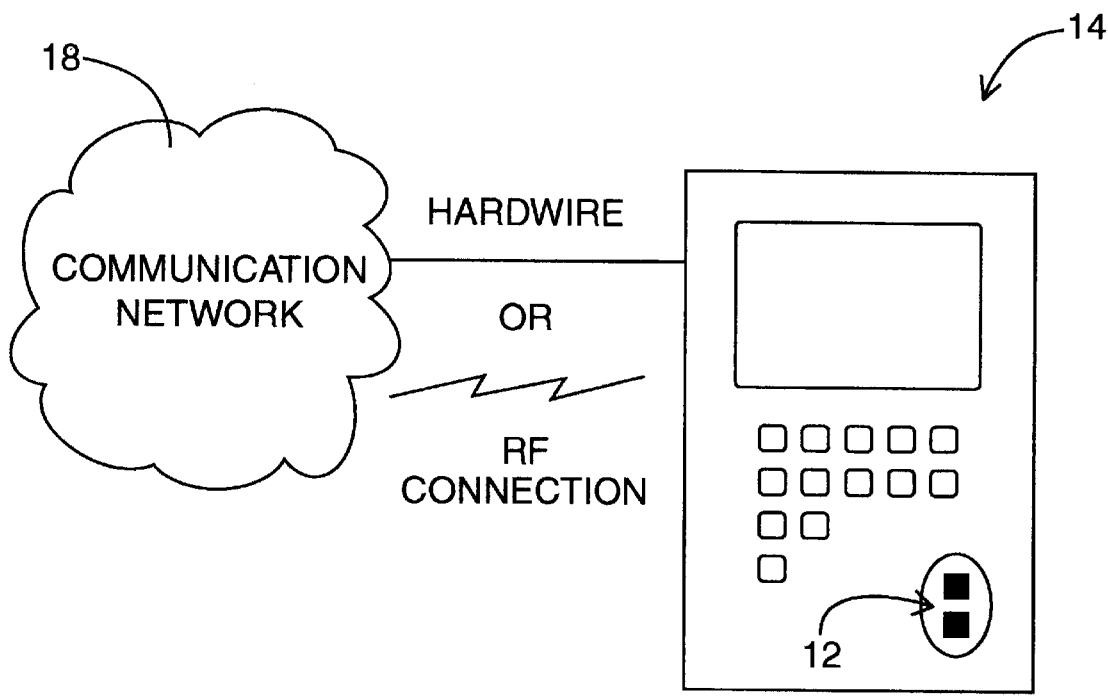
FIG. 5 is an illustration of an alternative embodiment of the user input device and the user's computer as a stand-alone personal digital assistant (PDA)

FIG. 5 shows another possible configuration of system 10 wherein processing device 14 is a PDA (e.g. Palm Pilot™) having PPG sensor 12 interfaced therein. PPG sensor 12 could be directly integrated into the shell of the PDA processing device 14. Alternatively, PPG sensor 12 could be implemented within a PDA accessory card or device, or adapted to interface with the PDA processing device 14 as an external wearable device. In the latter case, it would be possible for a user to wear a wearable user input device 12 such that blood volume pulse signal information could be collected by the PDA processing device 14 over the course of a day. It would be possible to arrange for periodic download of recorded volume pulse contour signal information collected by user input device 12 to processing device 14 and/or to Web site server 16 through processing device 14 over the communication network 18.

Further embodiments of the invention whereby PPG sensor 12 and processing device 14 are integrated together into a single unit with a compact design are also contemplated as processing speed and device memory increase as physical dimensions decrease. For example, it is likely that PPG sensor 12 and processing device 14, and all of its associated functionality, could feasibly be incorporated into a wrist watch device in the foreseeable future. It is contemplated that PPG sensor 12 could be integrated together with a computing means, wireless transmission means (e.g. well known convention radio frequency techniques as well as emerging radio frequency communication protocols such as the BlueTooth™ standard) and a battery in a small (e.g. 2 cm$^2$) component that would adhere to a body skin area for extended periods of time (e.g. weeks) and would transmit data to a remote computing device on a continuous basis.

Figure 6:
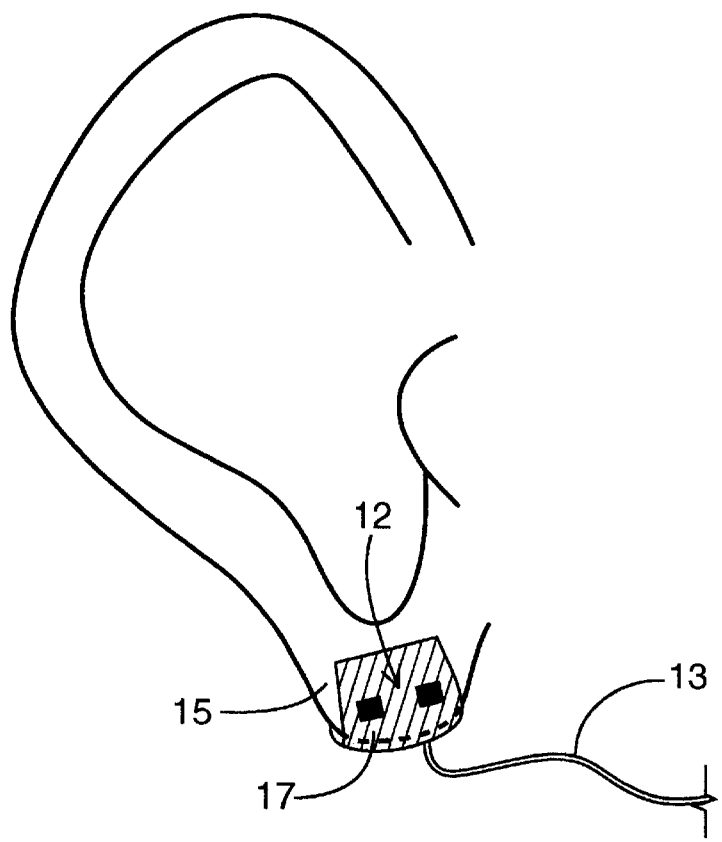
FIG. 6 is an illustration of an alternative embodiment of the user input device of FIG. 1.

FIG. 6 shows how PPG sensor 12 could be associated with the user's earlobe 15 instead of the user's finger. As discussed, it is well known that the reflective wave originating in the aorta has a significant presence in the volume pulse contour obtained from a fingertip, ear or other points on the surface of the body. As is conventionally known, the volume pulse signal acquired from the ear lobe, like the finger, is similar to that acquired from the carotid artery. Specifically, it is contemplated that PPG sensor 12 operating in transmission mode could be implanted in a "clip" device 17 which would provide for skin contact between PPG sensor 12 and a user's earlobe 15. This embodiment would provide analogous pulse volume signal information from which various cardiovascular and respiratory indices could be obtained, while allowing for hands free functionality.

It should also be understood that PPG sensor 12 can also consist of a single LED for reasons of product economy. However, while such a configuration can be used to determine a number of useful cardiovascular indices based on a time analysis of a single pulse waveform, it does not allow for the determination of other useful physiological signals, such as blood oxygen saturation, as will be described.

It should be understood that the light emitter(s) in PPG sensor 12 could also be a laser diode, which have the advantage of producing a well collimated beam of light. This characteristic would be advantageous to system 10 when measuring the time it take a pulse signal to travel from one light source to the next. With narrower beams of light, the photosensing elements are able to resolve the signals from each light source with greater precision. Also, while it is preferred to operate PPG sensor 12 in reflective mode, it would be possible to operate PPG sensor 12 in the transmission mode by making suitable alterations to the sensor's configuration.

Figure 7:
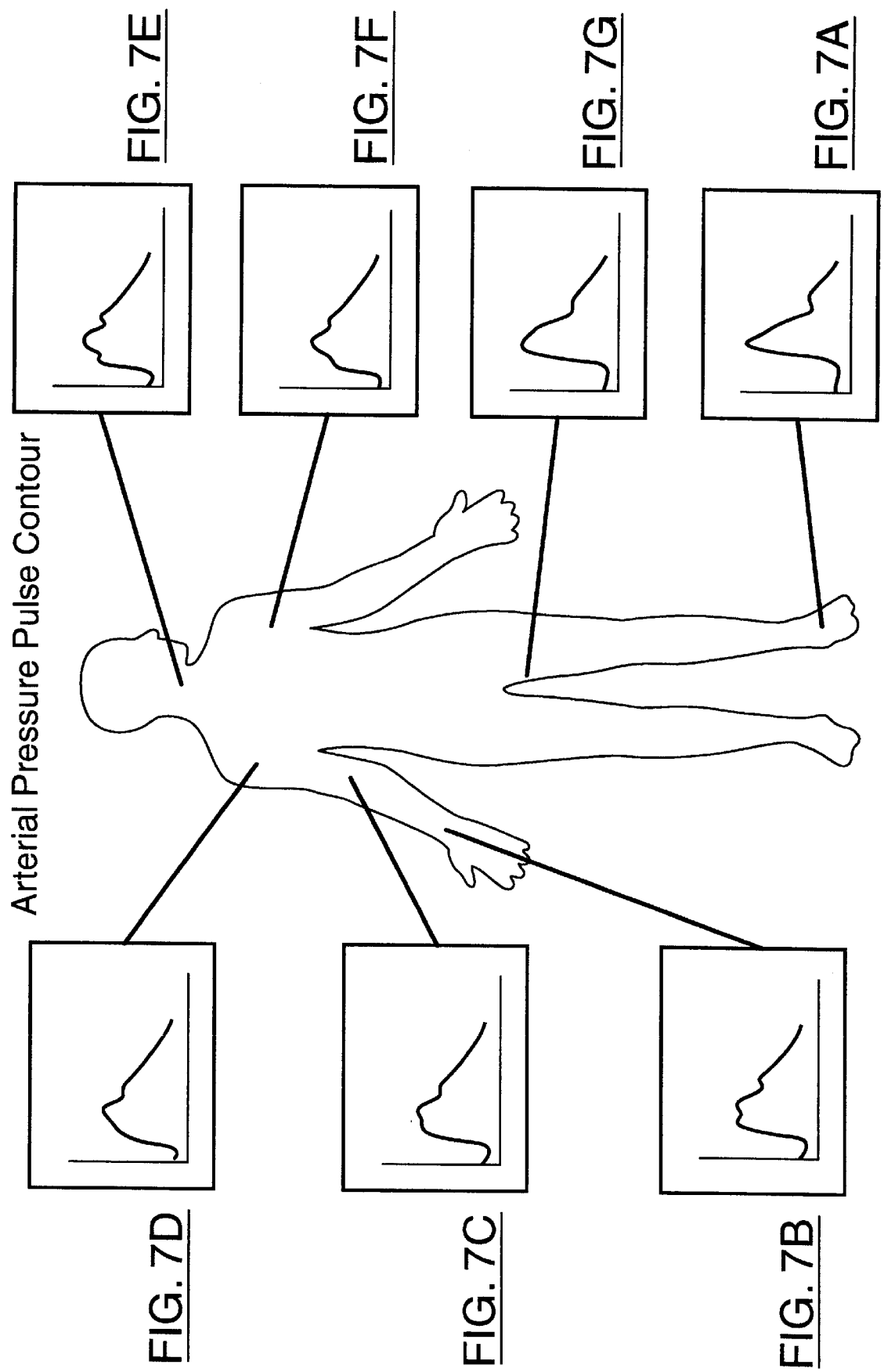
FIGS. 7A to 7G are illustrations of the variation of shape of the volume pulse signal contour at different points in the human body.

FIG. 7A to FIG. 7G illustrate the striking variation in shape of the arterial pressure pulse contour as measured throughout the human body. As shown in FIG. 7A, the arterial pulse contour obtained from the foot is almost completely lacking the additional peak originating from the effects of the reflected wave as seen at the wrist as shown in FIG. 7B. FIG. 7C shows the contour at the brachial artery, FIG. 7D shows the contour at the auxiliary artery, FIG. 7E shows the contour at the carotid artery, FIG. 7F shows the contour at the axillary artery and FIG. 7G shows the contour at the femoral artery. The differences in the contour of the pulse wave at different points of the human body is due to both changes in the impedance of the arterial tree and because of the effects of reflected waves.

As the heart contracts, a volume of blood is ejected into the aorta, the large artery leading from the heart. The elastic walls of the aorta expand in response to the volume of blood introduced. A wave is initiated in the walls of the aorta by this expansion. This wave in the walls of the aorta travels about ten times faster than the blood itself. This wave travels down the arterial 'tree' as the aorta branches and divides into smaller and smaller arterial vessels until reaching the capillaries. This wave produced by contraction of the heart is generally called the systolic wave. A second pulse wave emanates from the heart with the forceful closure of the aortic valve. As this valve closes, the rebounding valve leaflets create a wave termed the dicrotic wave. The systolic and dicrotic waves are referred to as primary pulse waves.

The primary pulse waves are partially reflected when they encounter areas of impedance mismatch in the arterial system, and the reflected waves travel back towards the heart. These areas of impedance mismatch can arise through branching, changes in diameter or elasticity of an arterial vessel. The systolic and dicrotic waves both produce a set of reflections that propagate through the arterial system, namely the systolic and dicrotic reflected waves. Reflected waves generated in the extremities are rapidly damped as they progress from smaller to larger blood vessels. Reflected waves generated in the aorta, especially the abdominal aorta are able to travel in a retrograde fashion without significant damping. The abdominal aorta at the level of the kidneys serves as an important reflecting site and produces systolic and dicrotic reflected waves. The abdominal aortic reflected waves appear prominently in the blood volume pulse contour as observed in locations above the abdominal aortic reflection site.

In addition to the reflected waves originating in the abdominal aorta, wave reflections occur at the entrance to the head circulation and in the small blood vessels within the fingertip, earlobe and other potential sensing sites. It is possible to differentiate between the reflected waves of differing origin because of the difference in time each takes to reach a certain location and the differing amplitudes of the reflected waves.

The characteristics of the aortic reflected wave are strong indicators of cardiovascular health. The speed with which the aortic reflected wave travels along the aorta varies with changes in aortic compliance and blood pressure, both of which also affect aortic pulse wave velocity. The aortic reflected wave travels more quickly as blood pressure increases and as aortic compliance decreases. It is also noteworthy that blood pressure and aortic pulse wave velocity rise and fall with respiration. Accordingly, by appropriately analyzing the aortic reflected wave, it is possible to obtain cardiovascular and respiratory information about an individual user, as will be discussed.

Figure 8:
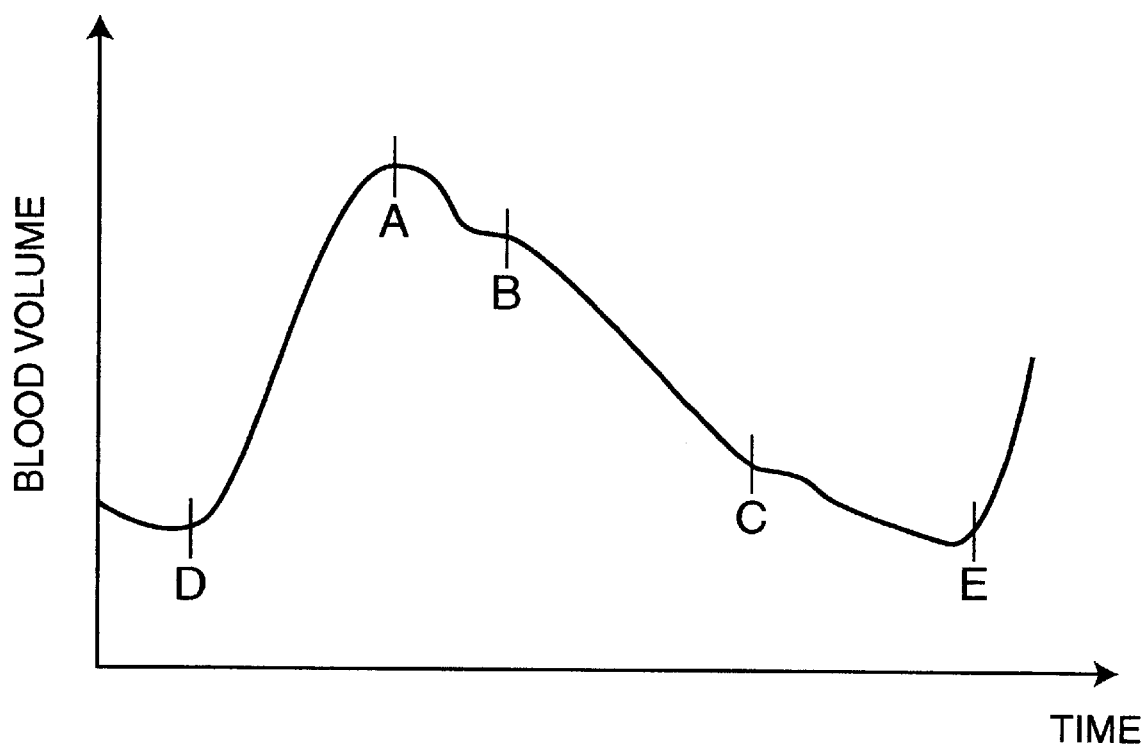
FIG. 8 is a graph of a typical DVP signal contour obtained from the fingertip of a user by user input device of FIG. 2.

FIG. 8 is a plot of a typical conditioned PPG pulse contour signal received by processing device 14 from the user input device 20. As illustrated, the PPG pulse contour consists of three peaks, namely a peak representing the systolic maximum (A), the reflected wave maximum (B), and the dicrotic notch (C) which represents the aortic valve closure. The PPG pulse contour also consists of the upstroke point (onset of systole at D) and end diastole (E).

Typically, it is not so easy to identify these various characteristic points (e.g. reflected wave maximum) from the PPG pulse contour signal on the basis of visual inspection alone. This is due to the fact that the interaction between primary and reflected waves obscures PPG wave detail preventing clear extraction of accurate timing and amplitude relationships between the primary and reflected waves. In order to extract the signal related to the aortic reflected wave from the raw PPG signal, several processing steps must be followed.

The raw PPG signal is affected by all factors which determine tissue blood volume. Because the arterial pulse wave, of which the aortic reflected wave is a component, originates from arterial blood vessels, it is necessary to isolate the signal originating from arterial blood vessels. This signal is rapidly pulsatile, relative to other physiological signals contained in the raw PPG signal. There are less rapidly pulsatile signals such as respiratory related cyclic volume changes, temperature related volume changes, autonomic nervous system induced changes in blood vessel tone leading to very slow volume changes as well as changes in volume according to position. Because the arterial pulsations are higher in frequency than the other signals related to blood volume changes, the arterial pulsations can be isolated by filtering out all fluctuations in blood volume below approximately 0.5 Hertz. However, if the respiratory rate is rapid, the cutoff frequency must be raised.

The rapidly pulsatile signal corresponds to the arterial compartment. Each time the heart beats, this compartment undergoes an expansion and contraction as the heart pulse wave passes through. This signal is conventionally called the volume pulse contour which, in the finger is termed the digital volume pulse (DVP). The signal from the arterial compartment will be affected by changes in blood pressure and temperature. As temperature increases, the amplitude of the volume pulse contour increases. As blood pressure increases, the amplitude of the volume pulse contour increases.

The raw PPG signal also contains a DC (or nonpulsatile) signal component which varies with temperature but which does not vary with changes in blood pressure. Observation of the fluctuations in this DC component allows for correction of temperature related changes and allows the amplitude of the arterial volume pulse contour to be corrected for variation in temperature. For example, it would be possible to determine the impact of temperature change by following the changes in the raw PPG signal after the user has cooled his/her finger in a glass of ice water as the finger rewarms. It would also be possible to adjust the DC level of the PPG signal to compensate for change in temperature.

Generally, removing the DC or nonpulsatile signal from the conditioned PPG signal results in a signal that is related to pulsatile changes in finger blood volume and also to vascular and respiratory effects. Low pass filtering the conditioned PPG signal removes the faster signal components related to heart beat (i.e. the highly pulsatile signals) and the resulting slowly pulsatile signal can be used to track heart rate and respiratory related physiological characteristics. The exact frequency needed to isolate heart and respiratory signals varies with changes in heart rate and respiratory rate and it is necessary to adapt the cutoff frequency to the heartbeat and respiratory rate of a particular user.

For example, it has been observed that a relatively clear slowly pulsatile signal can be obtained by filtering out signal components from a typical conditioned PPG signal which have a frequency of 0.5 Hertz or higher. High pass filtering the conditioned PPG signal removes the slower signal components related to respiration (i.e. the slowly pulsatile signals) and roughly isolates the highly pulsatile signal (i.e. the DVP signal) which reflects blood volume changes related to heartbeat. The DVP signal can be analyzed to produce a plurality of signals related to the state of the cardiovascular system as well as respiratory function as will be described.

Also, it has been observed that varying finger pressure and finger motion while a user's finger is positioned on PPG sensor 12 results in fluctuations in the amplitude of the derived nonpulsatile and pulsatile signals. Pressure exerted on the fingertip causes a decrease in the volume of blood in the tissues of the fingertip. Tilting the body to one side or another will also produce changes in the amplitude of the nonpulsatile and pulsatile portions of the PPG signal. Rapid fluctuations in the PPG signal which relate to mechanical disruption of the skin-PPG interface can be compensated by conventionally known artifact reduction techniques which substantially decrease the distortion of the volume pulse contour caused by movements of the finger and/or PPG sensor 12.

Analysis of the DVP is difficult because of the overlapping of the various primary and reflected waves. Generally, the systolic and the dicrotic waves and the reflections of these waves travelling within the arterial system form the DVP signal. The systolic wave, the systolic reflected wave, the dicrotic wave and the dicrotic reflected wave interact to obscure the peak of the systolic wave as well as the foot and the peak of the systolic and dicrotic reflected waves. In order to properly characterize the DVP, analysis of the waves contributing to the shape of the DVP must be undertaken. Signals in the DVP, related to the systolic and dicrotic reflected waves, provide a rich source of information about the health of the cardiovascular system and other internal organs.

Figure 9A:
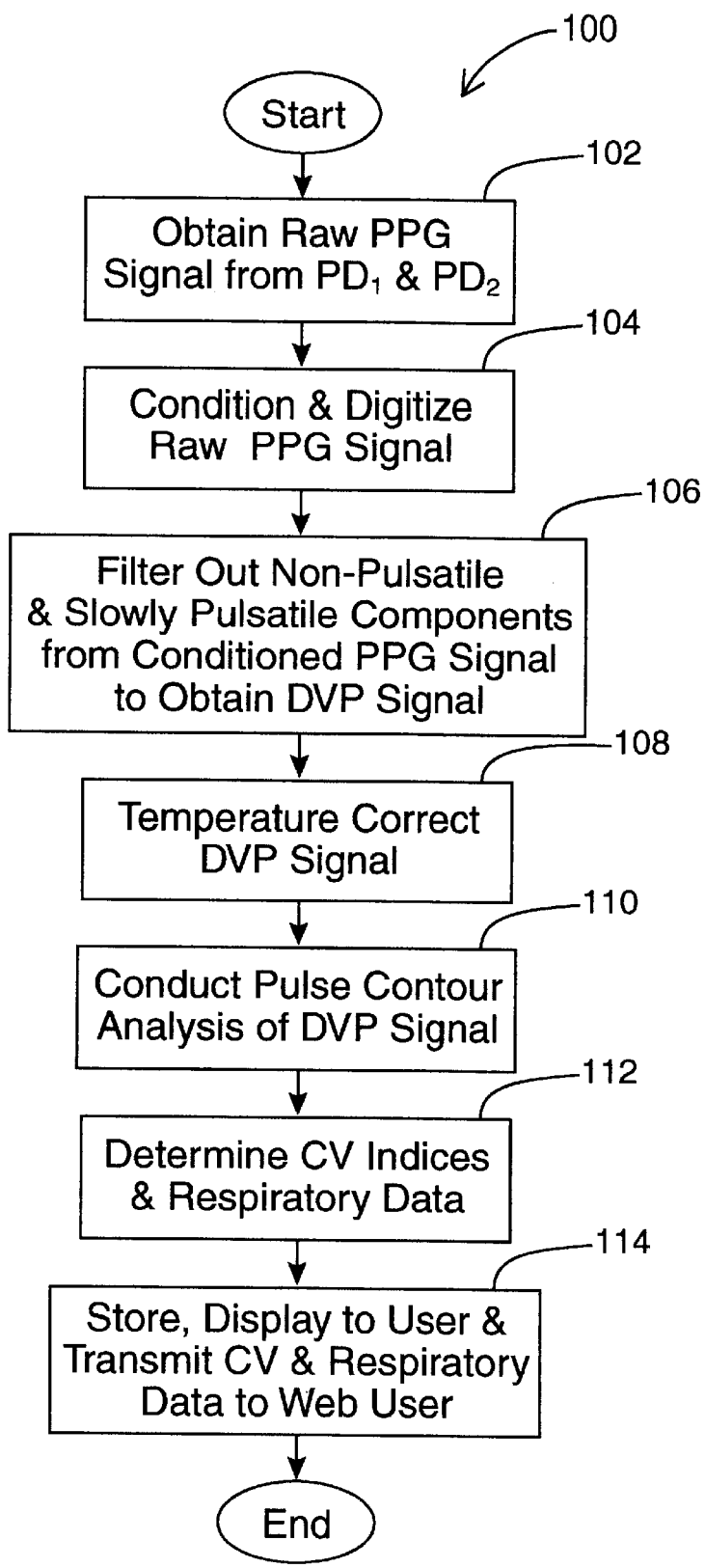
FIG. 9 is a flowchart showing the general process steps to obtain cardiovascular and respiratory data which are executed by the microcontroller of the user input device and the CPU of the processing device of FIGS. 1 and 2.

Referring to FIG. 9A, there is shown an overview of the process 100 of DVP pulse contour analysis according to the present invention. FIG. 9A is representative of the process of DVP pulse contour analysis and also the underlying computer programs of system 10. Specifically, the execution of process 100 is directed under program control by microcontroller 26 of user interface device 20 and CPU 5 of processing device 14 and associated computer peripherals.

Referring now to FIGS. 1, 2, 3, and 9A, process 100 begins with obtaining a raw PPG signal from photodiodes $PD_1$ and $PD_2$ (102) from PPG sensor 12 and conditioning/digitizing the raw PPG signal (104) using signal conditioning module 24 and microcontroller 26 of user input device 20. The CPU 5 of processing device 14 then effects the high pass filtering of the conditioned PPG signal (106) to remove the non-pulsatile and slowly pulsatile components of the PPG signal to obtain the DVP signal.

Before beginning analysis of the DVP signal, it is important to correct the DVP with regard to temperature variation. The DVP signal can be corrected by CPU 5 of processing device 14 for temperature related variations (108) using temperature calibration data from thermistor 23 of user input device 20. Since system 10 can specify the absolute temperature at the skin surface it is possible to use this absolute value to compensate for variations in the DVP signal due to temperature. In this way, a more accurate determination of systolic and diastolic blood pressures can be obtained from the DVP signal as will be explained.

Figure 9B:
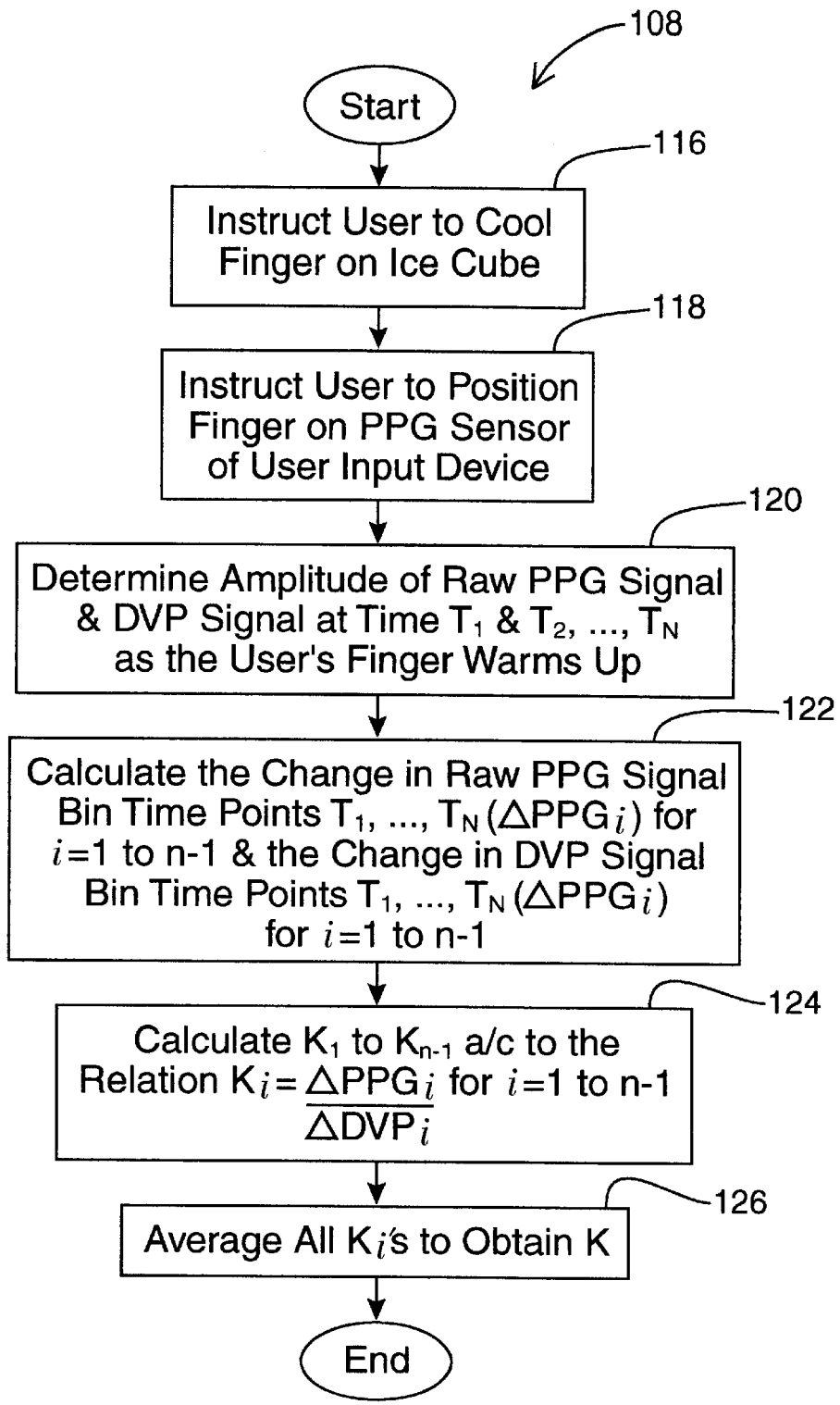

As shown in FIG. 9B, it is possible to achieve temperature correction using the raw PPG signal with a correction factor that can be calculated for a particular user or predetermined for general application. The relationship between change in PPG amplitude and change in the DVP amplitude can be represented by the mathematical expression:

$$\Delta PPG = K(\Delta DVP),$$

where K is a constant. Accordingly, a value for K can be determined by subjecting a finger to a change in volume independent of blood pressure. CPU 5 of processing device 14 can be appropriately programmed to correct the DVP amplitude to compensate for changes in blood volume that are unrelated to blood pressure effects.

Specifically, CPU 5 of processing device 14 can be programmed to instruct the user to cool his or her finger (i.e. by placing it on an ice cube for a period of time) (116) and then to position his or her finger over PPG sensor 12 of user input device 20 (118). CPU 5 of processing device 14 then determines the amplitude of the raw PPG signal (at node A of conditioning circuit 24 of FIG. 3) and the amplitude of the DVP signal (discussed above in relation to step 106 of FIG. 9A) at sample times $T_1, T_2, \ldots, T_n$ as the user's finger warms up (120). The changes in amplitude of the raw PPG signal between sample times $T_1, T_2, \ldots, T_n$ (or $\Delta PPG_i$ for i=1 to n−1) and the changes in amplitude of the DVP signal between sample times $T_1, T_2, \ldots, T_n$ (or $\Delta DVP_i$ for i=1 to n−1) are calculated (122). Values $K_1$ to $K_{n-1}$ are calculated according to the relation $K_i = \Delta PPG_i/\Delta DVP_i$ for i=1 to n−1 (at 124). Finally, the average of the values $K_1$ to $K_{n-1}$ is calculated to determine the value of K for the user.

In this way, the relationship between the amplitudes of the raw PPG signal and the DVP signal can be used to determine a working constant value for K can be determined. In this way it is possible to use the DVP signal to obtain a more reliable reading for blood pressure values. It should be noted that temperature correction is not necessary for cardiovascular indices that are amplitude independent. Indices which are based on relative measurements made on the DVP contour at different points in time or at the same point on two separate DVP contours will not dependent on absolute determination of DVP amplitudes.

CPU 5 of processing device 14 then conducts pulse contour analysis of the DVP signal (110) to obtain characteristics of the systolic wave and the systolic reflected wave as will be discussed in detail. CPU 5 of processing device 14 converts these characteristics into cardiovascular indices and basic cardiovascular and respiratory and neurological physiological data is calculated (112). Finally, CPU 5 of processing device 14 stores the physiological data in memory for future retrieval, displays the data to user on display 7 and transmits the data over communication network 18.

Several methods of pulse contour analysis are contemplated by the present invention. As previously discussed, various characterizations of the systolic reflected wave discussed in the literature fail to accurately identify the systolic reflected wave peak accurately. Using the methods of the present invention, it is possible to characterize the systolic reflected wave (e.g. the systolic reflected wave peak) from within the DVP signal.

First, as shown in FIGS. 10A to 10E, it has been determined that by calculating the first, second and the fourth derivatives of the DVP signal, it is possible to identify a number of critical points related to the systolic wave and the systolic reflected wave. Specifically, FIG. 10A shows the DVP signal, FIG. 10B shows the first derivative of the DVP signal, FIG. 10C shows the second derivative of the DVP signal, FIG. 10D shows the third derivative of the DVP signal, and FIG. 10E shows the fourth derivative of the DVP signal.

As shown in FIG. 10B, in known manner, the pulse relative maximum and minimum points correspond to the zero crossings of the first derivative curve. The maximum point of the first derivative curve corresponds to the point of maximum pulse slope, that is, the point in early systole at which the pulse is rising most steeply to its first peak. The point of systolic onset (at D), which is also referred to as the wave foot, corresponds to the first negative-to-positive zero crossing (at D') which precedes the first derivative maximum point. The systolic peak (at A) can also be identified on the DVP signal as the time of the zero crossing from positive to negative of the first derivative (at A') after the peak of the first derivative.

Once the point of systolic onset is located, the maximum peak for the reflected wave (at B) can be determined from the DVP signal. In order to positively identify the maximum peak for the reflected wave (at B), the fourth derivative curve must be examined. Specifically, it has been determined that the second zero crossing from negative-to-positive (at B') of the fourth time derivative of the DVP signal is a consistent indicator of the maximum peak of the reflected wave pulse (at B) as shown.

It is noteworthy that many authors of scientific literature related to the observation of the augmentation index endeavour to identify what is terms the 'inflection point' on the aortic pressure pulse contour. In contrast, the present invention is directed at identifying the slope change associated with the maximum of the reflected wave, as it has been observed that the maximum point of the reflected wave has a stronger correlation with the aortic reflected wave signal. Because of the aortic reflected wave signal's ability to propagate in a retrograde fashion with little attenuation, it will always substantially contribute to the maximum of the slope change following the inflection point. In contrast, the inflection point is more likely to be influenced by reflected wave signals other than the aortic reflected wave signal.

However, it should be noted that a number of points on the fourth derivative of the DVP signal can be used to determine critical points on the aortic reflected wave contour. For example, it has been observed that the second zero crossing from positive to negative of the fourth derivative of the DVP signal can be used to identify the inflection point on the aortic reflected wave.

From observation of a large number of clinical cases, it has been experimentally confirmed that while certain changes in slope of the aortic reflected wave contour can be identified in the first and third derivatives of the DVP signal, there are a significant number of cases where all trace of the reflected wave maximum is lost or completely obscured by the primary systolic pulse wave within the DVP signal. These cases tended to be in older-patients where the aortic reflected wave was closer to the primary systolic pulse wave than in younger patients. It was determined that by taking the fourth derivative, it was possible to consistently determine the maximum of the aortic reflected wave signal within the DVP signal.

Figure 11A:
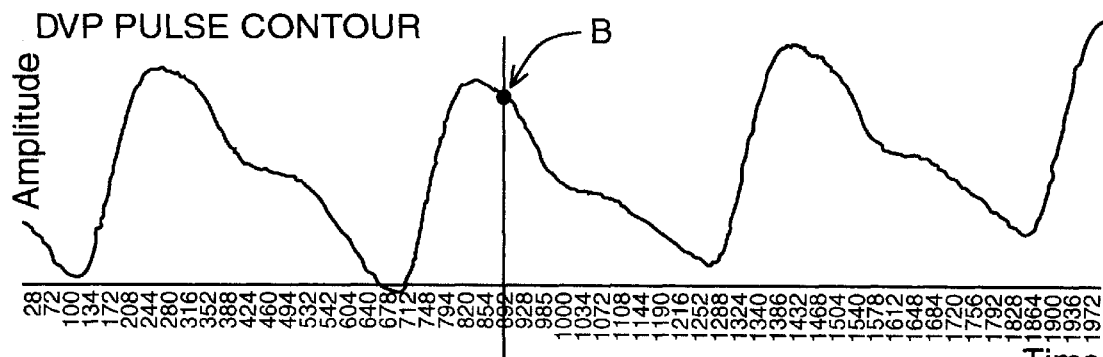
FIG. 11A is a graph showing the DVP signal outputted by the user input device of FIG. 2.
Figure 11B:
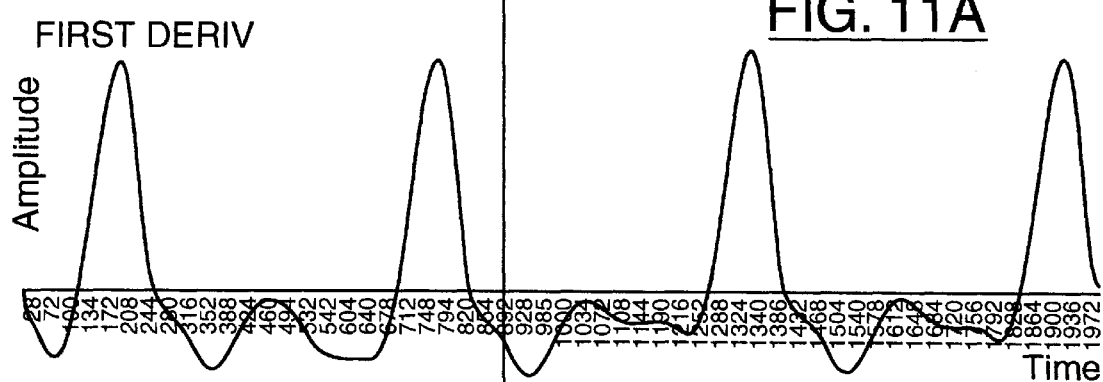
FIG. 11B is a graph showing the first derivative of the DVP signal of FIG. 11A.
Figure 11C:
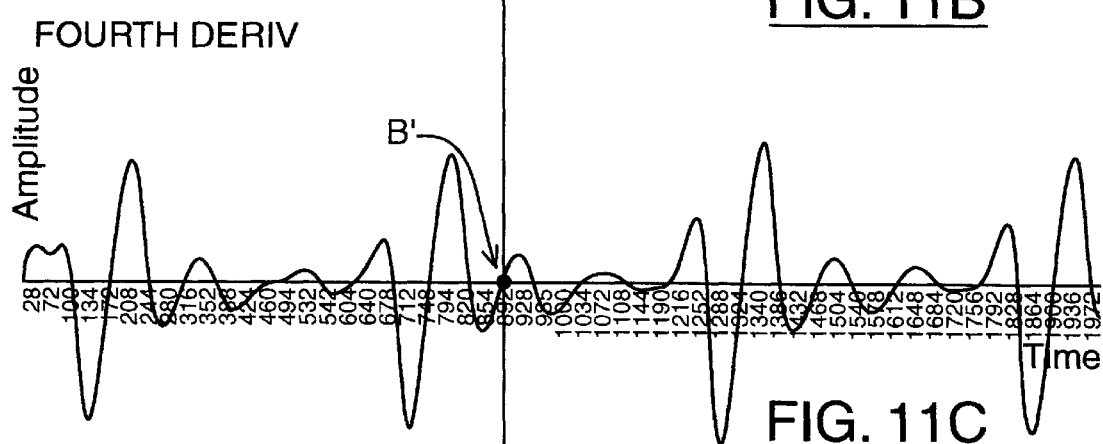
FIG. 11C is a graph showing the fourth derivative of the DVP signal of FIG. 11A.
Figure 11D:
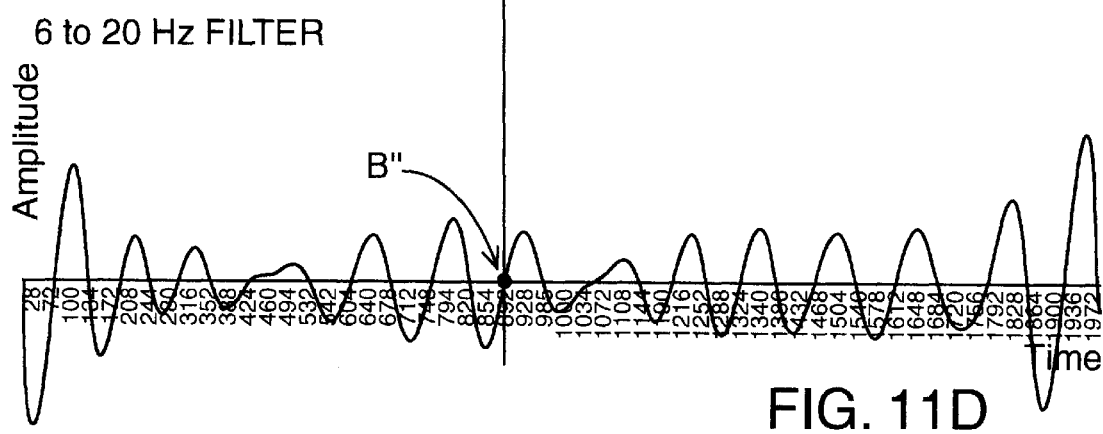
FIG. 11D is a graph showing the DVP signal of FIG. 11A after it has been passed through a 6 to 20 Hz bandpass filter.

Second, as shown in FIGS. 11A to 11D, it has been determined that it is also possible to identify a number of critical points related to the systolic wave and the systolic reflected wave by appropriately bandpass filtering the DVP signal. For illustration FIG. 11A shows the DVP signal, FIG. 11B shows the first derivative of the DVP signal, FIG. 11C shows the fourth derivative of the DVP signal, and FIG. 11D shows the result of bandpass filtering the DVP signal using a bandpass filter with cutoff frequencies of 6 and 20 Hertz. It has been observed that the reflected wave signal is strongest at 4 to 8 Hertz. 6 Hertz lies in the middle of this range. 20 Hertz is low enough to eliminate high frequency noise and high enough to observe crucial high frequency reflected wave components.

As shown in FIGS. 11A, 11C and 11D, the maximum peak for the systolic reflected wave (at B) can be determined from the DVP signal from either the fourth derivative or the band passed DVP signal. By bandpass filtering the DVP signal, a signal with zero crossing points that are closely associated with those of the fourth derivative of the DVP signal is produced. Specifically, the second zero crossing from negative-to-positive (at B') of the fourth time derivative of the DVP signal occurs at the same time as the second zero crossing from negative-to-positive (at B") of the bandpass filtered DVP signal. Accordingly, the DVP signal band passed in this fashion can be utilized to identify the systolic reflected wave peak (at B). It has been determined that a limitation of this method is that the bandpass filter introduces a phase delay into the DVP signal. Consequently, it is necessary to adjust the DVP signal to compensate for the phase delay.

While the above methods allow for the accurate identification of the foot of the systolic wave pulse and the systolic wave peak, it is preferable to use the respiration frequency extraction technique of the present invention to obtain an accurate estimate of the entire signal contour shape of the reflected wave components originating in the abdominal aorta, as will be described. The shape of the aortic reflected wave is a rich signal that varies with changes in function of the heart, lungs, and organs of the abdominal vascular bed and allows for determination of related diagnostics. Also, once the aortic reflected wave contour is obtained, it is possible to extract accurate representations of the systolic wave and the systolic reflected waves from the DVP signal as will be explained.

The interaction between primary and reflected waves obscures wave detail preventing the determination of exact timing and amplitude relationships between primary and reflected waves. Also, the shape of the DVP changes on a beat to beat basis due to changes in the timing and amplitude of the reflected wave components associated with respiration. With inspiration, blood pressure falls and the aortic reflected waves will arrive later at the finger and with smaller amplitude. As blood pressure decreases, the pulse transit time increases. This inverse relationship between blood pressure and pulse transit time causes the reflected wave signal to appear earlier or later in the DVP signal.

Due to the fact that the reflected wave contour is shifting back and forth within the underlying DVP signal, it is possible to use signal extraction techniques to remove the components which do not vary with breathing. By removing the components associated with respiration from the DVP signal which otherwise interact and obscure each other's characteristics, it is possible to ascertain the shape of the isolated reflected wave signal within the remaining components of the DVP and to determine the timing and amplitude characteristics of the reflected wave. This information can then be used for calculation of cardiovascular parameters such as aortic pulse wave velocity.

Figure 12A:
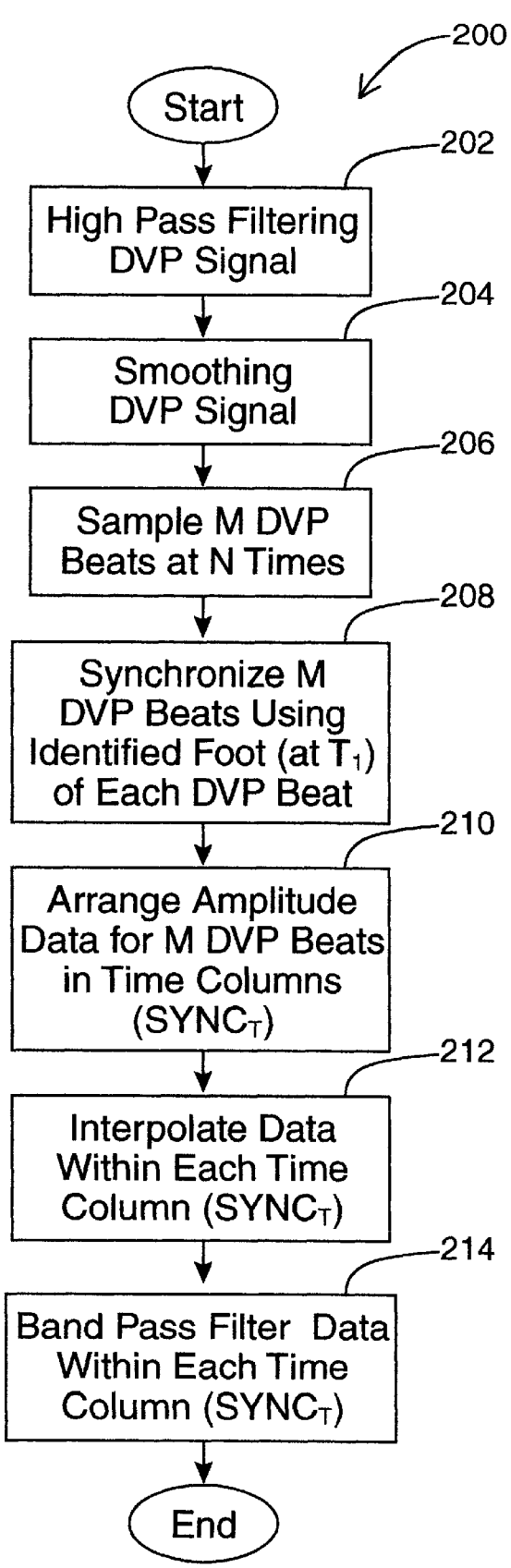
FIG. 12A is a flowchart illustrating a method of the present invention for extracting the reflected wave contour from the DVP signal.
Figure 12B:
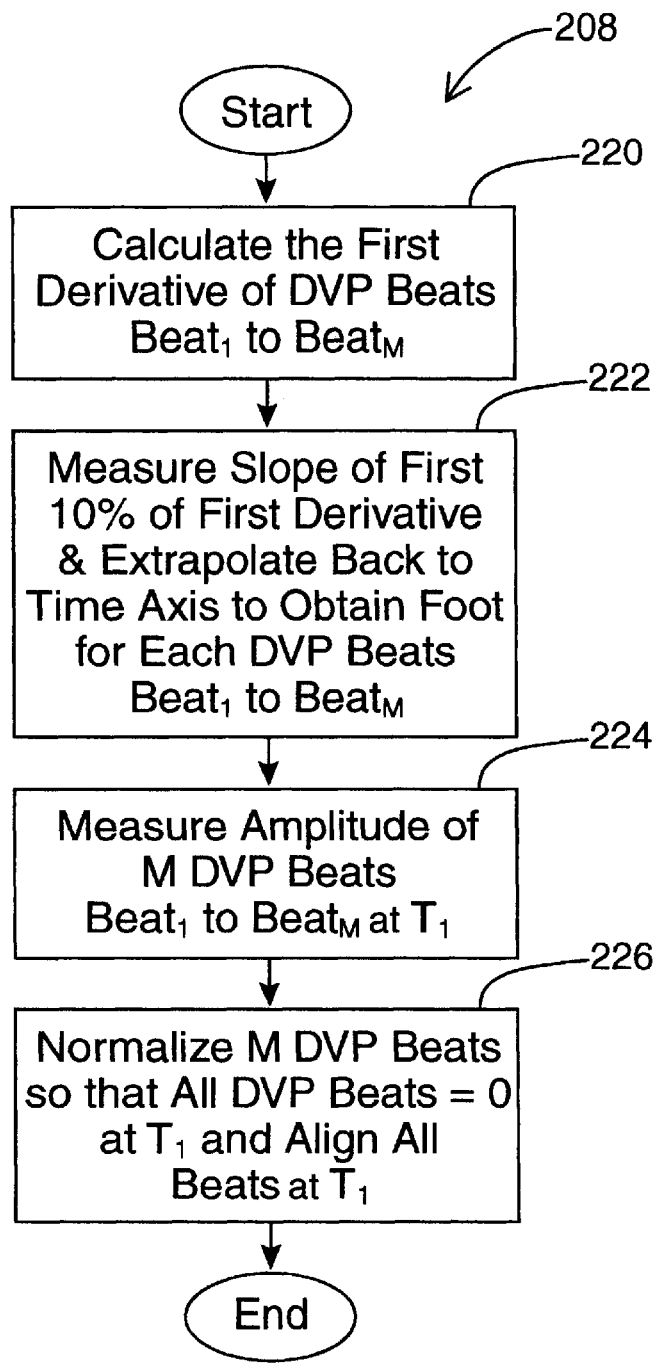
FIG. 12B is a flowchart showing how the individual DVP beats of the DVP signal are synchronized and normalized.

Referring to FIGS. 12A and 12B, there is shown an overview of the steps of the respiratory matrix filtering method 200 of the present invention. This method is based on the observation that the aortic reflected wave signal in the DVP signal shifts with respiration due to changes in blood pressure associated with respiration. That is, the reflected wave components of the DVP signal originating in the abdominal aorta are characterized by a transit time that varies with respiration. The change in blood pressure that occurs with respiration induces changes in aortic pulse wave velocity. These changes result in variations in the aortic reflected wave transit time which in turn causes changes in the position of the reflected wave within the DVP signal in association with respiration. The DVP signal also changes with respiration due to the effects of blood pressure and cardiac output changes cycling with respiration. With inspiration, the blood pressure falls causing a decrease in the DVP amplitude. The respiratory matrix filtering method 200 eliminates respiratory induced baseline and arterial volume changes from the DVP signal by filtering out those components of the DVP signal that do not change on a beat to beat basis (i.e. the DC components), in order to isolate the aortic reflected wave.

Figure 12C:
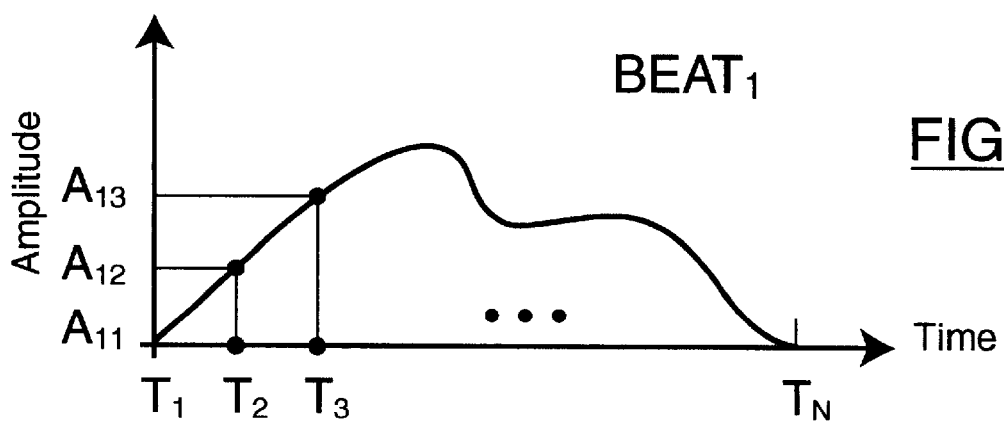
FIGS. 12C, 12D and 12E are graphs showing three individual DVP beats.
Figure 12D:
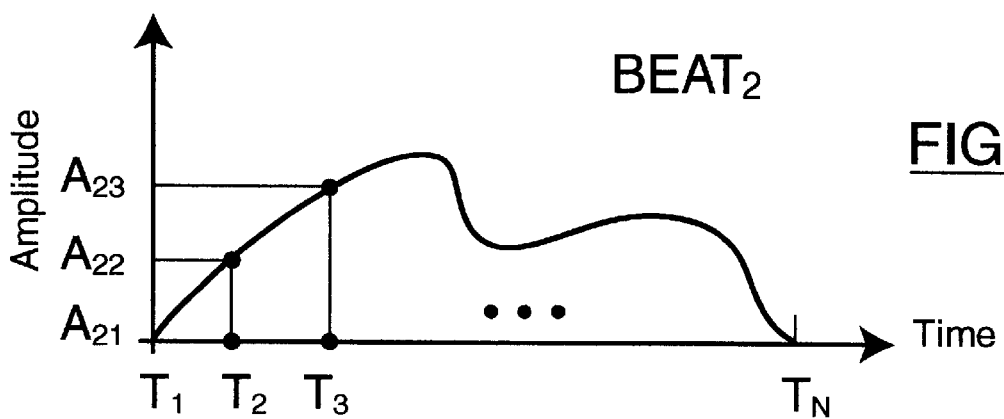
Figure 12E:
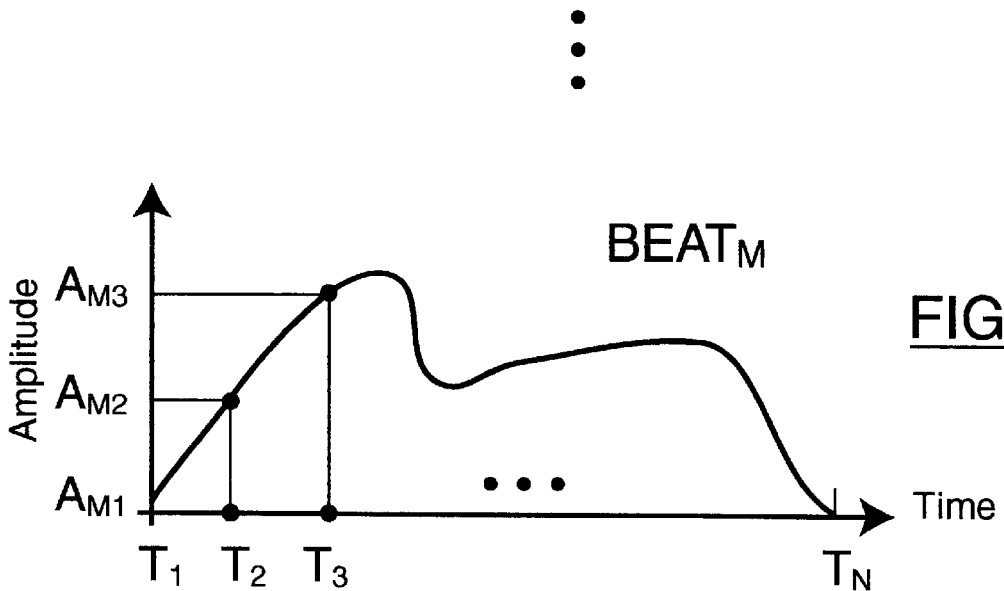

The DVP signal is first high pass filtered above 0.5 Hertz (202) to remove baseline fluctuations related to respiration. The DVP signal is then smoothed (204) using a conventionally known smoothing routine, (e.g. the Savitzky-Golay routine) in order to smooth the signal, to eliminate noise and to interpolate between sample data points. The individual DVP beats within the DVP signal are then monitored and analyzed over a period of time. In particular, the DVP signal is observed until M DVP beats (i.e. $BEAT_1$, $BEAT_2$, $BEAT_3$, ... $BEAT_M$) have been observed. The M DVP beats $BEAT_1$, $BEAT_2$, to $BEAT_M$ are sampled periodically at N sampling points (i.e. $T_1$ to $T_N$) (206) as shown in FIGS. 12C, 12D and 12E to obtain corresponding amplitudes (e.g. $A_{11}$, $A_{12}$, $A_{1N}$ and $A_{M1}$, $A_{M2}$, $A_{MN}$).

Typically 100 to 200 beats are observed by method 200 (i.e. M has a value of between 100 and 200). Since a typical DVP beat has a duration of 1.0 seconds and since samples are taken every millisecond, roughly 1000 samples of each DVP beat are taken, depending on the heart rate of the user. Time is measured in increments of 1 millisecond and amplitude of the DVP beats is measured in increments of 1 millivolt. Amplitude of the DVP beats typically falls within the range of 0 and 4000 millivolts depending upon the level of voltage amplification of the PPG signal provide by signal conditioner module 24.

The M individual DVP beats $BEAT_1$, $BEAT_2$, to $BEAT_M$ are then synchronized. This is accomplished by first identifying the initiation of each beat (i.e. the foot of the systolic pulse wave) using signal analysis technique steps shown in FIG. 12B (208). Specifically, the initial time sample point, T, is determined for each of the M individual DVP beats $BEAT_1$, $BEAT_2$, to $BEAT_M$, by calculating the first derivative of each DVP beat $BEAT_1$, $BEAT_2$, to $BEAT_M$ (220) (not shown).

For each DVP beat $BEAT_1$, $BEAT_2$, to $BEAT_M$, the slope of the sampling data points comprising the first 10 percent of the rising limb of the first derivative leading to the peak for each DVP beat $BEAT_1$, $BEAT_2$, to $BEAT_M$, is extrapolated backwards to determine the zero crossing point on the time axis of the plot (222). It has been observed that this zero crossing point represents the initiation of the DVP beat with reasonable accuracy. This approach is believed to provide superior results than zero crossing detection using conventional sampling techniques for several reasons. First, it is difficult to identify accurately the zero crossing point when low sampling speed is utilized. By extrapolating a line derived from the slope of the rising limb down to the time axis of the plot, it is possible to accurately pinpoint the precise time location of the zero crossing point. Second, by using the first 10 percent of the rising limb of the DVP beat, it is possible to avoid reflection induced perturbations.

Each DVP beat $BEAT_1$, $BEAT_2$, to $BEAT_M$ is then time synchronized by measuring the amplitude of the M DVP beats $BEAT_1$, $BEAT_2$ to $BEAT_M$ at $T_1$ (224), normalizing the M beats so that all DVP beats are zero at $T_1$ and aligning the DVP beats at the time $T_1$ for each beat (226). It has been observed that the DVP signal amplitude shifts on a beat to beat basis as a result of shifts in blood pressure, finger arterial blood volume and shifts in the timing of the aortic reflected curve signal in association with respiration.

Once a train of DVP beats $BEAT_1$, $BEAT_2$, to $BEAT_M$ is isolated and synchronized, the amplitude values for the DVP beats $BEAT_1$, $BEAT_2$, to $BEAT_M$ are arranged in Spreadsheet A (210) in columns of sampling times ($T_1, T_2, \ldots, T_N$) as shown in FIG. 12F. For example, the amplitude of all the DVP beats $BEAT_1$, $BEAT_2$, to $BEAT_M$ at each beat's $T_1$ is placed in the first column of Spreadsheet A (note that the amplitudes at each beat's $T_1$ have all been normalized to zero), the amplitude of all of the DVP beats $BEAT_1$, $BEAT_2$, to $BEAT_M$ at each beat's $T_2$ is placed in the second column, and so on. $T_{per}$ is the period between derived samples and is generally equal to the actual sampling interval. Thus, $T_1+T_{per}=T_2 \ldots T_N=T_{N-1}+T_{per}$ where N is the total number of samples per beat (as discussed before, $T_{per}$ is typically 1 millisecond). The last sampling period will correspond to the first instance of a beat in the series entering a new systolic period as identified using the first derivative of the DVP beat as discussed above.

Columns corresponding to each sampling time are filled with the amplitudes of all beats at that sampling time. By treating the series of values in each column as a new signal $SYNC_T$ where T is the sample time, it is possible to use filtering algorithms to extract components from the signals $SYNC_T$ (for T=1 to N). As discussed above, the aortic reflected wave shifts back and forth within the DVP signal with respiration (i.e. at the respiratory frequency). Accordingly, it is possible to observe the aortic reflected wave by looking only at those parts of the DVP signal which vary on a beat to beat basis. The portions of the signals $SYNC_T$ that do not vary on a beat to beat basis are the DC and nonpulsatile components which do not vary with blood pressure.

By appropriately bandpass filtering the signals $SYNC_T$ in the range of the user's respiratory frequency, it is possible to retain those components in the DVP signal that vary at a rate associated with respiration (i.e. those that are related to the aortic reflected wave). Finally, it should be noted that the signal distortions associated with motion artifact will generally occur at a higher frequency than the respiratory rate which suggests that this form of bandpass filtering around the respiratory frequency will also serve to produce a noise free respiration contour.

The beat sample data points of spreadsheet A is obtained from the continuous DVP beat contours as shown graphically in FIG. 12G. Each set of beat data samples for a particular sample point $T_T$ (for T=1 to N) (i.e. each signal $SYNC_T$) are then separately re-graphed for interpolation purposes (212). Specifically, signal $SYNC_5$ shown in FIG. 12H, is obtained by graphing the sample data obtained from each DVP beat $BEAT_1$, $BEAT_2$, to $BEAT_N$ at sample point $T_5$. The sample points for each DVP beat will be related to the absolute time in milliseconds from sample point $T_1$ of $BEAT_1$ as shown on the time axis of FIGS. 12G and 12H. Also, the time axis of the graphs shown in FIGS. 12G and 12H, represents time measured continuously from time $T_1$ of $BEAT_1$ (or $T_{11}$) in milliseconds. The interval between sample times (e.g. between $T_{11}$, and $T_{12}$ etc.) will be the same as in spreadsheet A (FIG. 12F). As shown, there will be many empty points between the sample points. By using a conventionally known polynomial curve fitting algorithm, it is possible to interpolate between sample points and to produce an approximately fitted curve for each signal $SYNC_T$ as shown in FIG. 12H.

Once the curve of each sample point for each beat $BEAT_1$, $BEAT_2$, to $BEAT_N$ has been filled using interpolation techniques, these curves are bandpass filtered using a filtering algorithm (214). Without interpolation, filtering of the widely separated points would create sharp transients that would corrupt the result. The bandpass filter has a center frequency that centres around the respiratory frequency of the user. In general, the lower cutoff of 0.1 Hertz and an upper cutoff frequency of 0.5 Hertz have been used advantageously. However, if it is determined that a particular individual user's respiratory rate is outside of these limits, the cutoff frequencies of the band pass filter can be adjusted. By bandpass filtering the signals $SYNC_T$, amplitude components of the DVP beats $BEAT_1$, $BEAT_2$, to $BEAT_M$ which do not vary at or about the respiratory rate are filtered out leaving a signal which will predominantly contain the aortic reflected wave (which varies at a frequency that falls within the bandpass filter corner frequencies).

Once the signals $SYNC_T$ have been band pass filtered, the data from the cells originally occupied with data prior to interpolation, is returned to the associated column of spreadsheet A. All DC and fast AC components of the signal will have been removed and the only remaining signals will be related to respiratory variation. The aortic reflected wave may then be separated from other minor components using conventional analysis techniques. It will be possible to examine the rows of data corresponding to each beat. Graphing the data will reveal the contour of the aortic reflected wave. The band pass filtered data from a series of beats could also be displayed to the user in a waterfall mode. With each separate bandpass filtered DVP beat layered sequentially, the aortic reflected wave could be seen to move cyclically towards and away from $T_1$ within each DVP beat.

The aortic reflected wave has a parabolic shape most evident at its peak when seen in the signal obtained using the respiration matrix filtering method 200. Extrapolation of the parabolic aortic reflected wave from the shape will allow for precise definition of the initial zero crossing point of the parabola. This point corresponds to the appearance of the aortic reflected wave and can be used to precisely define the transit time of the aortic reflected wave. With knowledge of the distance between the heart and the reflecting site in the abdomen (an estimate can be obtained based on a user's height), the aortic pulse wave velocity and the aortic compliance for a user can be calculated using the conventional relationship between velocity, distance and time. The distance from the heart to the reflecting site is about the distance to the origin of the renal arteries.

It is contemplated that a number of other promising wave analysis techniques could be used to isolate the aortic reflected wave from the DVP signal. First, the technique of homomorphic analysis could be used to obtain the curve of the aortic reflected wave as discussed in the text "A Casestudy Approach to Solve Problems in Biomedical Signal Analysis", Rangaraj, M, Rangayyan (IEEE Press, New Jersey: 2000), Chapter 4, pgs. 128 to 136. Specifically, the DVP signal can be though of as a prime impulse and a train of echoes superimposed on a dicrotic impulse and another associated train of echoes. These echoes can be characterized using the conventionally known technique of homomorphic analysis. This technique is based on the premise that the shape or morphology of the echoes are similar in shape to the primary impulse. It has been observed that this technique is proficient at isolating the primary impulse (i.e. the systolic wave pulse).

Second, the aortic reflected wave pulse could be obtained using conventionally known adaptive filtering techniques. It would be possible to use adaptive filtering techniques to isolate the components of the DVP signal that vary in association with respiration. Finally, it is contemplated that since the aortic reflected wave components have characteristic frequency distribution which differs from that of the primary (systolic) wave, it would be possible to use time-frequency analysis to isolate the aortic reflected wave components and characteristics.

Once the aortic reflected wave contour has been obtained by respiratory frequency extraction of the DVP signal as discussed above, the systolic reflected wave as differentiated from the dicrotic reflected wave can be analyzed to obtain information regarding short and long term changes in the cardiovascular system and other organ systems. The systolic reflected wave characteristics are determined by its passage through the vascular components of the abdominal organs and the large blood vessels of the cardiovascular system, and accordingly are a rich source of cardiovascular information for the user as will be discussed. Also, as discussed, by subtracting the isolated reflected wave signal from the overall DVP contour, it is possible to better identify the systolic and dicrotic waves, since the systolic peak is often obscured by the reflective wave.

The use of the derivative, high pass filtering, and respiratory matrix filtering techniques described above can be used to determine a variety of conventionally known indices from the systolic wave and the systolic reflected wave which are useful correlates of various cardiovascular parameters, including mean blood pressure, respiratory function, and aortic pulse wave velocity.

These indices all vary on a beat-to-beat basis with changes in aortic transit time of the reflected wave from a source in the abdomen as previously discussed. They also vary with mean blood pressure and respiration, and accordingly all of these indices can be used to track mean blood pressure and to synthesize the respiratory signal. As previously discussed, the amplitude of the DVP signal is highly variable as it is extremely sensitive to ambient light, temperature, mechanical and other environmental disturbances. Accordingly, it is necessary to perform analysis of the DVP signal by making relative measures of various amplitudes and timing delays of components within the DVP signal instead of absolute measures.

Referring back to FIG. 8, several relevant cardiovascular indices which can be determined by system 10 are based on identification of the systolic foot (at D), the systolic peak (at A) and the systolic reflected wave peak (at B) of the DVP signal. These points can be identified using the three approaches discussed above.

Specifically, referring back to FIGS. 10A and 10B, the systolic foot (at D) is identified as the time of the zero crossing of the first derivative of the DVP signal (at D') preceding the first derivative maximum. The systolic peak (at A) is identified as the time of the zero crossing from positive to negative of the first derivative (at A') after the peak of the first derivative. Now referring to FIGS. 10A and 10E, the reflected wave peak (at B) is identified as the time of the second zero crossing from negative to positive of the fourth derivative of the DVP signal (at B').

As previously discussed, the high pass filtered DVP signal can be used in place of the fourth derivative of the DVP signal to determine the systolic and reflected wave peaks. Also, as discussed, the location of the systolic wave foot the systolic wave peak and the systolic reflected wave peak can be determined through the use of the respiratory frequency extraction technique discussed above to extract the aortic reflected wave.

It has been determined that three indices, namely $\Delta T_{Ref}$, $INDEX_{Ref}$, and $INDEX_{2nd\ Deriv}$ are useful correlates for many well-known cardiovascular parameters such as mean blood pressure and aortic pulse wave velocity. These indices can be easily determined from the various peak and foot measurements of the DVP signal discussed above and which are shown on FIG. 13 in association with the following indices:

1. $\Delta T_{Ref}$ is a measure of the time between the foot of the systolic wave pulse (at D on FIG. 13) and the peak of the systolic reflected wave pulse (at B on FIG. 13) in the DVP signal. The time difference between the foot (or initiation) of the systolic pulse and the maximum peak of the reflected wave is strongly representative of the pulse transit time of the reflective wave as it travels back from the heart to the reflection site in the trunk and back to the subclavian artery. Accordingly, it is possible to determine aortic pulse wave velocity from measured values of the pulse transit time by correcting for height (i.e. approximate travel path), as previously discussed.

While it is also possible to measure the time between the peak of the systolic wave pulse and the peak of the systolic reflected wave, it is preferable to measure the time from the foot of the systolic wave pulse as the beginning of the systolic pulse is relatively free of distortion from reflected waves.

Figure 13:
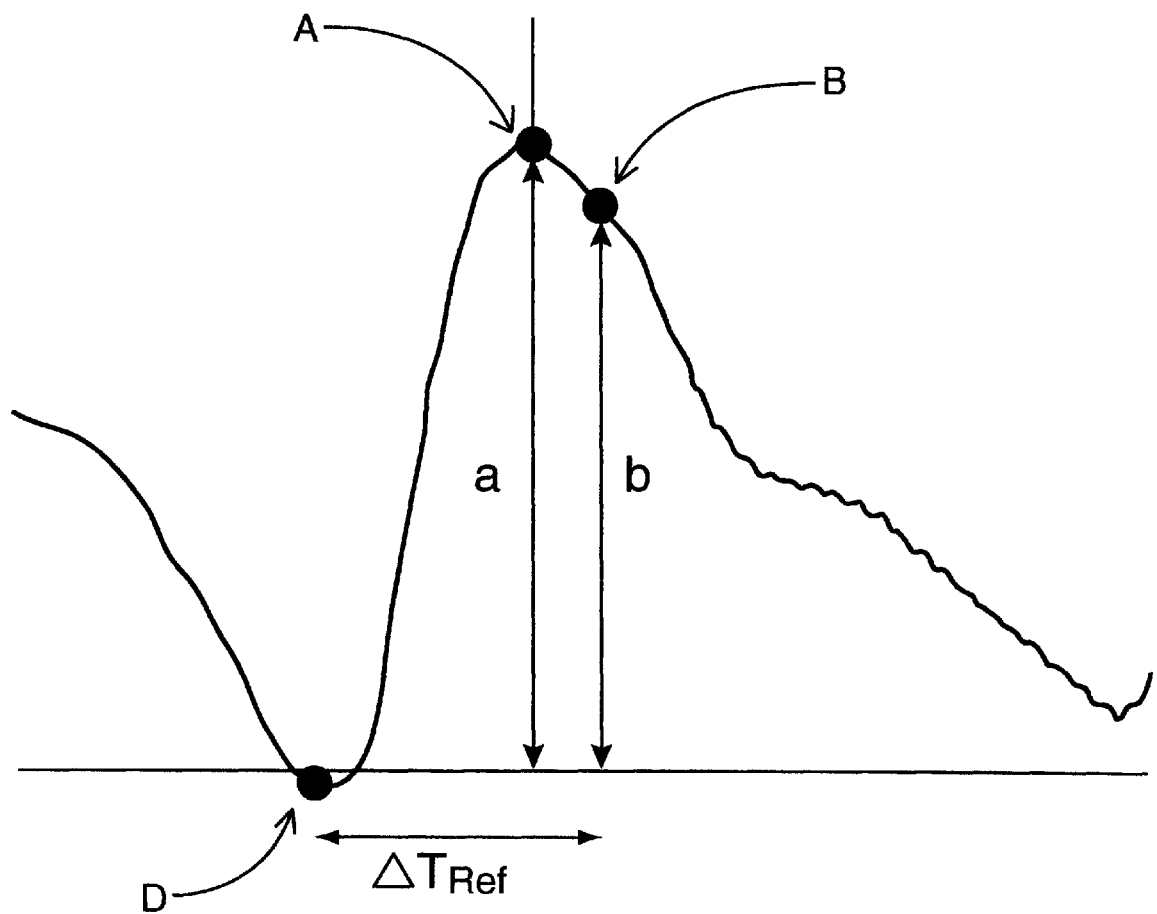
FIG. 13 is a graph showing various indices on a sample DVP signal pulse.

2. $INDEX_{Ref}$ or the reflected wave index, is analogous to the conventional pressure pulse augmentation index. The conventional pressure pulse augmentation index is the ratio of the main systolic peak to the amplitude of a portion of the pressure pulse contour associated with the aortic reflected wave. $INDEX_{Ref}$ is the percentage ratio of the amplitude of the DVP signal at the reflected wave peak (at B) (i.e. height "b" on FIG. 13) relative to the amplitude of the DVP signal peak (at A) (i.e. height "a" on FIG. 13). Accordingly, $INDEX_{Ref}=b/a*100\%$ (FIG. 13). While the augmentation index is conventionally derived from the proximal aortic pressure pulse contour, the augmentation index derived from the DVP signal will also be correlated with aortic pulse wave velocity and other cardiovascular parameters. It should be noted that if the reflected wave peak occurs prior to the systolic peak, the index would be negative.

Figure 14:
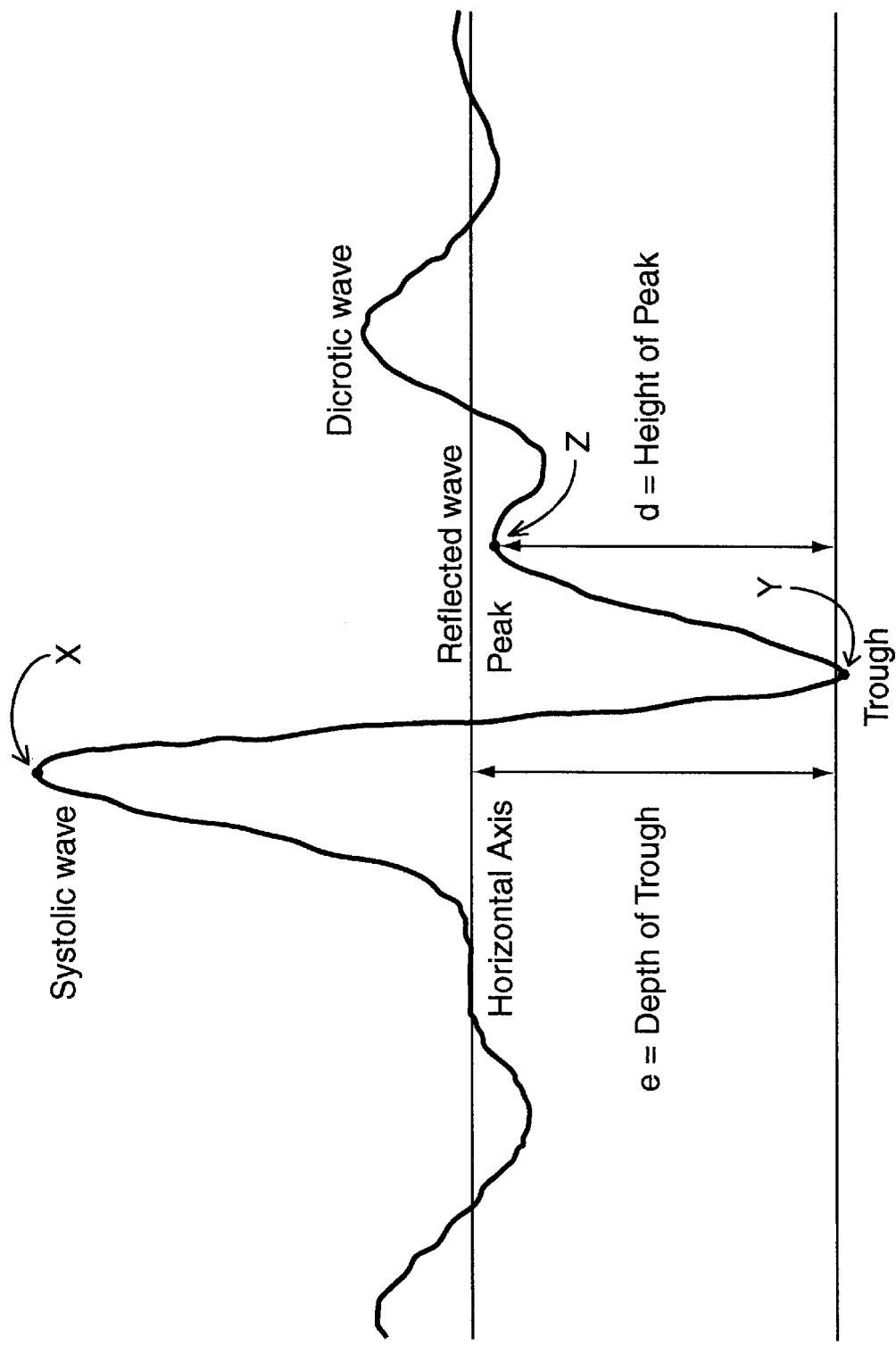
FIG. 14 is a graph showing the derivation of the measure $INDEX_{2nd\ Deriv}$.

3. As shown in FIG. 14, $INDEX_{2nd\ Deriv}$ is derived from the second derivative of the DVP signal (as shown in FIG. 10C). In the second derivative there is an initial peak (at X) followed by a deep trough (at Y) followed by a second peak (at Z). The ratio of the height (d) of the second peak (at Z) relative to the distance from the horizontal axis to the nadir or the depth (e) of the deep trough (at Y), is related to the amplitude and timing of the reflected wave. Accordingly, $INDEX_{2nd\ Deriv}$ is the percentage ratio: $d/e*100\%$ (FIG. 14). Since the larger systolic wave precedes the smaller systolic reflected wave, the closer the systolic reflected wave peak is to the systolic wave peak, the greater the amplitude of the systolic wave will be.

As disclosed in U.S. Pat. No. 4,432,374 to Osanai, second derivative indices can be used to discern cardiovascular health. Twice differentiated PPG signals are indicative of blood circulation whose interpretation effectively leads to a diagnosis of the entire circulatory system including early signs of malfunction. Analysis of the second derivative of the DVP signal allow for detection of presymptoms of arteriosclerosis, myocardial infarction, cerebral apoplexy, subarchnoidal hemorrhage, etc. is possible.

The extent of upward deflection of the DVP contour caused by the systolic reflected wave depends on its proximity to the masking influence of the larger systolic wave. A smaller upward inflection of the systolic wave occurs if there is a relatively small delay between the systolic and systolic reflected wave peaks. This will result in the height (d) of the second peak (at Z) in the second derivative being relatively less. The specific correlation between $INDEX_{2nd\ Derriv}$ and the systolic reflected wave and thus the aortic transit time of the reflected wave is useful in determining various cardiovascular measures. $INDEX_{2nd\ Deriv}$ also correlates well with beat to beat blood pressure and longer term aortic pulse wave velocity changes.

As previously discussed, aortic pulse wave velocity is an indirect but reliable measure of aortic compliance and a powerful measure of cardiovascular health and relative risk. Once aortic pulse wave velocity has been determined and the components of the DVP contour have been identified, conventional methods can be used to determine a number of diagnostic values including mean blood pressure, blood pressure, respiratory rate and rhythm, sleep apnea, and autonomic function, and aortic compliance as will be described.

Figure 15A:
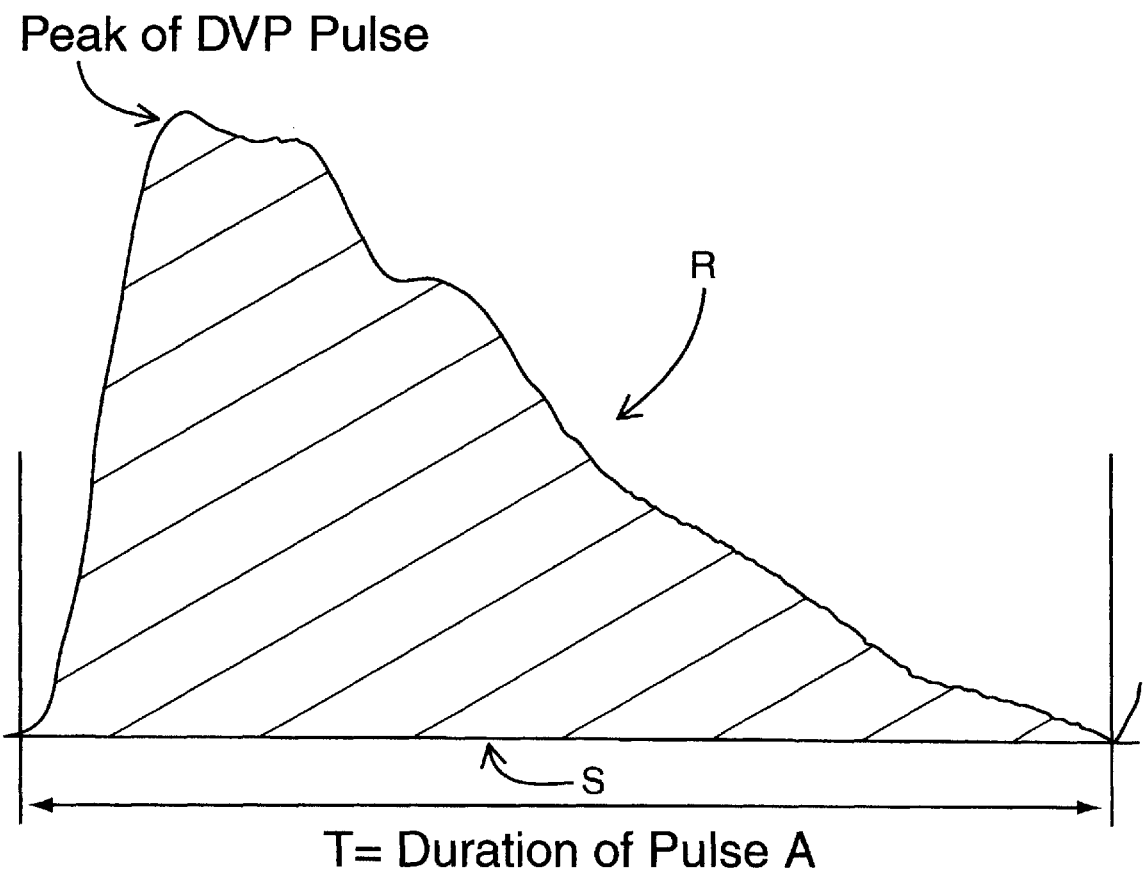
FIG. 15A is a graph showing the derivation of the mean blood pressure.

FIG. 15A illustrates how mean pulse amplitude of the DVP signal can be determined. First, the DVP signal must be temperature normalized and have respiratory variations removed, as previously discussed. The area between such a DVP signal (R) and the diastolic signal amplitude (S) is measured for the duration of a heartbeat and that value is divided by the duration of the heartbeat or pulse (T) as shown graphically in FIG. 15A. The mean pulse amplitude of the DVP signal will fluctuate with blood pressure, that is, as blood pressure rises, the DVP signal will show proportional changes. Accordingly, it is possible to use the mean pulse amplitude value of the DVP signal as a correlate of mean blood pressure, and in this way blood pressure changes can be monitored by system 10.

An accurate correlate of the pulse pressure (i.e. the difference between systolic and diastolic pressure) can also be derived from the maximum and the minimum excursion of the DVP signal R. Thus, the combination of pulse wave velocity and analysis of the DVP signal contour can give a better estimate of blood pressure than either one alone. Once calibrated with a conventional blood pressure cuff, the pressure pulse contour in association with a knowledge of pulse wave velocity can be used to follow actual systolic and diastolic blood pressure readings. Without such calibration it is only possible to track not changes in blood pressure through observation of the mean volume pulse amplitude, the augmentation index and reflected wave changes.

Once aortic pulse wave velocity has been determined, it is possible to convert a temperature stabilized volume pulse contour signal into an accurate pressure pulse contour for ongoing monitoring of blood pressure using conventional techniques. While pulse wave velocity is an accurate way of tracking mean arterial blood pressure, it does not accurately correlate with pressures on either side of the mean (i.e. the systolic or diastolic pressures).

As previously discussed in relation to FIG. 15A, the mean value of the DVP contour can be found by taking the area above the diastolic amplitude, under the DVP contour from the beginning of one beat to the beginning of the next and dividing it by the time duration of the beat. To derive the value for systolic and diastolic blood pressures through observation of the excursion of the DVP signal from its mean, it is essential to understand the relationship of arterial volume change to arterial pressure change. It should be noted that the DVP signal cannot be used to determine mean blood pressure directly, since the raw PPG signal is high pass filtered before being amplified which removes the baseline amplitude of the PPG signal. Thus, it is necessary to use a volume independent measure of mean blood pressure, such as pulse wave velocity to derive systolic and diastolic values.

The DVP contour has an amplitude differential between the systolic and diastolic values ($DVP_{diff}$) that varies in a nonlinear way with the arterial pulse pressure (PP) (i.e. the difference between arterial systolic and diastolic pressure). The relationship between arterial pulse pressure (PP) and $DVP_{diff}$ varies between users as well. The DVP contour has a significantly different shape than the pressure pulse contour. The peaks of the DVP signal are much less defined and this results in the DVP signal having a different mean amplitude than the pulse pressure contour. The difference in shape occurs because of the diffusion of light in the finger as it travels from the light source, through tissue to arterial elements and back to the photodetector. This diffusion smooths the shape of the DVP signal relative to the pressure pulse contour. In order to better relate the shape of the DVP signal to the arterial pressure pulse contour, it is possible to synthesize a pressure pulse contour ($RADIAL_{synth}$) from the DVP signal, through the use of a transfer function applied to the DVP signal, as will be described.

It has been observed that the amplitude of the synthesized radial pressure pulse contour ($RADIAL_{synth}$) will vary with the amplitude of the DVP signal in a nonlinear fashion. This is evident from the equation which relates arterial pressure change to fractional volume change:

$$\Delta P = K * C^2 * \frac{\Delta V}{V}$$

where AP is a change in pressure in mmHg, K is a calibration constant, C is pulse wave velocity, and V is arterial volume. The sensing of a blood volume using a PPG device involves the scattering of light within the finger and makes it difficult to rely on the formula above alone to derive arterial pulse pressure (PP) from the DVP contour.

U.S. Pat. No. 5,265,011 to O'Rourke discloses one technique of transforming a radial artery pressure pulse contour into an aortic pressure pulse contour through use of time domain or frequency domain techniques. A transfer function is derived through examination of sample data obtained invasively from the aorta and noninvasively from the radial artery. A similar approach is utilized in "On-line Synthesis of the Human Ascending Aortic Pressure Pulse From the Finger Pulse", Mastafa Karamanoglu et al., Hypertension, Vo. 30, No. 6 December 1997 pgs. 1416–1424. The change in shape from the volume pulse contour as seen in a finger to a pressure pulse contour seen in the radial artery can be described by a transfer function calculated from data obtained from a tonometric and PPG apparatus for a particular user.

The method of the present invention is to determine the nonlinear relationship between a particular user's blood pressure and their pulse wave velocity. This method accomplishes calibration of this nonlinear relationship by observing the blood pressure and aortic or digital pulse wave velocity together over a significant range of values. Once a set of values representing the simultaneous changes in blood pressure and pulse wave velocity is obtained, a conventional polynomial best fit curve fitting algorithm can be used to derive an equation that can be used later to predict blood pressure from pulse wave velocity alone. As long as the aortic or digital pulse wave velocity correlate (i.e. indices based on the shape and timing of a reflected wave) varies closely with mean blood pressure, the calibration curve will permit accurate subsequent measurements using only readings of a user's pulse wave velocity.

Specifically, the method of calibration involves simultaneous collection of pulse wave velocity and blood pressure samples over a period of time as blood pressure varies significantly. The sample data from a PPG sensor 12 attached to a finger and a tonometric apparatus applied to the radial artery can be used to create a transfer function for the user. The calibration curve, obtained from the polynomial curve fitting algorithm, can be used without need for recalibration for a matter of months. Recalibration is necessary only to account for aging effects on the arterial system.

Figure 15B:
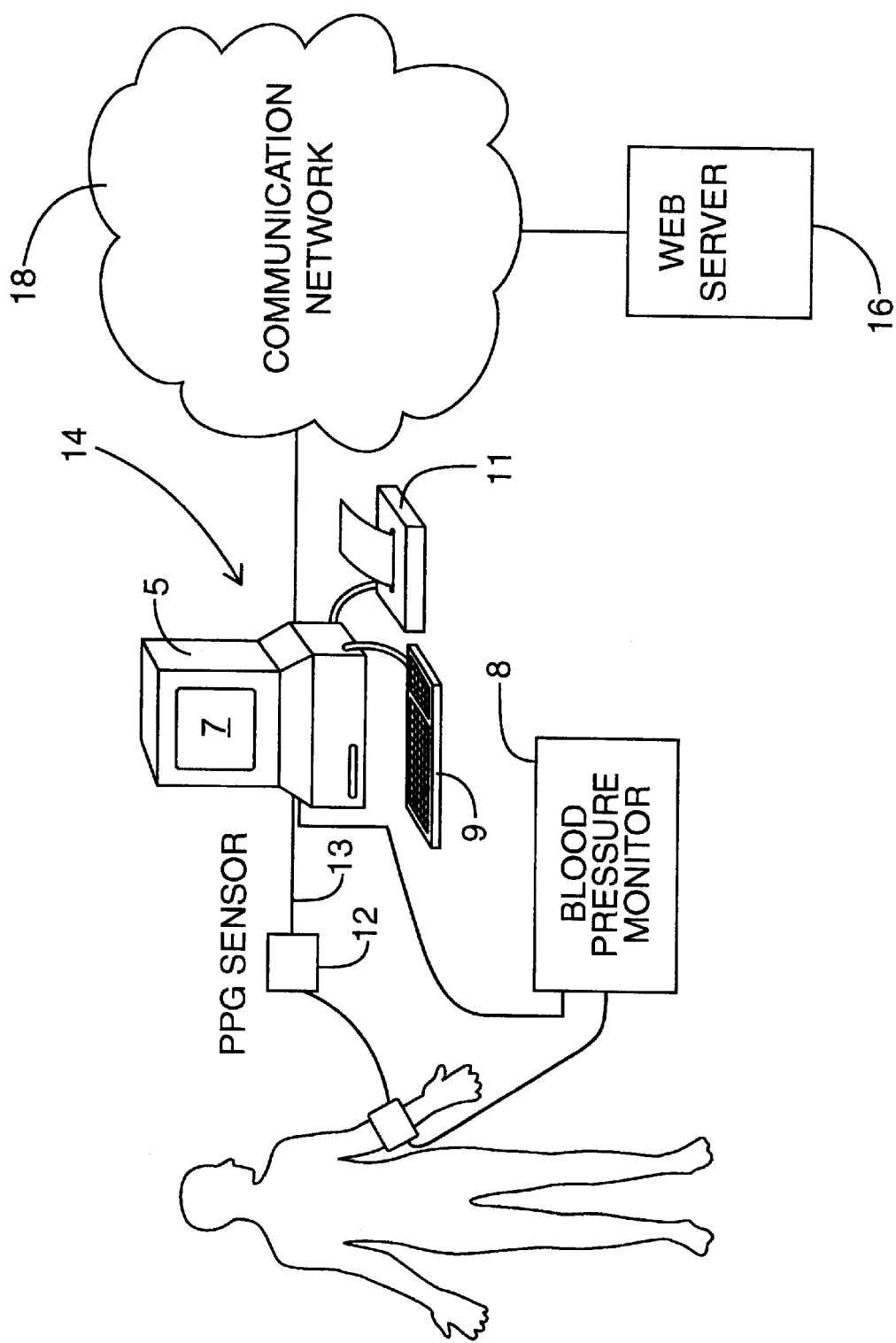
FIG. 15B is an illustration of the physiological signal monitoring system of FIG. 1 as used in association with a blood pressure monitor.

As shown in FIG. 15B, a continuous noninvasive blood pressure monitor 8, such as the Colin model 7000 blood pressure monitor (available from Colin Medical Instruments Corp. of Texas) could be used alongside PPG sensor 12 of system 10 for calibration purposes. The unit is a wrist worn device that initially calibrates itself against a reading from an integral cuff blood pressure device. Thereafter, readings from the arterial tonometer can be used by system 10 to give accurate beat to beat readings of absolute blood pressure. Specifically, the PPG signal detected by PPG sensor 12 can be used in association with the blood pressure and pressure pulse contour information from the Colin 7000 to provide a user with various blood pressure measures.

Alternatively, it should be noted that digital pulse wave velocity could be used in place of aortic pulse wave velocity. Aortic pulse wave velocity is about one half that of digital pulse wave velocity, and accordingly, since there is a linear relationship between aortic and digital pulse wave velocity, the calibration process will produce an analogous curve using digital pulse wave velocity. Accordingly, it would be possible to implement blood pressure monitor 8 by the finger cuff bladder 29 (FIG. 4) in association with Penaz techniques as previously discussed to achieve similar calibration. In this case, the digital arterial pressure, not the radial arterial pressure would be the calibrating parameter.

The rise and fall of blood pressure, on a beat to beat basis, in association with respiration is the simplest way to measure blood pressure and pulse wave velocity over a small range of values. Raising an arm and rising from a sitting position are ways to provoke larger changes in blood pressure at the wrist. In this way, it is possible to simultaneously sample blood pressure and pulse wave velocity enabling the derivation of the nonlinear relationship between these parameters for a particular user. It should also be noted that a generalized transfer function could also be used without individual calibration. However, for better accuracy, it is desirable to create individual transfer functions through a sampling of each user's DVP signal and radial tonometric signals.

The calibration procedure described above will provide a relationship curve that describes the nonlinear relationship between a user's (either aortic or digital) pulse wave velocity and blood pressure. It should be understood that any index that varies closely with aortic or digital pulse wave velocity can be used to derive a nonlinear relationship between the index and blood pressure. Most of the indices discussed above (e.g. $\Delta T_{Ref}$, $INDEX_{Ref}$, and $INDEX_{2nd\,Deriv}$) can be used for this purpose. Previous methods such as that disclosed in U.S. Pat. No. 5,265,011 to O'Rourke and U.S. Pat. No. 5,882,311 to O'Rourke both disclose the conversion of a digital pressure pulse contour into an aortic pulse pressure contour using a transfer function which is derived on the basis of blood pressure pulses obtained from remote sites. The amplification and phase differences between the two pressure pulse contours are measured by appropriate signal analysis and processing techniques. In such a method the transfer function is developed on the basis of remotely measured blood pressure pulses and aortic blood pressure. In contrast, the present invention discloses the development of a calibration curve between blood pressure volume indices and aortic blood pressure.

Figure 15C:
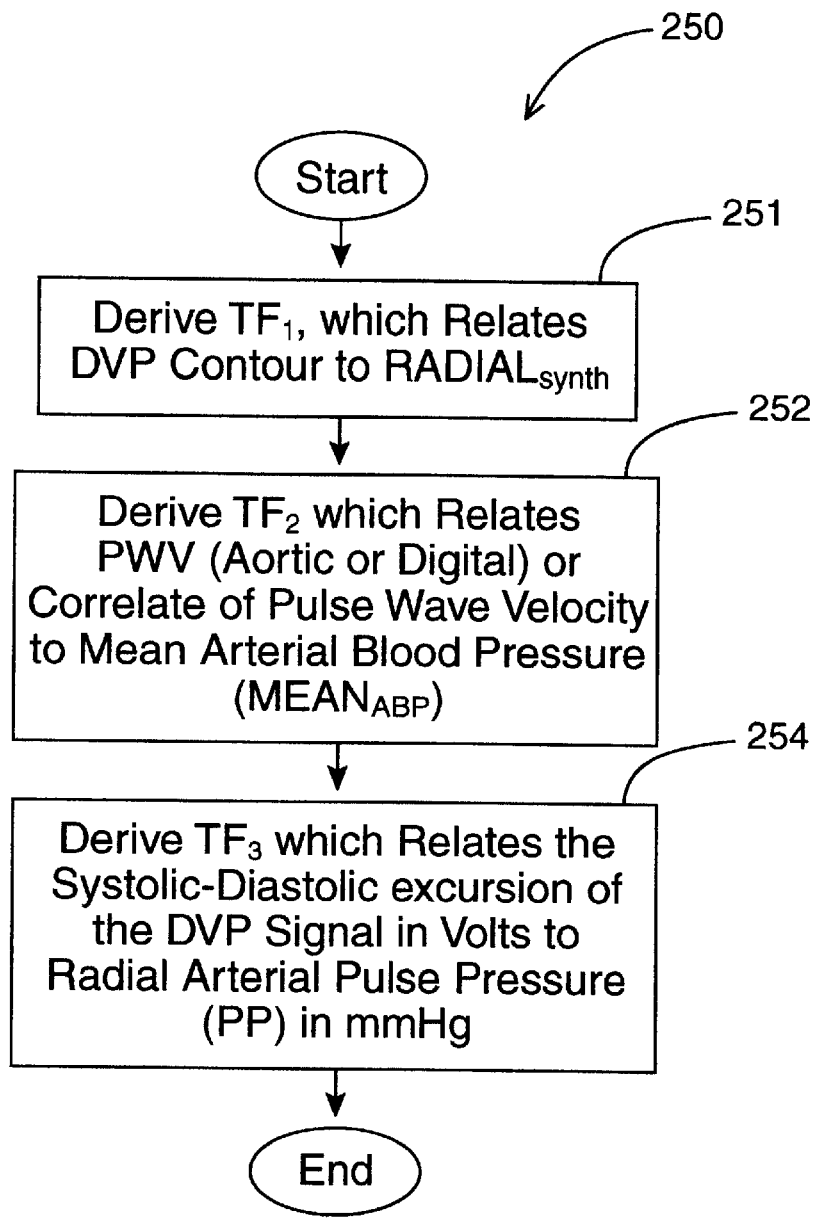
FIG. 15C is a flow chart illustrating of the calibration method of the present invention which obtains transfer functions which relate measures from a user's DVP signal pulse to a pulse pressure contour, mean arterial blood pressure and radial arterial pulse pressure.
Figure 15D:
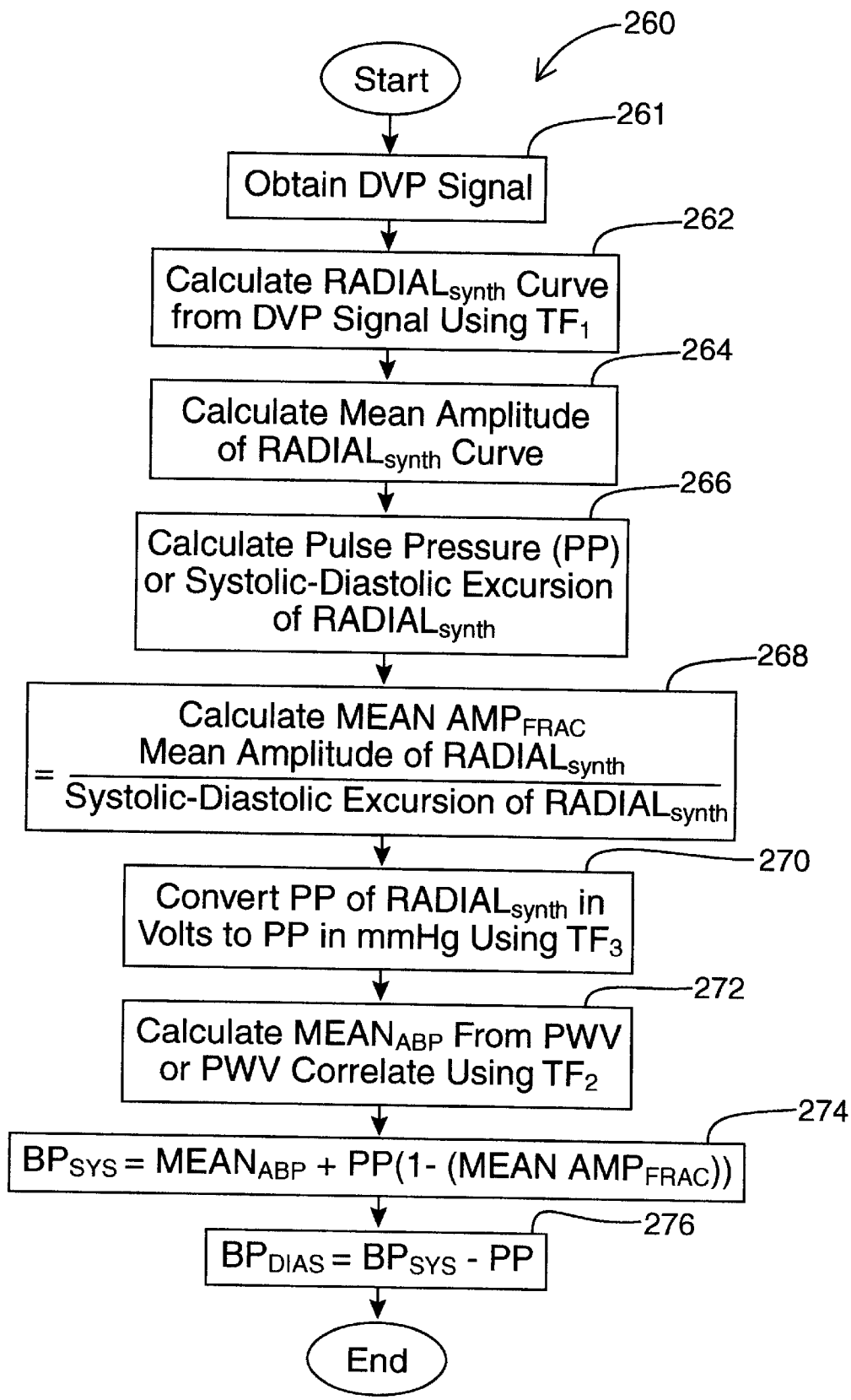
FIG. 15D is a flow chart illustrating the blood pressure determination method of the present invention which derives a user's systolic, diastolic and pulse pressure from the user's DVP contour using the physiological signal monitoring system of FIG. 15B.

FIGS. 15C and 15D together show the steps taken to determine the systolic blood pressure ($BP_{sys}$) and the diastolic blood pressure ($BP_{dias}$) of a user according to the calibration method 250 and the blood pressure determination method 260 of the present invention.

Referring first to FIG. 15C, the calibration method 250 consists of the derivation of a number of transfer functions using a commercial continuous non-invasive blood pressure monitor 8 (FIG. 15B) such as the Colin 7000 that generates a radial pressure pulse contour on a beat to beat basis. Alternatively, the integrated bladder and servo controller pressure device 29 discussed in association with FIG. 4 could be used for an analogous purpose. By continuously measuring the blood pressure of a user as discussed above, it is possible to obtain a number of transfer functions (or calibration curves) for a user between various cardiovascular measures, as will be described.

Specifically, a transfer function $TF_1$ is derived (251) which converts a user's DVP contour to a synthesized radial pulse contour $RADIAL_{synth}$ by monitoring the relationship between a user's DVP signal and a user's pressure pulse contour. The transfer function $TF_1$ is derived using a commercial continuous non-invasive blood pressure monitor 8 to generate a radial pressure pulse contour on a beat to beat basis. As discussed above the integrated bladder and servo controller pressure device 29 could be used in the alternative.

Next, a transfer function $TF_2$ is derived (252) which converts a measure of pulse wave velocity (e.g. aortic or digital) or a correlate of aortic pulse wave velocity such as $INDEX_{Ref}$, $INDEX_{2nd\ Deriv}$, or $\Delta T_{Ref}$ to the user's mean arterial blood pressure. The transfer function $TF_2$ is derived using blood pressure monitor 8 and the PPG sensor 12 and CPU 5 of processing device 14 while having the user perform actions that result in significant swings in mean blood pressure. The values for mean blood pressure and pulse width velocity are correlated by using a polynomial best fit curve algorithm.

Finally, a transfer function $TF_3$ is derived (254) that relates the systolic to diastolic excursion of the DVP signal to a user's radial arterial pulse pressure. Again, transfer function $TF_3$ is obtained using blood pressure monitor 8 in conjunction with PPG sensor 12 and CPU 5 of processing device 14. Values for the systolic to diastolic excursion of the DVP signal are plotted against corresponding radial arterial pulse pressure values. The values are correlated by using a polynomial best fit curve algorithm.

Once the calibration method 250 has been performed and the transfer functions $TF_1$, $TF_2$, and $TF_3$ are stored by CPU 5 of processing device 14, the user may then proceed to use system 10 independently of blood pressure monitoring device. Each time the user requests information concerning blood pressure measures, system 10 will execute a routine which applies blood pressure determination method 260.

FIG. 15D shows the process steps of blood pressure determination method 260. First, a user's DVP signal is obtained (261) as has been previously discussed. Then the synthesized radial pulse contour ($RADIAL_{synth}$) is calculated (262) from the user's DVP signal using transfer function $TF_1$ which was obtained as described above. Then the mean amplitude of the synthesized radial pulse contour ($RADIAL_{synth}$) is determined (264) by taking the area under the synthesized radial pulse ($RADIAL_{synth}$) from the upstroke of one beat to the next and dividing this by the duration of the beat. Also, the pulse pressure (PP) or systolic to diastolic excursion of the synthesized radial pulse contour ($RADIAL_{synth}$) (i.e. the difference between the systolic and diastolic amplitudes of ($RADIAL_{synth}$)) is calculated (266).

The mean amplitude of the synthesized radial pulse ($RADIAL_{synth}$) is divided by this systolic to diastolic excursion (268). This expresses the mean amplitude as a fraction of the amplitude differential (MEAN $AMP_{Frac}$). For example, in the case where mean pressure is 100 mmHg, the systolic pressure is 140 mmHg and the diastolic pressure is 80 mmHg. The pulse pressure (PP) would then be equal to 140 mmHg–80 mmHg or 60 mmHg. Mean pressure lies 20 mmHg above the diastolic pressure and is $20/60$ or $1/3$ of the pulse pressure (PP).

Next, the systolic to diastolic amplitude differential of synthesized radial pulse contour ($RADIAL_{synth}$) in volts is converted to a pulse pressure (PP) in mmHg (270) through the use of transfer function $TF_3$. That is, the amplitude of the pulse pressure (PP) of the synthesized radial pulse ($RADIAL_{synth}$) measured in volts is converted to a pulse pressure (PP) in mmHg. The derived function relates the systolic to diastolic excursion of the DVP contour to that (i.e. the pulse pressure (PP)) of the radial artery.

Mean arterial blood pressure $MEAN_{ABP}$ is then calculated from either digital or aortic pulse wave velocity (or a pulse wave velocity correlate) (272) using transfer function $TF_2$. It should be noted that mean arterial blood pressure $MEAN_{ABP}$ could be obtained using such a transfer function applied to any correlates of aortic pulse wave velocity such as $INDEX_{REF}$, $INDEX_{2nd\ Deriv}$, or $\Delta T_{REF}$ (as discussed above).

Utilizing these three different transfer functions $TF_1$, $TF_2$, and $TF_3$, it is possible for system 10 to provide a relatively accurate estimation of these various blood pressure measures. Systolic blood pressure ($BP_{sys}$) can be calculated (274) according to the relation:

$$BP_{sys} = MEAN_{ABP} + PP(1 - (MEAN\ AMP_{Frac}))$$

Diastolic blood pressure ($BP_{Dias}$) is then calculated by subtracting the calculated pulse pressure (PP) from systolic blood pressure ($BP_{sys}$) (276).

As mentioned above, it is contemplated that system 10 can be calibrated with a sophisticated noninvasive blood pressure monitor such as the Colin 7000. It is anticipated that users would perform the calibration at a point of purchase location (i.e. similar to cell phone setup at a dealer before the cell phone can be used). The alternative, discussed above would be to integrate system 10 with an inflatable cuff 29 so that blood pressure can be measured continuously allowing for a separate calibration unit and allowing for frequent calibration during the use of system 10.

It is also possible for users to follow trends (or changes) in blood pressure through the examination of the pulse wave velocity alone without calibration. This would provide a user with a general sense of their blood pressure and information on blood pressure changes could be used within a biofeedback model to assist user's lower their blood pressure levels. The indices described above, namely $\Delta T_{Ref}$, $INDEX_{Ref}$, and $INDEX_{2nd\ Deriv}$ can also be generated directly from the DVP signal and used as general indicators for cardiovascular health on their own.

The aortic pressure pulse contour provides valuable information about the pressures the heart is pumping against. Typically there is a substantial discrepancy between the pressure profile measured with a blood cuff on the arm and the aortic pressure profile. The pressure pulse contour, once calibrated against an arm blood pressure reading taken simultaneously, can be used to determine systolic and diastolic pressures thereafter. Having a peripheral pressure pulse contour synthesized from the volume pulse contour permits the synthesis of the aortic pressure pulse contour. A generalized transfer function can be created to derive the aortic pressure pulse contour as demonstrated by the authors of the article "Functional Origin of Reflected Pressure Waves in a Multibranched Model of the Human Arterial System", Mustafa Karamanoglu et al., The American Physiological Society (1994) H1681 to H1688.

It is also possible to estimate the respiratory contour using the DVP signal and it characteristics. Specifically, $INDEX_{Ref}$ (DVP augmentation index), $\Delta T_{REF}$, $INDEX_{2nd\ derriv}$, mean DVP amplitude and other cardiovascular indices vary with beat to beat changes in aortic pulse wave velocity. This is due to changes in blood pressure associated with respiration. It is known that during respiration, there are synchronous periodic fluctuations of the volume of blood in all body compartments, primarily on account of mechanical pressure and pumping action.

Changes in pulse wave velocity are highly correlated with obstructed respiratory effects, such as those apparent with sleep apnea. With each inspiration, mean blood pressure falls. Thus, by following mean blood pressure, it is possible to obtain the respiratory rate and depth of respiration. Pulse wave velocity (both digital and aortic), $INDEX_{Ref}$, adaptively filtered reflected wave timing and amplitude, $INDEX_{2nd\ Deriv}$, $\Delta T_{Ref}$ and mean blood pressure derived from the area under the DVP signal can all be used to follow mean blood pressure and thus to synthesize respiratory rate and the depth of respiration.

Figure 16A:
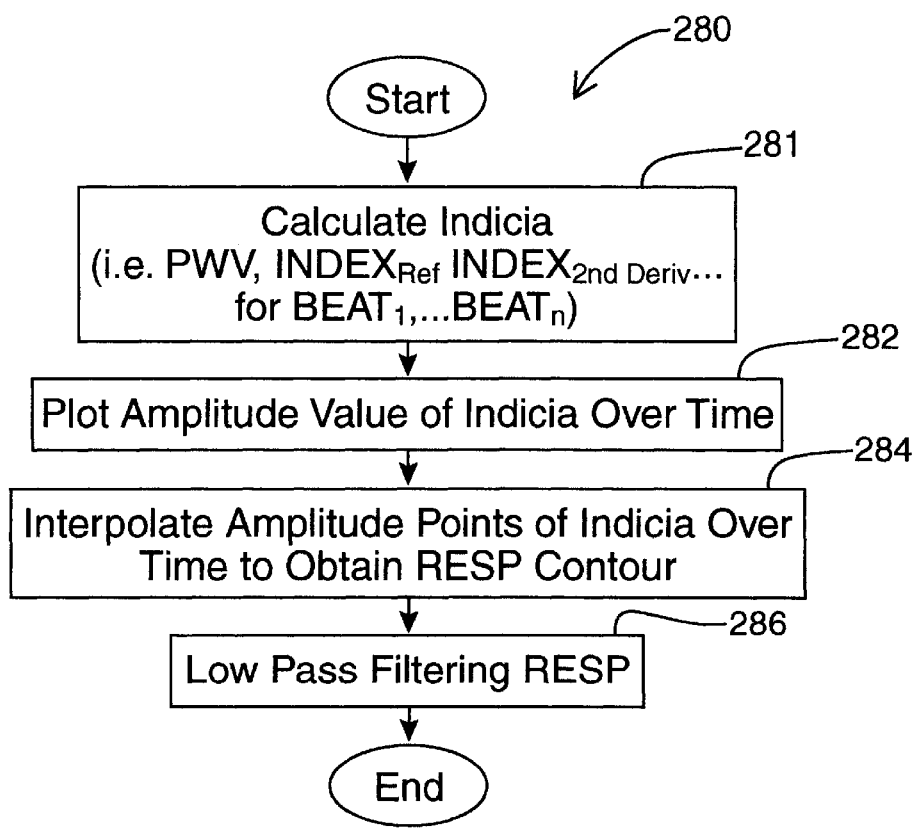
FIG. 16A is a flow chart illustrating the steps for obtaining a respiratory contour for a user using a cardiovascular parameter obtained from a user's DVP signal.
Figure 16B:
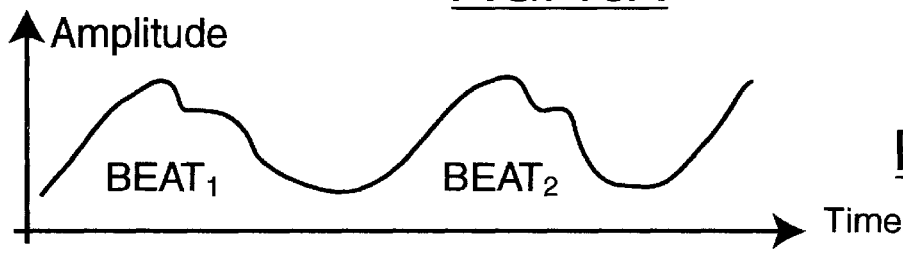
FIG. 16B is a graphical representation of a user's DVP signal.
Figure 16C:
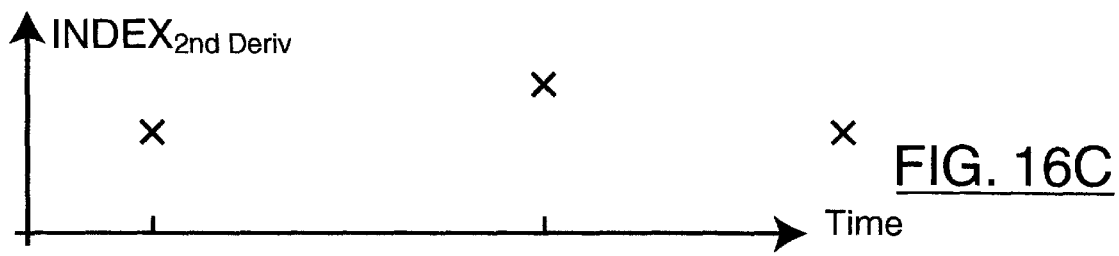
FIG. 16C is a graphical representation of the $INDEX_{2nd\ Deriv}$ values obtained for each BEAT of the DVP signal of FIG. 16B.
Figure 16D:
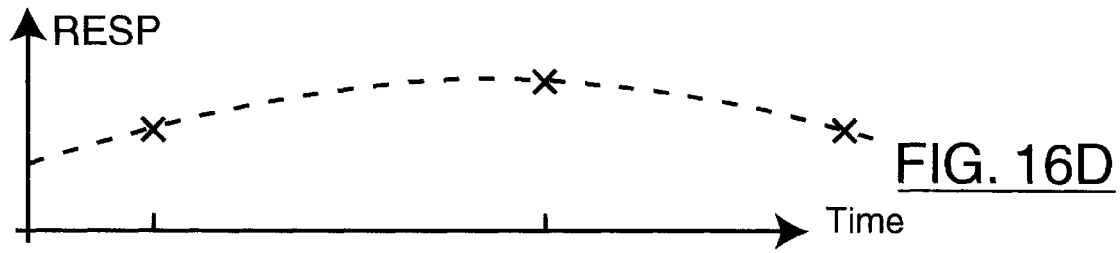
FIG. 16D is a graphical representation of a typical respiratory contour, RESP, obtained from interpolating the $INDEX_{2nd\ Deriv}$ values.

As shown in FIGS. 16A, 16B, 16C and 16D a respiratory contour, RESP, can be synthesized by observing the beat to beat changes in pulse wave velocity and low pass filtering the signal derived from each of the indices. Specifically, in FIG. 16A CPU 5 of processing device 14 performs the calculation (281) of a particular physiological indicia, such as $INDEX_{2nd\ Deriv}$ over the course of a number of DVP beats $BEAT_1, \ldots BEAT_n$. Then, the amplitude of the indicia is plotted over time (282). Using a conventionally known polynomial curve fitting algorithm, it is possible to interpolate between data points (284) and to produce an approximately fitted curve for the respiratory contour RESP as shown in FIG. 16D. Finally, the respiratory contour RESP is low pass filtered (286) at a corner frequency of approximately 0.5 Hertz to remove spurious noise from the signal.

The depth of the fall in blood pressure with inspiration can be used to monitor for respiratory obstruction, since the inspiratory effort will increase with obstruction, resulting in a greater inspiratory fall in blood pressure. Sleep apnea is a condition affecting many people and its diagnosis is difficult, requiring analysis of breathing patterns during sleep in a sleep laboratory. By programming system 10 to monitor the augmentation index, or another blood pressure indicator, it is possible to determine if a person is at risk for sleep apnea and to follow treatment effects. For example, a glove worn PPG sensor 12 communicating with processing device 14 provides this functionality to users (not shown).

Further, the autonomic nervous system influences the PPG signal and can provide information about the health of a user autonomic nervous system. Very low frequency changes in the nonpulsatile and pulsatile portions of the PPG signal can be detected through spectral analysis techniques. These low frequency changes are associated with autonomic nervous system influences and can provide information about the health of the autonomic nervous system.

As discussed, pulse wave velocity varies with blood pressure and can be used as a correlate to track mean blood pressure. Because blood pressure is under the control of the autonomic nervous system, subtle changes in autonomic function can be discerned by tracking blood pressure changes during particular types of physical movement. For example, those individuals with a family history of diabetes but who have not exhibited any clinical changes in blood sugar will exhibit abnormalities indicative of diabetic autonomic neuropathy. Examining pulse wave velocity when the user stands up can reveals these autonomic changes. An unaffected person will have little change in pulse wave velocity while an affected person will show a significant drop in pulse wave velocity, associated with a drop in blood pressure, on standing up.

Aortic compliance is a powerful indicator of cardiovascular health and cardiovascular risk. As discussed previously, many authorities have observed that aortic compliance and carotid artery compliance is closely related to age and that vascular compliance is more closely related to physiological age than other measures such as skin inelasticity, greying of hair, baldness, etc. There is also evidence that aortic compliance is related to hypertension, cardiac function, and left ventricular hypertrophy and can be increased by exercise, hormonal therapy; antioxidant and antihypertensive treatment. It has been proposed that deviation of aortic compliance from the age-predicted norm may prove to be a good predictor of cardiovascular pathology ("Vascular Compliance as a Measure of Biological Age", Christopher J. Bulpitt et al., JAGS June 1999—Vol. 47, No. 6 pgs. 657–663). Also, aortic compliance was found to be significantly reduced in patients with stoke compared with non-stroke control subjects ("Aortic Distensibility in Patients with Cerebrovascular Disease", E. D. Lehmann et al., Clinical Science (1995) 89, pgs. 247–253).

Pulse wave velocity is an indirect measure of aortic compliance. In fact, studies have shown that aortic pulse wave velocity is strongly associated with the presence and extent of atherosclerosis and constitutes a forceful marker and predictor of cardiovascular risk in hypertensive patients ("Aortic Pulse Wave Velocity as a Marker of Cardiovascular Risk in Hypertensive Patients", Jacques Blacher, et al., Hypertension, May 1999, pgs. 1111–1117). Through the use of correlates of aortic pulse wave velocity discussed above, system 10 can provide an accurate assessment of cardiovascular risk for a user quickly and easily.

As previously discussed, PPG sensor 12 can utilize one or two LED's. While the PPG sensor 12 of the preferred embodiment of the invention includes two LED's it is possible to conduct the above noted analysis and obtain the above noted cardiovascular indices using just a single LED. However, it is only possible to obtain the measurement of blood oxygen saturation using a red $LED_1$ and an infrared $LED_2$ as will be discussed.

Blood oxygen saturation is a physiological parameters of critical importance in many medical conditions. The non-invasive measurement of arterial oxygen saturation using PPG sensors known as pulse oximetry is well established in clinical use. The technique relies on the knowledge that haemoglobin and oxygenated haemoglobin absorb incident light to varying degrees as a function of wavelength.

In particular, at 658 nanometres (which corresponds to red light), the absorption coefficient for haemoglobin is ten times higher than that for oxyhemoglobin. At 880 nanometres (which corresponds to infrared light), there is a much smaller difference between the absorption coefficients between the two wavelengths. It is thus possible to derive the proportion of oxyhemoglobin and therefore the arterial oxygen saturation from a knowledge of the absorption characteristics of the arterial blood at these two wavelengths. That is, differential absorption of oxyhemoglobin and deoxyhaemoglobin at these two wavelengths allows the relative proportion of each to be determined as is well known to those skilled in the art of biomedical engineering.

Alternatively, it would be possible to use two infrared LEDs which are close to the isobestic point of haemoglobin (i.e. approximately 880 nanometres). The isobestic point of haemoglobin is defined as being the wavelength at which the haemoglobin is relatively insensitive to the oxygenated status of the haemoglobin molecule. Light emitting at 880 nanometres is close to the point where the absorption of light by haemoglobin is not affected by the oxygenation status of the haemoglobin molecule.

Further, by using PPG sensor 12 with two LEDs, an accurate measure of digital pulse wave velocity can be made as the pulse wave travels between the two LED's. Conventional methods for measuring pulse wave velocity have utilized a between-LED spacing of at least 3 centimeters, such as in U.S. Pat. No. 5,309,916 to Hatschek. The most common way of measuring pulse wave velocity from PPG signals is to measure the time from the "foot" of one signal pulse to the "foot" of the other signal pulse. The "foot" of the signal is relatively free from distortions introduced by local reflection phenomena. The rest of the pulse contour is distorted slightly because of local reflection effects.

It has been observed that for signals originating from light sources 1 centimeter apart, the time delay of the DVP contour will be approximately 1 millisecond. In order to sample this interval with 1:1000 accuracy, it is necessary to sample the volume pulse contour at a frequency of 1 megahertz. Currently, this sampling speed can only be obtained with specialized data acquisition boards and accordingly, is not particularly suitable for conventional personal computing means.

The present invention can provide accurate DVP waveform analysis at sampling rates as low as 200 hertz (although a sampling rate of 1 kilohertz is preferable) has been found to provide sufficient through the use of cross correlation (CC) analysis. Processing device 14 determines the time delay between the volume pulse contour as it passes between the two LEDs of PPG sensor 12 using CC analysis. CC provides information on the degree of correlation between two signals according to the well known formula of CC:

$$CC(\tau) = \int^{+\infty} V_1(t)V_2(t-\tau)dt$$

CC is a function of the parameter τ, the lag between $V_1$ and $V_2$. This CC relation can be used by processing device 14 to calculate time delay from which pulse wave velocity can be estimated. Cross correlation of two PPG signals has traditionally resulted in several inaccuracies due to local reflection effects. It has been determined that by filtering out those parts of the volume pulse contour signal that are associated with reflection effects, it is possible to appreciably decrease reflection effects. Specifically, by high pass filtering the volume pulse contour (e.g. above 8 Hertz and preferably above 10 Hertz) prior to cross correlation, it has been observed that the corrupting effects of reflection effects on the volume pulse contour signal can almost be completely eliminated.

Another method of reducing reflection effects is to use an adaptive predictor which requires the use of complex algorithms. This method requires significant calculation on a real time basis and takes a large number of samples before making an accurate result. A third method which has been suggested is to band pass filter the volume pulse contour signal at 12 hertz and to transform the wave harmonic component at this frequency from real to complex to allow for accurate and rapid estimation of phase delay which is independent of sampling frequency.

Referring to FIGS. 1 and 16, once processing device 14 has calculated and digitized the physiological signals, it is a simple matter to convey that data to Web server 16 over communication network 18 as part of an interactive diagnostic Web site system 300. The internet Web site hosted at Web server 16 would provide service to users in possession of PPG sensor 12 appropriately integrated with their processing device 14, as well as attract visitors to the Web site through the display and description of physiological signals. Finally, the Web site would allow researchers to have access to physiological signals derived from PPG sensors 12.

Preferably the communication protocol used with the invention would be TCP/IP. Those skilled in the art will understand the manner in which the data is formatted by processing device 14 prior to being transmitted over communication network 18 to Web server 16. TCP/IP then parses the data into packets, each packet including a field indicating the destination Web site 16. Processing device 14 then outputs the packets onto communication network 18. At minimum, the packets will contain data relating to the identity of the user and an indication of the type of measurement data being is encoded within the data message. Optionally, other types of information could be provided such as the time and date of the measurement and the type of medical device which took the measurement.

The Web site hosted on Web server 16 would provide users with additional functionality for analysis, storage, and retrieval of physiological signals that they convey to the Web site. All communication of physiological data would be encrypted in a secure fashion to preserve privacy (350). The user would have the ability to store their physiological data (352) as well as text based data (354) in a personal database with access to the user in a password protected secure fashion. The medical data file maintained for the user at the Web site may be periodically updated to reflect received measurement data. Specifically, the ability of system 10 described above to recognize each individual user through the unique nature of their volume pulse contour adds an additional level of security to system 10 by establishing a database of physiological fingerprints.

Users would also be encouraged to store documentary information describing their personal health at the Web site. This would comprise a history of any medical problems they had experienced and any medications they might be taking. Other documentation describing the user, such as age, place of residence, place of birth, occupation and other demographic data would be sought. A family history of illness would be requested. Easy to use on-line forms would be available at the Web site to assist users in providing documentation.

The Web site hosted on Web server 16 could provide more sophisticated analysis means then would be possible at the user's processing device 14. The data stored by the user at the Web site on Web server 16 would be accessible to the user and health professionals authorized by the user anywhere any time. This would facilitate the exchange of medical information. Users without processing device 14 could use the database at the Web site for secure storage and retrieval of their medical documentary information.

Information stored by users in the database could be made available (as long as authorized by the user) to researchers interested in the relationship between users physiological signals and the accompanying documentation in the form of a research database (362). Analysis of the physiological and documentary information (364) from a sample of numerous users (e.g. several thousand) would be helpful in developing a medical discipline focused on the diagnosis and management of health issues through examination of physiological signals derived from a PPG sensor 12 by the research community (365).

The Web site hosted on Web server 16 could also offer third parties with educational resources (356), downloads (358) and hyperlinks to other related Web site (360). Users of system 10 could also benefit from biofeedback for relaxation and blood pressure reduction. Also, system 10 could be used to provide an index of cardiovascular risk for users seeking insurance. System 10 could also indicate an user's emotional state for purposes such as in the gaming field or as a lie detector. It could also permit access to user's medical history in emergency situations using a particular PIN or access code worn by the user.

Figure 17:
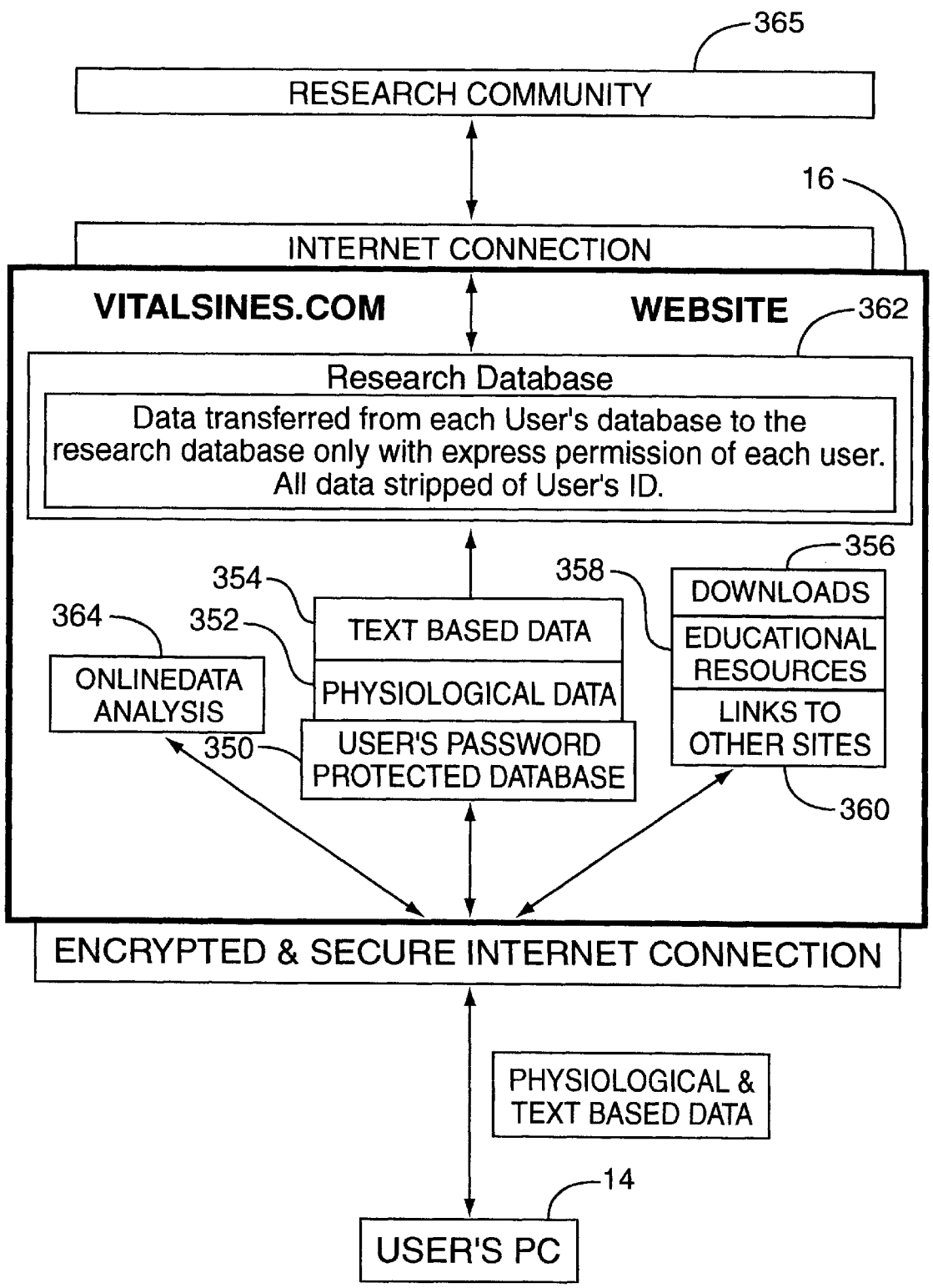
FIG. 17 is a block diagram of the physiological health monitoring system of FIG. 1 showing the functionality of the computation server.

FIG. 17 shows a contemplated biometric security system 400 according to the present invention. During the course of clinical testing of a significant number of patients, it was observed that the aortic reflected wave contour associated with a particular user is unique to that user. Specifically, the changes in the DVP signal which permits its use as a security feature are primarily related to changes in the shape and timing of the reflected wave over a period of months to years that produce a slowly changing unique shape to every user's DVP signal.

Biometric security system 400 uses the various techniques discussed above in respect of system 10 to isolate the aortic reflected wave from a PPG signal for a user 402. It is contemplated that other conventionally known techniques such as time frequency analysis could be used to characterize the aortic reflected wave from the DVP signal for pattern recognition and other security purposes.

Specifically, biometric security system 400 utilizes PPG sensor 12 and processing device 14 to obtain a user's reflected wave profile. Biometric security system 400 then uses an access controller 404 to store the user's biometric data in a biometric database 406. Access controller 404 only allows authorized person access to restricted resources 408 (e.g. bank accounts, buildings etc.) if the authorized person's aortic reflected wave profile matches one of the appropriate stored aortic reflected wave profiles stored in biometric database 406 (i.e. the aortic reflected wave profiles of authorized third parties can be stored in biometric database 406 as well).

In this way, only authorized persons would only be allowed access to resources, locations, on the basis of their particular aortic reflected wave characteristics. It is contemplated that an appropriately designed matching program would be used to compare stored aortic reflected wave profile with an aortic reflected wave that is extracted from a PPG signal obtained from the user using the PPG sensor 12 of system 10 described above. It should be noted that such a security system would have to periodically update the store aortic reflected wave profiles (e.g. every 6 months), as the aortic reflected wave profile of a user will change significantly with age.

Figure 18:
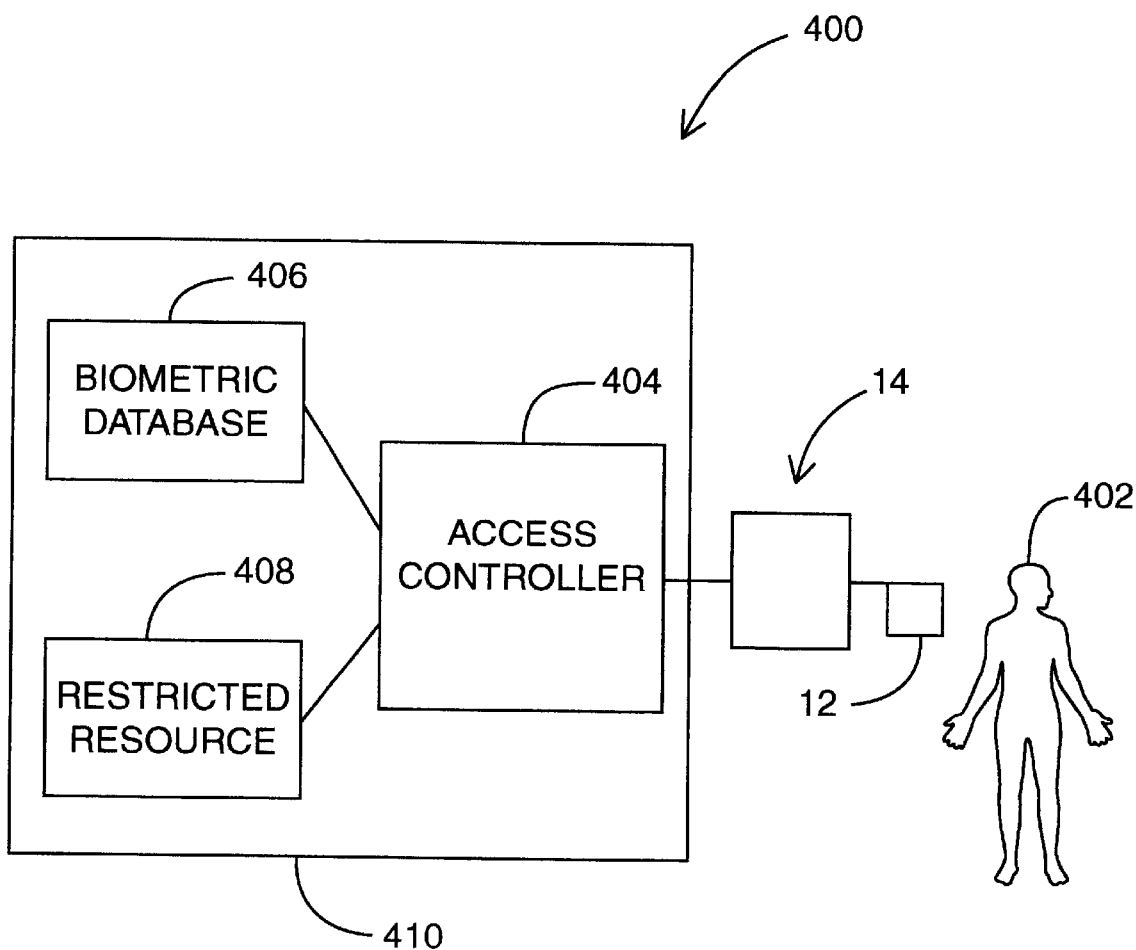
FIG. 18 is a block diagram of the biometric security system of the present invention.
Figure 19:
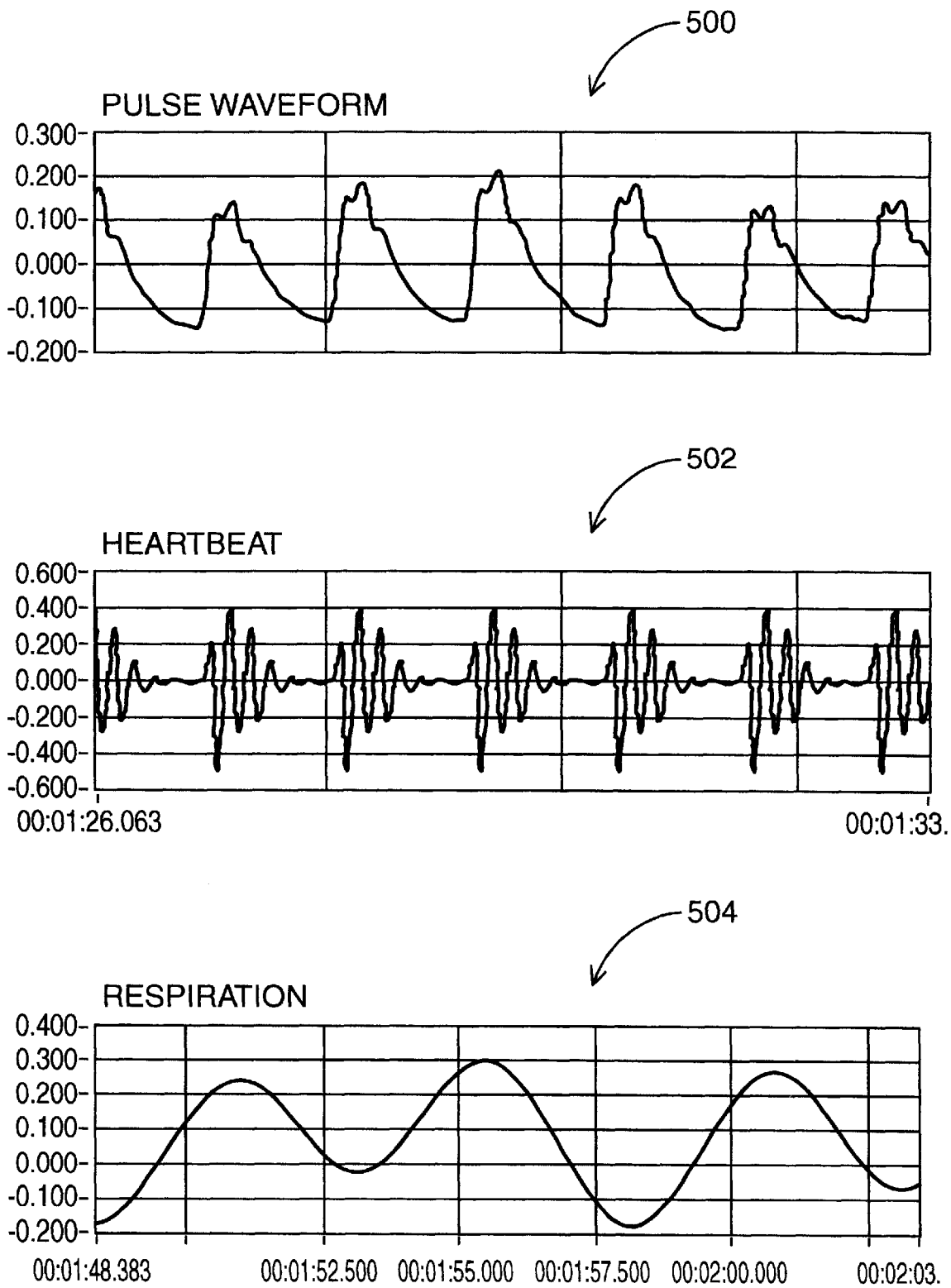
FIG. 19 is a sample screen capture of the output of the monitoring system on the display of the processing means of FIG. 1.

Finally, FIG. 18 is a sample screen capture from system 10 which provides the user with graphical information as to their own DVP waveform (500), their heartbeat (502) and their respiration contour (504).

While preferred embodiments of the invention have been described, it will be appreciated that various changes can be made within the scope of the appended claims.

I claim:

1. A physiological signal monitoring system comprising:
   (a) a PPG sensor adapted to come into skin contact with a user's body part, for sensing a physiological characteristic of the user and for generating electrical signals which correspond to said physiological characteristic, wherein said physiological characteristic comprises the user's blood volume contour;
   (b) first processing means operatively coupled to said sensor for receiving and converting said electrical signals into data, for computing a set of physiological parameters on the basis of said data and for conducting analysis of said physiological parameters, said first processing means comprising:
      (i) filtering means for filtering nonpulsatile and slowly pulsatile signals from the blood volume contour to obtain a filtered blood volume contour;
      (ii) extraction means for extracting characteristics of the user's aortic reflected wave contour from a volume contour chosen from one of the blood volume contour and the filtered blood volume contour, the characteristics of the user's aortic reflected wave contour being determined in part from a fourth derivative of said volume contour;
      (iii) computing means for determining the set of physiological parameters based on characteristics of said aortic reflected wave; and,
   (c) display means coupled to said first processing means for displaying said physiological parameters.

2. The physiological signal monitoring system of claim 1 which includes a portable device for use by the user and including the sensor and a second processing means for receiving and storing said electrical signals from said sensor, the second processing means being connectable in use to the first processing means, for transferring electrical signals to the first processing means for conversion.

3. The physiological signal monitoring system of claim 1, wherein said PPG sensor includes at least one LED.

4. The physiological signal monitoring system of claim 1, wherein said PPG sensor is operated in a reflective mode of operation.

5. The physiological signal monitoring system of claim 1, wherein said PPG sensor is operated in a transmission mode of operation.

6. The physiological signal monitoring system of claim 1, wherein said PPG sensor includes a restraining element for reducing ambient light and motion effects and for providing a predictable pressure between said PPG sensor and said body part.

7. The physiological signal monitoring system of claim 1, wherein said sensor includes a clip for mounting said sensor on a user's ear.

8. The physiological signal monitoring system of claim 1, wherein said sensor is positioned within a casing, said casing having a depression being adapted to receive the user's finger.

9. The physiological signal monitoring system of claim 1, wherein said extraction means calculates the fourth derivative of said volume contour for estimating properties of the aortic reflected wave associated with zero crossings on said fourth derivative.

10. The physiological signal monitoring system of claim 9, wherein said filtering means comprises bandpass filtering means for bandpass filtering the blood volume contour to produce the filtered blood volume contour.

11. The physiological signal monitoring system of claim 10, wherein said bandpass filtering means filters between 6 and 20 Hertz.

12. The physiological signal monitoring system of claim 1, wherein said first processing means comprises a personal computer and said display means resides with said personal computer.

13. The physiological signal monitoring system of claim 12, wherein said sensor is embedded in a keyboard of said personal computer.

14. The physiological signal monitoring system of claim 12, wherein said sensor is embedded in a mouse.

15. The physiological signal monitoring system of claim 12, wherein said sensor is embedded in a joystick.

16. The physiological signal monitoring system of claim 12, wherein said sensor is embedded in a track pad.

17. The physiological signal monitoring system of claim 12, wherein said sensor is embedded in a track ball.

18. The physiological signal monitoring system of claim 1, wherein said first processing means comprises a personal digital assistant.

19. The physiological signal monitoring system of claim 18, wherein said sensor is embedded in said personal digital assistant.

20. The physiological signal monitoring system of claim 18, wherein said sensor is embedded in a peripheral of said personal digital assistant.

21. The physiological signal monitoring system of claim 1, wherein first processing means extracts the characteristics of the user's aortic reflected wave from said data to selectively provide the user with access to a resource, said physiological signal monitoring system further comprising:
   (d) storage means for storing unique characteristics of an aortic reflected wave contour; and
   (e) verification means coupled to said first processing means and said storage means for comparing said extracted characteristics of the user's aortic reflected wave with said unique characteristics of the aortic reflected wave and for providing the user with access to the resource only if said extracted characteristics of the user's aortic reflected wave is at least substantially identical to said unique characteristics of the aortic reflected wave.

22. The physiological signal monitoring system of claim 21, wherein said verification means compares the shape and timing characteristics of said extracted user's aortic reflected wave with the shape and timing characteristics of said unique aortic reflected wave.

23. The physiological signal monitoring system of claim 21, wherein said verification means is operatively coupled to said storage means over a communications network.

24. The physiological signal monitoring system of claim 21, wherein said storage means comprises a database server.

25. A method of monitoring the physiological signals of a user comprising the steps of:
   (a) positioning a PPG sensor in close proximity to a body part of the user for sensing a physiological characteristic of the user and for generating electrical signals which correspond to said physiological characteristic, wherein said physiological characteristic comprises the user's blood volume contour;
   (b) receiving and converting said electrical signals into data and computing a set of physiological parameters on the basis of said data;
   (c) analyzing said physiological parameters according to the following steps:
      (i) filtering nonpulsatile and slowly pulsatile signals from the blood volume contour to obtain a filtered blood volume contour;
      (ii) extracting characteristics of the user's aortic reflected wave contour from a volume contour chosen from one of the blood volume contour and the filtered blood volume pulse contour, the characteristics of the user's aortic reflected wave contour being determined in part from a fourth derivative of said volume contour; and,
      (iii) determining the set of physiological parameters based on characteristics of said aortic reflected wave; and,
   (d) displaying said physiological parameters to the user.

26. The method of claim 25, further comprising the step of storing said physiological parameters in a database located on a server.

27. The method of claim 26, further comprising the step of providing an authorized person with access to the database based on stored physiological parameters for the user.

28. The method of claim 25, wherein sensing said blood volume contour comprises placing a finger of the user in contact with the PPG sensor.

29. The method of claim 25, wherein step (ii) comprises calculating the fourth derivative of said volume contour for estimating properties of the aortic reflected wave associated with zero crossings on said fourth derivative.

30. The method of claim 29, wherein step (i) comprises bandpass filtering the blood volume contour to produce the filtered blood volume contour.

31. The method of claim 30, wherein said bandpass filtering comprises filtering between 6 and 20 Hertz.

32. The method of claim 25, further comprising providing security access to a resource comprising the steps of:
   (e) storing unique characteristics of an aortic reflected wave contour in a database;
   (f) comparing said extracted characteristics of the user's aortic reflected wave with said unique characteristics of the aortic reflected wave; and
   (g) providing the user with access to the resource only if said extracted characteristics of the user's aortic reflected wave is at least substantially identical to said unique characteristics of the aortic reflected wave.

33. The method of claim 32, wherein step (g) comprises comparing the shape and timing characteristics of said extracted user's aortic reflected wave with the shape and timing characteristics of said unique aortic reflected wave.

34. The method of claim 32, further comprising the step of transmitting said user's aortic reflected wave to a server over a communication network, said server being adapted to verify that said extracted characteristics of the user's aortic reflected wave is at least substantially identical to said unique characteristics of the aortic reflected wave.

35. The method of claim 25, wherein sensing said blood volume contour comprises placing an ear lobe of the user in contact with the PPG sensor.

36. A physiological signal monitoring system for selectively providing a user with access to a resource, said system comprising:
   (a) a PPG sensor adapted to come into skin contact with a user's body part, for sensing a physiological characteristic of the user and for generating electrical signals which correspond to said physiological characteristic;
   (b) processing means operatively coupled to said sensor for receiving and converting said electrical signals into data, for computing a set of physiological parameters on the basis of said data and for extracting characteristics of an aortic reflected wave for the user from said data;
   (c) storage means for storing unique characteristics of an aortic reflected wave contour for the user;
   (d) verification means coupled to said processing means and said storage means for comparing said extracted characteristics of the aortic reflected wave with said unique characteristics of the aortic reflected wave and for providing the user with access to the resource only if said extracted characteristics of the user's aortic reflected wave is at least substantially identical to said unique characteristics of the aortic reflected wave; and,
   (e) display means coupled to said processing means for displaying said physiological parameters.

37. The physiological signal monitoring system of claim 36, wherein said verification means compares the shape and timing characteristics of said extracted characteristics of the user's aortic reflected wave with the shape and timing characteristics of said unique characteristics of the aortic reflected wave.

38. The physiological signal monitoring system of claim 36, wherein said verification means is operatively coupled to said storage means over a communications network.

39. The physiological signal monitoring system of claim 36, wherein said storage means comprises a database server.

* * * * *